(12) United States Patent
Boyd et al.

(10) Patent No.: US 6,613,069 B2
(45) Date of Patent: Sep. 2, 2003

(54) TUNNELING INSTRUMENT FOR PORT ACCESS MULTIVESSEL CORONARY ARTERY BYPASS SURGERY

(75) Inventors: Stephen W. Boyd, Redwood City, CA (US); Alan R. Rapacki, San Francisco, CA (US); Matthias Vaska, Palo Alto, CA (US); Brian S. Donlon, Los Altos Hills, CA (US); William S. Peters, Woodside, CA (US); John H. Stevens, London (GB)

(73) Assignee: Heartport, Inc., Redwood City, CA (US)

( * ) Notice: Subject to any disclaimer, the term of this patent is extended or adjusted under 35 U.S.C. 154(b) by 93 days.

(21) Appl. No.: 09/982,504

(22) Filed: Oct. 19, 2001

(65) Prior Publication Data

US 2002/0087183 A1 Jul. 4, 2002

Related U.S. Application Data

(60) Division of application No. 09/487,024, filed on Jan. 19, 2000, now Pat. No. 6,494,211, which is a continuation-in-part of application No. 08/281,891, filed on Jul. 28, 1994, now Pat. No. 5,735,290, which is a continuation-in-part of application No. 08/023,778, filed on Feb. 22, 1993, now Pat. No. 5,452,733.

(51) Int. Cl.[7] .................................................. A61B 17/44
(52) U.S. Cl. ........................................................ 606/205
(58) Field of Search ............................. 606/46, 51, 52, 606/138, 205, 206, 207, 208, 210; 600/152, 153, 154, 155

(56) References Cited

U.S. PATENT DOCUMENTS

| | | | |
|---|---|---|---|
| 4,531,935 A | 7/1985 | Berryessa | |
| 4,531,936 A | 7/1985 | Gordon | |

(List continued on next page.)

FOREIGN PATENT DOCUMENTS

| | | |
|---|---|---|
| AT | 78668 | 9/1917 |
| CA | 2171097 A1 | 3/1995 |
| DE | 2889924 A5 | 5/1991 |

(List continued on next page.)

OTHER PUBLICATIONS

File History of Reexamination No. 90/005,995 for U.S. Patent No. 5,927,284 as of Jul. 3, 2001.

(List continued on next page.)

*Primary Examiner*—David J. Isabella

(57) ABSTRACT

Surgical methods and instruments are disclosed for performing port-access or closed-chest coronary artery bypass (CABG) surgery in multivessel coronary artery disease. In contrast to standard open-chest CABG surgery, which requires a median sternotomy or other gross thoracotomy to expose the patient's heart, port-access CABG surgery is performed through small incisions or access ports made through the intercostal spaces between the patient's ribs, resulting in greatly reduced pain and morbidity to the patient. In situ arterial bypass grafts, such as the internal mammary arteries and/or the right gastroepiploic artery, are prepared for grafting by thoracoscopic or laparoscopic takedown techniques. Free grafts, such as a saphenous vein graft or a free arterial graft, can be used to augment the in situ arterial grafts. The graft vessels are anastomosed to the coronary arteries under direct visualization through a cardioscopic microscope inserted through an intercostal access port. Retraction instruments are provided to manipulate the heart within the closed chest of the patient to expose each of the coronary arteries for visualization and anastomosis. Disclosed are a tunneler and an articulated tunneling grasper for rerouting the graft vessels, and a finger-like retractor, a suction cup retractor, a snare retractor and a loop retractor for manipulating the heart. Also disclosed is a port-access topical cooling device for improving myocardial protection during the port-access CABG procedure. An alternate surgical approach using an anterior mediastinotomy is also described.

6 Claims, 36 Drawing Sheets

U.S. PATENT DOCUMENTS

| | | |
|---|---|---|
| 4,568,330 A | 2/1986 | Kujawski et al. |
| 4,610,661 A | 9/1986 | Possis et al. |
| 4,637,377 A | 1/1987 | Loop |
| 4,643,190 A | 2/1987 | Heimberger |
| 4,644,651 A | 2/1987 | Jacobsen |
| 4,660,558 A | 4/1987 | Kees, Jr. |
| 4,681,107 A | 7/1987 | Kees, Jr. |
| 4,706,668 A | 11/1987 | Backer |
| 4,760,848 A | 8/1988 | Hasson |
| 4,777,949 A | 10/1988 | Perlin |
| 4,932,955 A | 6/1990 | Merz et al. |
| 4,955,887 A | 9/1990 | Zim |
| 4,961,743 A | 10/1990 | Kees, Jr. et al. |
| 4,973,321 A | 11/1990 | Nichelson |
| 4,974,951 A | 12/1990 | Sander et al. |
| 4,981,471 A | 1/1991 | Quinn et al. |
| 4,997,419 A | 3/1991 | Lakatos et al. |
| 4,998,810 A | 3/1991 | Sander et al. |
| 5,011,469 A | 4/1991 | Buckberg et al. |
| 5,013,296 A | 5/1991 | Buckberg et al. |
| 5,024,668 A | 6/1991 | Peters et al. |
| 5,059,202 A | 10/1991 | Liang et al. |
| 5,074,867 A | 12/1991 | Wilk |
| 5,074,870 A | 12/1991 | von Zeppelin |
| 5,104,393 A | 4/1992 | Isner et al. |
| 5,108,412 A | 4/1992 | Krumeich et al. |
| 5,109,859 A | 5/1992 | Jenkins |
| 5,112,308 A | 5/1992 | Olsen et al. |
| 5,119,983 A | 6/1992 | Green et al. |
| 5,131,905 A | 7/1992 | Grooters |
| 5,133,735 A | 7/1992 | Slater et al. |
| 5,152,780 A | 10/1992 | Honkanen et al. |
| 5,158,543 A | 10/1992 | Lazarus |
| 5,167,628 A | 12/1992 | Boyles |
| 5,169,387 A | 12/1992 | Kronner |
| 5,171,256 A | 12/1992 | Smith et al. |
| 5,173,803 A | 12/1992 | Heller |
| 5,174,300 A | 12/1992 | Bales et al. |
| 5,176,649 A | 1/1993 | Wakahayashi |
| 5,188,619 A | 2/1993 | Myers |
| 5,192,298 A | 3/1993 | Smith et al. |
| 5,201,742 A | 4/1993 | Hasson |
| 5,203,776 A | 4/1993 | Durfee |
| 5,213,093 A | 5/1993 | Swindle |
| 5,219,357 A | 6/1993 | Honkanen et al. |
| 5,221,281 A | 6/1993 | Klicek |
| 5,224,931 A | 7/1993 | Kumar |
| 5,234,447 A | 8/1993 | Kaster et al. |
| 5,234,453 A | 8/1993 | Smith et al. |
| 5,242,456 A | 9/1993 | Nash et al. |
| 5,250,038 A | 10/1993 | Melker et al. |
| 5,271,592 A | 12/1993 | Ludwig |
| 5,282,085 A | 1/1994 | Wolkert et al. |
| 5,292,817 A | 3/1994 | Grey et al. |
| 5,295,477 A | 3/1994 | Janfaza |
| 5,304,183 A | 4/1994 | Grourlay et al. |
| 5,308,320 A | 5/1994 | Safar et al. |
| 5,308,357 A | 5/1994 | Lichtman |
| 5,312,344 A | 5/1994 | Grinfeld et al. |
| 5,313,934 A | 5/1994 | Wita et al. |
| 5,321,447 A | 6/1994 | Sander et al. |
| 5,330,498 A | 7/1994 | Hill |
| 5,339,800 A | 8/1994 | Wita et al. |
| 5,368,600 A | 11/1994 | Faila et al. |
| 5,370,658 A | 12/1994 | Scheller et al. |
| 5,386,817 A | 2/1995 | Jones |
| 5,402,771 A | 4/1995 | Pilling |
| 5,425,705 A | 6/1995 | Evard et al. |
| 5,433,700 A | 7/1995 | Peters |
| 5,451,207 A | 9/1995 | Yock |
| 5,452,733 A | 9/1995 | Sterman et al. |
| 5,467,762 A | 11/1995 | Sauer et al. |
| 5,501,698 A | 3/1996 | Roth et al. |
| 5,509,890 A | 4/1996 | Kazama |
| 5,569,274 A | 10/1996 | Rapacki et al. |
| 5,571,074 A | 11/1996 | Buckman, Jr. et al. |
| 5,571,215 A | 11/1996 | Sterman et al. |
| 5,588,949 A | 12/1996 | Taylor et al. |
| 5,695,504 A | 12/1997 | Gifford, III et al. |
| 5,735,290 A | 4/1998 | Sterman et al. |

FOREIGN PATENT DOCUMENTS

| | | |
|---|---|---|
| EP | 0 218 275 | 4/1987 |
| EP | 0 357 338 | 7/1990 |
| EP | 0 668 058 A1 | 8/1995 |
| GB | 2 140 695 A | 12/1984 |
| GB | 2 255 651 | 11/1992 |
| WO | WO 92/21298 | 12/1992 |
| WO | WO 93/09721 | 5/1993 |
| WO | WO 93/18712 | 9/1993 |
| WO | WO 93/20741 | 10/1993 |
| WO | WO 95/08364 | 3/1995 |

OTHER PUBLICATIONS

File History of Reexamination No. 90/005,994 for U.S. Patent No. 5,836,311 as of Jul. 10, 2001.

Product Brochure–Buhler–ErgonoMIC—System, GmbH, Mehlbeerenstrasse 2, D–8028 Taufkirchen, Germany.

Product Brochure–Suturing, Columbia Prebyterian Hospital, N.Y. New York, and Motreal Medical Center, Tuucker, Georgia.

Product Brochure–Szabo–Beroi Needle Driver Set, Storz, Karl Storz Endoscopy, Apr. 1993.

Product Brochure—"The ultimate" laparoscopic Needle Holder, WJ Medical.

Product Brochure—The Surgical Armamentarium, V. Mueller, Baxter, 1988.

Acufex Rotary Graspers, Acufex Microsurgical, Inc., Catalog, 1982.

Product Brochure—Dekalb Laparoscopic Instruments, Endotec, Endoscopic Technologies, Inc.

Product Brochure—Surgical Instruments, STILLE.RTM., 1993.

Product Brochure, Hermann Dausch—Fabrik Chirurgischer Instrumente, Bahnhofstrasse 76, D–7200 Tuttlingen, Germany.

Androsov, P.I. "New Method of Surgical Treatment of Blood Vessel Lesions", Arch Surg. 73:902–910 (1956).

Anstadt et al., "Direct Mechanical Ventricular Actuation for Cardiac Arrest in Humans, A Clinical Feasibility Trial", The Cardiopulmonary Journal, vol. 100, Jul.–Dec., 1991, pp. 86–92.

Berggren et al. "Clinical Experience with the Unilink/3M Precise Microvascular Anastomotic Device" Scand J Plast Reconstr Hand Surg 27:35–39 (1993).

Buckberg, G.D, "Strategies and Logic of Cardioplegic Delivery To Prevent, Avoid, and Reverse Ischemic and Reperfusion Damage" J Thorac Cardio Vasc Surg, 1987, 93;127–129.

Conolly, John E., "Assisted Circulation" The Textbook of Surgery, the Biological Basis of Modern Surgical Practice, 10th edition, 1972, pp. 2114–2023.

Cooper et al. "Development of the Surgical Stapler with Emphasis on Vascular Anastomosis" Transactions—The New York Academy of Sciences, 23:365–377 (1963).

Cosgrove, D.M. "Management of the Calcified Aorta: An alternative Method of Occlusion" Ann Thorac Surg. 36:718–719 (1983).

Crooke et al., "Biventricular Distribution of Cold Blood Cardioplegic Solution Administered by Different Retrograde Techniques" J Cardiac Thorac Surg,, 1991, 102:4, 631–636.

DelRossi, A.J., et al., "A New Retractor to Aid in Coronary Artery Surgery", Annals of Thoracic Surgery, vol. 36, No. 1, Jul. 1983, pp101–102.

Erath, Jr. and Stoney, Jr. "Balloon Catheter Occlusion of the Ascending Aorta" Ann Thorac Surg. 35:560–561 (1983).

J.H. Foster and J.B. Threlkel "Proximal Control of Aorta with a Balloon Catheter" Surg, Gynecology & Obstetrics pp. 693–694 (1971).

Gentili et al. "A Technique for Rapid Non–Suture Vascular Anastomosis" Can J Neurol Sci 14:92–95 (1987).

Goetz et al. "Internal Mammary–Coronary Artery Anastomosis—A Nonsuture Method Employing Tantalum Rings". Thorac Cardiac Surg 41:378–386 (1961).

Gottlob et al. "Anastomoses of small arteries and veins by means of bushings and adhesive" J. Cardiac Surg 9:337–341 (1968).

Gundry et al., "A Comparison of Retrograde Cardioplegia Versus Antegrade Cardioplegia in the Presence of Coronary Artery Obstruction" Ann Thorac Surg, Aug. 1984, 38:2, 124–127.

Guyton et al. "A Mechanical Device for Sutureless Aorta–Saphenous Vein Anastomosis" Ann Thorac Surg 28:342–345 (1979).

Hoerenz, Peter. "The Operating Microscope: I. Optical Principles, Illumination Systems, and Support Systems", Journal of Microsurgery. Mar./Apr. 1980. 1:364–369.

Hoerenz, Peter. "The Operating Microscope: II. Individual Parts, Handling, Assembling, Focusing, and Balancing", Journal of Microsurgery. May/Jun. 1980. 1:419–427.

Hoerenz, Peter, "The Operating Microscope: III. Accessories", Journal of Microsurgery. Sep. 1980. 2:22–26.

Hoerenz, Peter. "The Operator Microscope: IV. Documentation", Journal of Microsurgery. Dec. 1980. 2:126–139.

Hoerenz, Peter. "The Operating Microscope: V. Maintenance and Cleaning", Journal of Microsurgery. Mar. 1981. 2:179–182.

Holt et al. "A New Technique for End–To–End Anastomosis of Small Arteries" Surg. Forum 11:242 (1960).

Inokuchi, K. "A New Type of Vessel–Suturing Apparatus" Arch Surg. 77:954–957 (1958).

Inokuchi, K. "Stapling Device for End–to–Side Anastomosis of Blood Vessel" Arch. Surg. 82:337–341 (1961).

Ishizaka, "Myocardial Protection by Retrograde Cardiac Perfusion with Cold Modified Krebs Solution Through Coronary Sinus During Complete Ishemic Arrest for 120 min." J Jpn Assn Thorac Surg, 1977, 25:12, 1592–1601.

Kolessov, V.I., The Surgery of Coronary Arteries of the Heart, Leningrad, Meditsina, 1977, pp 360 (Russian Article).

Kolessov, V.I., The Surgery of Coronary Arteries of the Heart, Leningrad, Meditsina, 1977, pp 360 (English Translation).

Landreneau et al. (1992) Ann. Thorac. Surg. 54:800–807.

Lanzetta et al. "Long–term Results of 1 millimeter Arterial Anastomisis Using the 3M Precise Microvascular Anastomotic System" Microsurg 13:313–320 (1992).

Li et al. "End–To–Side Anastomosis in the Dog Using the 3M Precise Microvascular Anastomotic System: A Comparative Study" J. Reconstr Microsurg 7(4):345–350 (1991).

Lust et al., "Improved Protection of Chronically Inflow––Limited Myocardium with Retrograde Coronary Sinus Cardioplegia" Circulation III, Nov. 1988, 78:5, 217–223.

Mack et al. "Present Role of Thorcoscopy in the Diagnosis and Treatment of Disease of the Chest", Ann Thorac Surg 54:403–9 (1992).

Maiern & Druge, "Pericardioscopy—A New Diagnostic Tool in Inflammatory Diseases of the Pericardium", European Heart Journal, (1991)12(Supp. D), pp. 2–6.

Meditech.RTM., Instructions for Use, Occlusion Balloon Catheters Rev. Mar. 1991, pp. 1–7.

Miller, T.R. "The Russian Stapling Device" Transactions—The New York Academy of Sciences 25:378–381 (1963).

Miltex M. Surgical Instruments "Thoracic and Cardiovascular Instruments," Miltex Instrument Co., Inc. 1986, p, 319.

Nakayama et al. "A simple new apparatus for small vessel anastomosis (free autograft of the sigmoid included)" Surgery 52(6):918–931 (1962).

Narter et al. "An Experimental Method for Nonsuture Anastomosis of the Aorta" Surg. Gyn. Obstet 119:362–364 (1964).

Ogawa, K., "Aortic Arch Reconstruction Withour Aortic Cross–Clamping Using Separate Extracorporeal Circulation" J Jpn Assn Thorac Surg, 1993, pp. 2185–2190.

Olearchyk, A.S. "Vasilii I. Kolesov—A pioneer of coronary revascularization by internal mammary–coronary artery grafting" J. Thorac Cardiovasc Surg 96:13–18 (1988).

Peters, W.S., "The Promise of Cardioscopic Surgery" AustralAs J Cardiac Thorac Surg, 1993, 2:3:152–154.

Pilling surgical Instruments "Aortic Claims" 1993 pp. 348–351.

Ragnarsson et al. "Microvenous End–To–Side Anastomosis: An Experimental Study Comparing the Unilink System and Sutures" J Reconstr Microsurg 5(3):217–224 (1989).

Ragnarsson et al. "Arterial End–to–Side Anastomosis with the Unilink System" Ann Plastic Surg 22(5):405–415 (1989).

Razi, D.M., "The Challenge of Calcific Aortitis" J Cardiac Thorac Surg,, 1993, 8:102–107.

Rohman et al. Chapter IX—Cardiovascular Technique "Double Coronary Artery–Internal Mammary Artery Anastomoses, Tantalum Ring Technique" Surg. Forum 11:236 (1960).

Sabiston, D.C., Textbook of Surgery, 10th Ed., 1972, pp. 2021–2023,2114–2121.

Sakaguchi, H. et al., "Aortic Valve Replacement and Coronary Artery Bypass" J. Japanese Assoc. for Thoracic Surgery 41(6):1063–1068 (1993).

Takahashi, M., "Retrograde Coronary Sinus Perfusion for Myocardial Protection in Aortic Valve Surgery" J Jpn Assn Thorac Surg, 1982, 30:3, 306–318.

Vogelfanger et al., "A Concept of Automation in Vascular Surgery: A Preliminary Report on a Mechanical Instrument for Arterial Anastomosis" Can. J. of Surg 1:262–265 (1958).

Yamaguchi, A., "A Case of a Reoperation Using a Balloon Catheter with Blocked Pars Ascendes Aortae" Kyobu Geka, Oct. 1991, 42:11: 961–964.

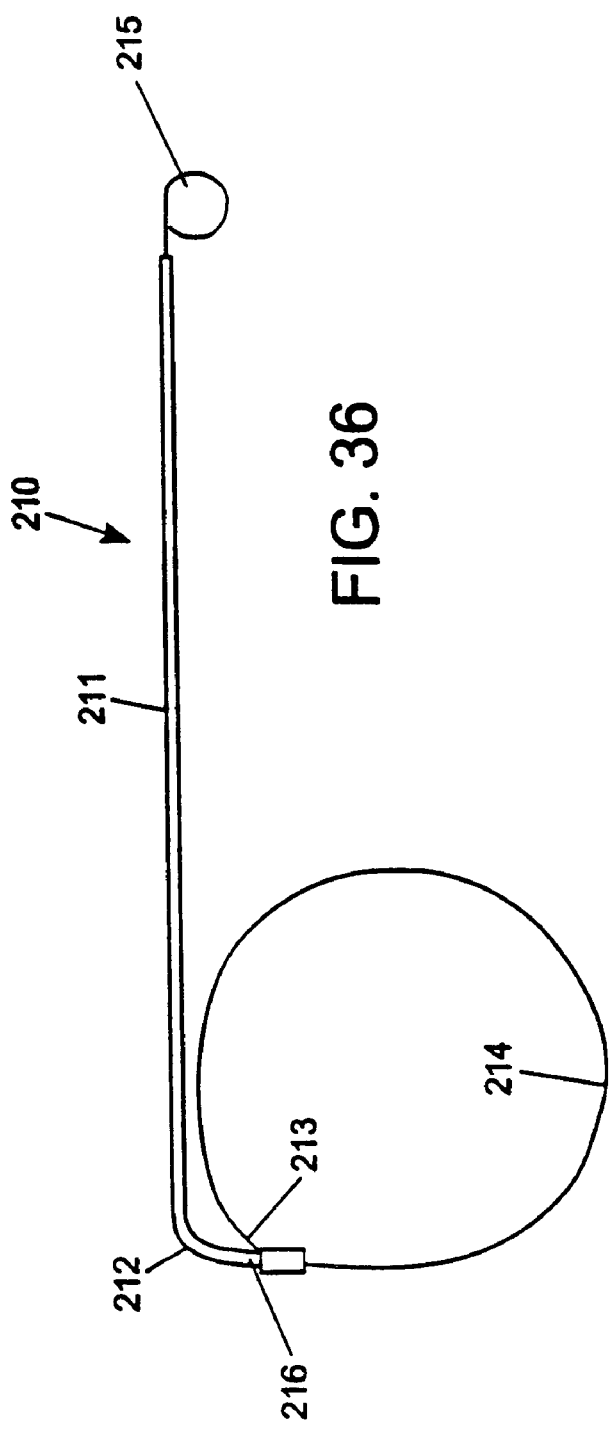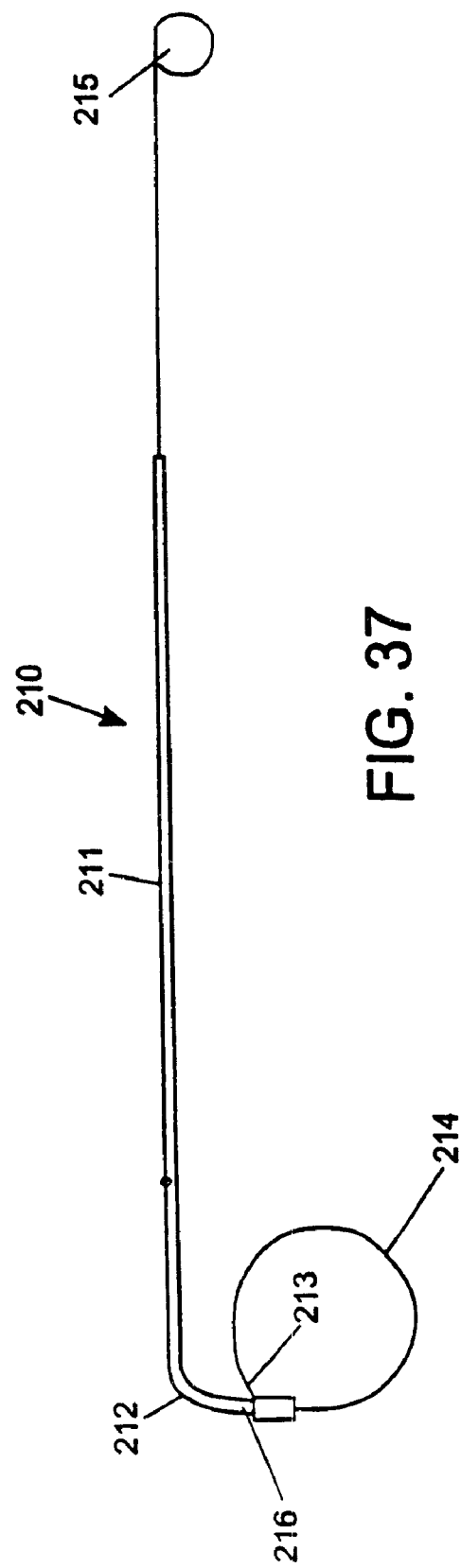

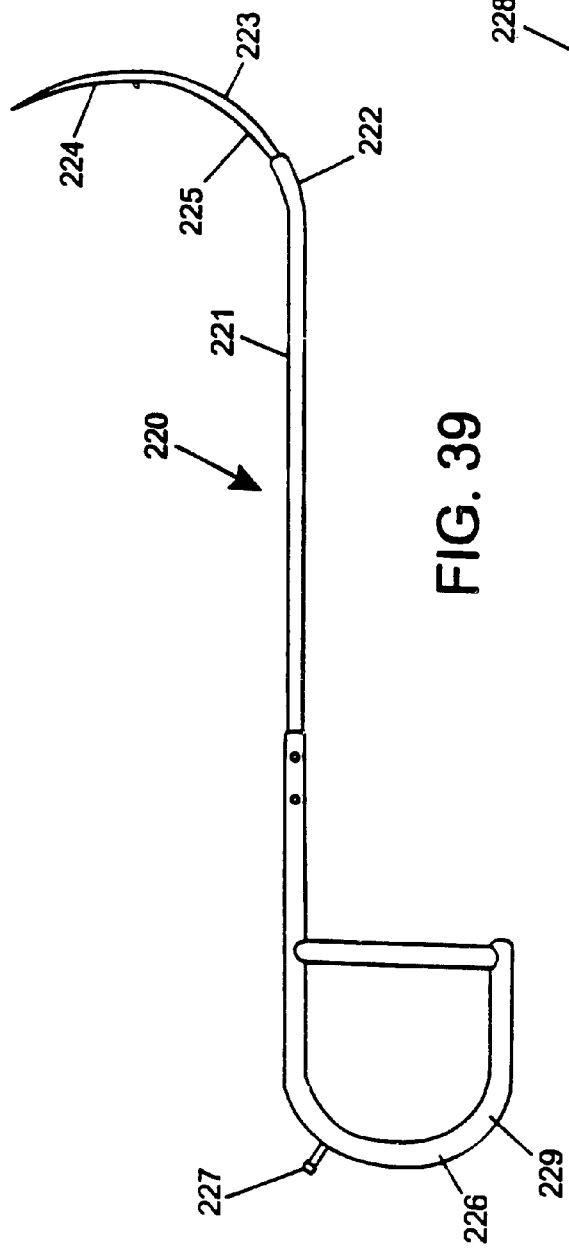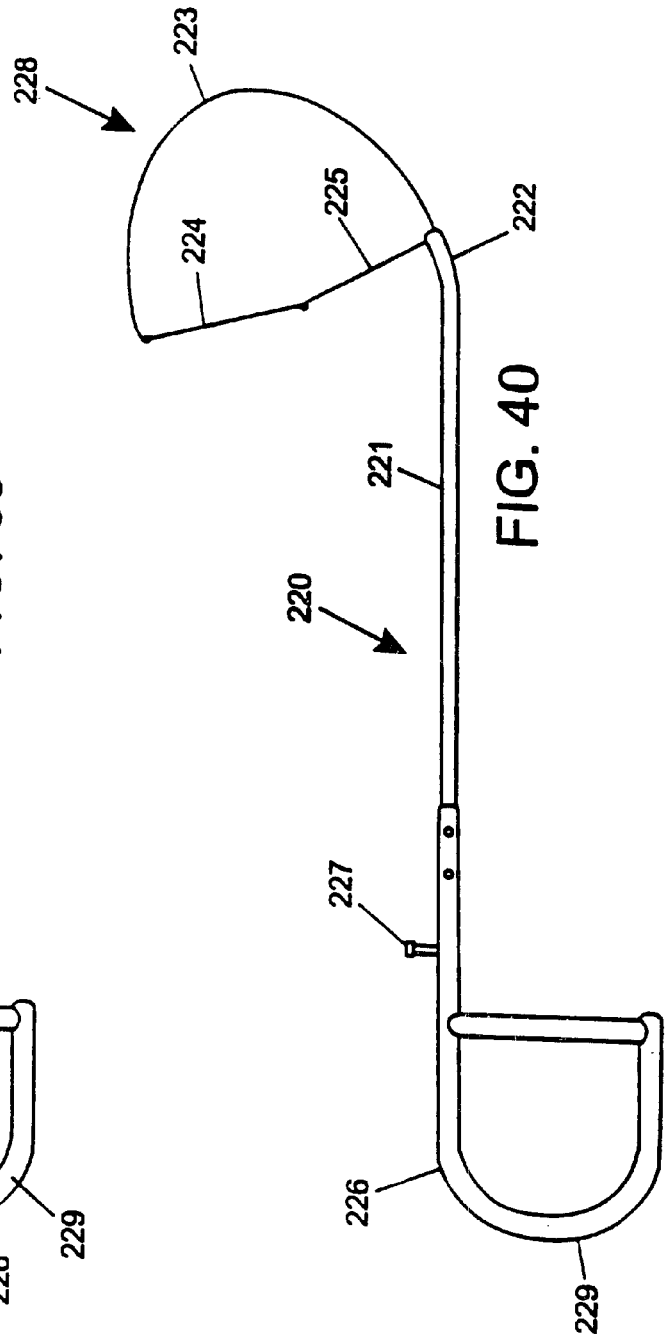
FIG. 39
FIG. 40

TUNNELING INSTRUMENT FOR PORT ACCESS MULTIVESSEL CORONARY ARTERY BYPASS SURGERY

This application is a divisional of U.S. patent application Ser. No. 09/487,024, now U.S. Pat. No. 6,494,211, which is a continuation-in-part of U.S. patent application Ser. No. 08/281,891, filed Jul. 28, 1994 now U.S. Pat. No. 5,735,290, which itself is a continuation-in-part of U.S. patent application Ser. No. 08/023,778, filed Feb. 22, 1993, now U.S. Pat. No. 5,452,733. The complete disclosures of these related U.S. patent applications are hereby incorporated herein by reference for all purposes.

FIELD OF THE INVENTION

The present invention relates generally to devices and methods for performing thoracoscopic cardiac procedures. More particularly, the present invention relates to devices and methods for performing coronary artery bypass graft (CABG) surgery for multivessel coronary artery disease through port-access or closed-chest thoracoscopic methods.

BACKGROUND OF THE INVENTION

Coronary artery disease remains the leading cause of morbidity and mortality in Western societies. Coronary artery disease is manifested in a number of ways. For example, disease of the coronary arteries can lead to insufficient blood flow resulting in the discomfort and risks of angina and ischemia. In severe cases, acute blockage of coronary blood flow can result in myocardial infarction, leading to immediate death or damage to the myocardial tissue.

A number of approaches have been developed for treating coronary artery disease. In less severe cases, it is often sufficient to treat the symptoms with pharmaceuticals and lifestyle modification to lessen the underlying causes of disease. In more severe cases, the coronary blockage(s) can often be treated endovascularly using techniques such as balloon angioplasty, atherectomy, laser ablation, stents, hot tip probes, and the like.

In cases where pharmaceutical treatment and/or endovascular approaches have failed or are likely to fail, it is often necessary to perform a coronary artery bypass graft procedure using open surgical techniques. Such techniques require that the patient's sternum be opened and the chest be spread apart to provide access to the heart. A source of arterial blood is then connected to a coronary artery downstream from an occlusion while the patient is maintained under cardioplegia and is supported by cardiopulmonary bypass. The source of blood is often the left or right internal mammary artery, and the target coronary artery can be the left anterior descending artery, circumflex artery, right coronary artery or any one of their branches which might be narrowed or occluded.

While very effective in many cases, the use of open surgery to perform coronary artery bypass grafting is highly traumatic to the patient. The procedure requires immediate postoperative care in an intensive care unit, a total period of hospitalization of seven to ten days, and a recovery period that can be as long as six to eight weeks.

It would therefore be desirable to provide other, less traumatic methods and techniques for performing coronary artery bypass grafting. It would be particularly desirable if such techniques did not require opening of the patient's sternum, and might be even more desirable if such techniques could be performed using thoracoscopic methods. Such thoracoscopic methods could decrease morbidity and mortality, cost, and recovery time when compared to conventional open surgical coronary bypass procedures. In addition, such methods could be even more efficacious than open-surgical bypass procedures.

Treatment of multivessel coronary artery disease involves rerouting multiple conduits to supply blood to the blocked coronary arteries downstream of the blockages. Typical conduits used for CABG surgery in multivessel disease include arterial conduits, such as the left internal mammary artery (LIMA), the right internal mammary artery (RIMA) or the right gastroepiploic artery (RGEA), or venous conduits such as the greater saphenous vein (GSV) or the lesser saphenous vein (LSV). Often a combination of these and other conduits is necessary to achieve complete revascularization of the obstructed coronary arteries. Open-chest approaches to treatment of multivessel coronary artery disease are described in *Alternative Bypass Conduits and Methods for Surgical Coronary Revascularization,* by Grooters and Nishida, Futura Publishing Company, Inc., Armonk, N.Y., 1994. Other references for standard open-chest methods of coronary artery bypass surgery include: *Cardiac Surgery,* by Kirklin and Barratt Boyes, John Wiley & Sons, Inc. New York, 1993 (2nd Ed.), and Rob and Smith's *Operative Surgery, Cardiac Surgery,* The CV Mosby Co., St Louis, Mo., 1983 (4th Ed.).

A major challenge of thoracoscopic CABG surgery in multivessel disease is the ability to visualize and anastomose all of the coronary arteries through a limited number of access ports in order to minimize the trauma to the patient. This is made more difficult because many of preferred anastomosis sites on the branches of the right coronary artery and the circumflex artery are on the posterior aspect of the heart and therefore are difficult to access and to visualize with the heart in situ. Operating on the heart in situ would require separate access ports for the left coronary artery and each of the right coronary artery and the circumflex artery. Making this many access ports in the patient's chest would undermine the atraumatic aspect of the thoracoscopic approach. In open-chest CABG surgery, this problem is solved by withdrawing the heart from the pericardial sac and manipulating it to expose the arteries on the posterior aspect. No instruments currently exist for manipulating the heart within the closed chest of the patient, making it difficult to duplicate the close-chest procedure with thoracoscopic techniques. Devices and methods are therefore necessary for manipulating the heart within the patient's closed chest to expose each of the coronary arteries for visualization and anastomosis.

The additional length of time required for performing multiple anastomoses in multivessel CABG surgery also poses difficulties in terms of myocardial preservation during the lengthy procedure. In open procedures additional myocardial protection can be provided by topical hypothermia of the heart to reduce oxygen demand by the myocardium. The instruments and systems currently available for topical hypothermia in cardiac surgery are not suited for thoracoscopic techniques. New devices and methods are therefore necessary for cooling the heart within the patient's closed chest to extend myocardial preservation during the multivessel CABG procedure.

SUMMARY OF THE INVENTION

The present invention describes devices and methods for performing port-access or closed-chest CABG surgery to treat multivessel coronary artery disease. All of the major steps of the port-access CABG procedure are performed through small percutaneous access ports to avoid the necessity of a median sternotomy or other gross thoracotomy, as required in prior open-chest approaches. The methods of the present invention include the steps of dissecting one or more conduit vessels, preferably arterial conduits, from their native locations, rerouting the conduit vessels to the heart and grafting the conduit vessels onto the blocked coronary arteries downstream of the blockages.

Generally, the step of dissecting the conduit vessels from their native locations or the "takedown" is performed through small access ports using endoscopic visualization. In the case of a LIMA or RIMA takedown, the access ports are made into the patient's thoracic cavity through the intercostal spaces and visualization is achieved using a flexible thoracoscope. Rerouting the LIMA involves redirecting the distal end of the LIMA to the desired anastomosis site. The RIMA may be rerouted anteriorly of the heart or it may be tunneled through the transverse sinus to reach the desired anastomosis site. In the case of an RGEA takedown, the access ports are made into the patient's abdomen and visualization is achieved using a laparoscope. Rerouting the RGEA involves tunneling the distal end of the RGEA through a hole in the diaphragm to reach the desired anastomosis site on the heart. If venous grafts, such as the GSV, or other free grafts are used in place of or in addition to the arterial conduits, then the takedown or harvesting of the graft is performed by open or closed surgical techniques as appropriate and the graft is rerouted to the patient's chest for anastomosis.

Specialized instruments for facilitating the takedown and rerouting steps are provided as part of the present invention. One instrument provided is a thoracoscopic tunneler for directing an arterial conduit through the transverse sinus or other tunneling path. One embodiment of a tunneler has an elongated shaft with a curved, rigid distal end with a hole through the distal tip for passing a tape or silastic tube through the transverse sinus to retract the aorto-pulmonary trunk to facilitate passage of the arterial conduit through the transverse sinus. Another embodiment of a tunneler has an elongated shaft with an articulated distal end with a grasper for reaching through the transverse sinus to grasp the arterial conduit and draw it through the transverse sinus to the desired anastomosis site. The two tunneling instruments may be used separately or in combination. In addition, a specialized thoracoscopic electrosurgical device may be provided to facilitate takedown of the arterial conduits. A suitable thoracoscopic electrosurgical device for this application is described in co-owned, copending patent application, Ser. No. 08/336.359, filed Nov. 8, 1994. the entire disclosure of which is hereby incorporated by reference.

The step of grafting the conduit vessels onto the heart is accomplished under direct visualization using a cardioscopic microscope inserted through a visualization port into the patient's thoracic cavity made through an intercostal space in the anterior wall of the chest. Additional surgical instruments are inserted through auxiliary ports into the patient's thoracic cavity to perform the anastomosis of the conduit vessels to the coronary arteries. The devices and methods of the present invention are devised to minimize the trauma to the patient by making it possible to visualize and access all aspects of the heart from a single centrally located visualization port by manipulating the heart within the patient's closed chest with instruments inserted through the auxiliary access ports or through the takedown ports which remain from the takedown step. Generally, the distal end of each conduit vessel or graft is anastomosed to a coronary artery downstream of a blockage. Additionally, the conduit vessels may be sequentially grafted to more than one coronary artery or branch to form a "skip graft". If free grafts are used an additional step of creating a proximal anastomosis must be performed. The proximal end of the graft may be anastomosed to the ascending aorta or to another of the conduit vessels to form a Y-graft. The step of making the proximal anastomosis may be performed before or after the distal anastomosis, depending on the preferences of the surgeon.

Specialized instruments are provided for manipulating the heart within the closed chest of the patient to rotate the desired anastomosis site into the visual field of the cardioscopic microscope. The specialized instruments include retractors which can manipulate the heart from outside of the body through one or more of the access ports. One embodiment of a retractor has an elongated shaft with a handle at the proximal end and a curved, finger-like manipulator at the distal end. The curved, finger-like manipulator may be covered with an absorbent and/or frictional material to improve its effectiveness at retracting, rotating and manipulating the heart. Another embodiment of a retractor has an elongated tubular shaft with a suction cup-shaped manipulator at the distal end. A vacuum is applied between the suction cup manipulator and the surface of the heart to grip the heart. The distal surface of the suction cup manipulator may have a textured or highly frictional surface to increase the grip on the surface of the heart, especially in a direction tangential to the surface. The retractor can thus be used to retract or rotate the heart in any direction to expose the desired anastomosis site.

Another aspect of the present invention is to provide myocardial protection to the heart for the duration of the surgical procedure. A first component of the myocardial protection is to provide a means for establishing cardiopulmonary bypass (CPB) without the need for performing a thoracotomy or other grossly invasive procedure. One noninvasive method of establishing CPB involves the insertion of an endoaortic occlusion catheter into the ascending aorta through a percutaneous puncture into a peripheral artery. An inflatable occlusion balloon on the distal end of the catheter is used to partition the ascending aorta between the coronary ostia and the brachiocephalic artery to isolate the heart and coronary arteries from the remainder of the arterial system while it is supported on cardiopulmonary bypass. Cardioplegic solution to temporarily stop the heart from beating may be infused into the coronary arteries through the catheter and/or through a retroperfusion catheter percutaneously inserted in the coronary sinus. This method is more completely described in co-owned, copending patent application, Ser. No. 08/281,891, filed Jul. 28, 1994.

Another relatively noninvasive method of establishing CPB involves using a thoracoscopic cross-clamp to isolate the heart and coronary arteries from the remainder of the arterial system while it is supported on cardiopulmonary bypass. The thoracoscopic cross-clamp is inserted into the patient's thoracic cavity through an access port. Co-owned, copending patent application, Ser. No. 08/173,899, filed Dec. 27, 1993, the entire disclosure of which is hereby incorporated by reference, describes a specialized thoracoscopic cross-clamp suitable use with the present invention and a method of its use for isolating the heart and establishing CPB.

A second component of the myocardial protection is to provide a means for applying topical hypothermia to the heart to reduce oxygen demand by the myocardium while the patient is on cardiopulmonary bypass and particularly while the heart is under cardioplegic arrest. A specialized topical hypothermia system that can be applied thoracoscopically through small access ports into the chest is provided as part of the present invention. The topical hypothermia system includes a flexible heat exchanger which is collapsible to fit through an access cannula inserted into an intercostal space. The heat exchanger is deployable to an expanded position once it is inside of the thoracic cavity. The heat exchanger is placed in thermal contact with the heart and a cooling fluid is circulated from outside the body through cooling passages within the heat exchanger. The temperature of the heart can be lowered for the duration of the procedure to reduce oxygen demand. The heat exchanger can also be used for warming the heart at the end of the procedure by circulating a warm fluid through the cooling passages.

BRIEF DESCRIPTION OF THE DRAWINGS

FIG. 36 shows a third embodiment of a heart retractor with a flexible snare on the distal end for manipulating the heart.

FIG. 37 shows the heart retractor of FIG. 36 in a predeployed position for insertion through an access cannula.

FIG. 39 shows a fourth embodiment of a heart retractor for manipulating the heart in a predeployed position for insertion through an access cannula.

FIG. 40 shows the heart retractor of FIG. 39 in a deployed position for manipulating the heart.

DETAILED DESCRIPTION OF PREFERRED EMBODIMENTS

The Surgical Method

Figure 1:
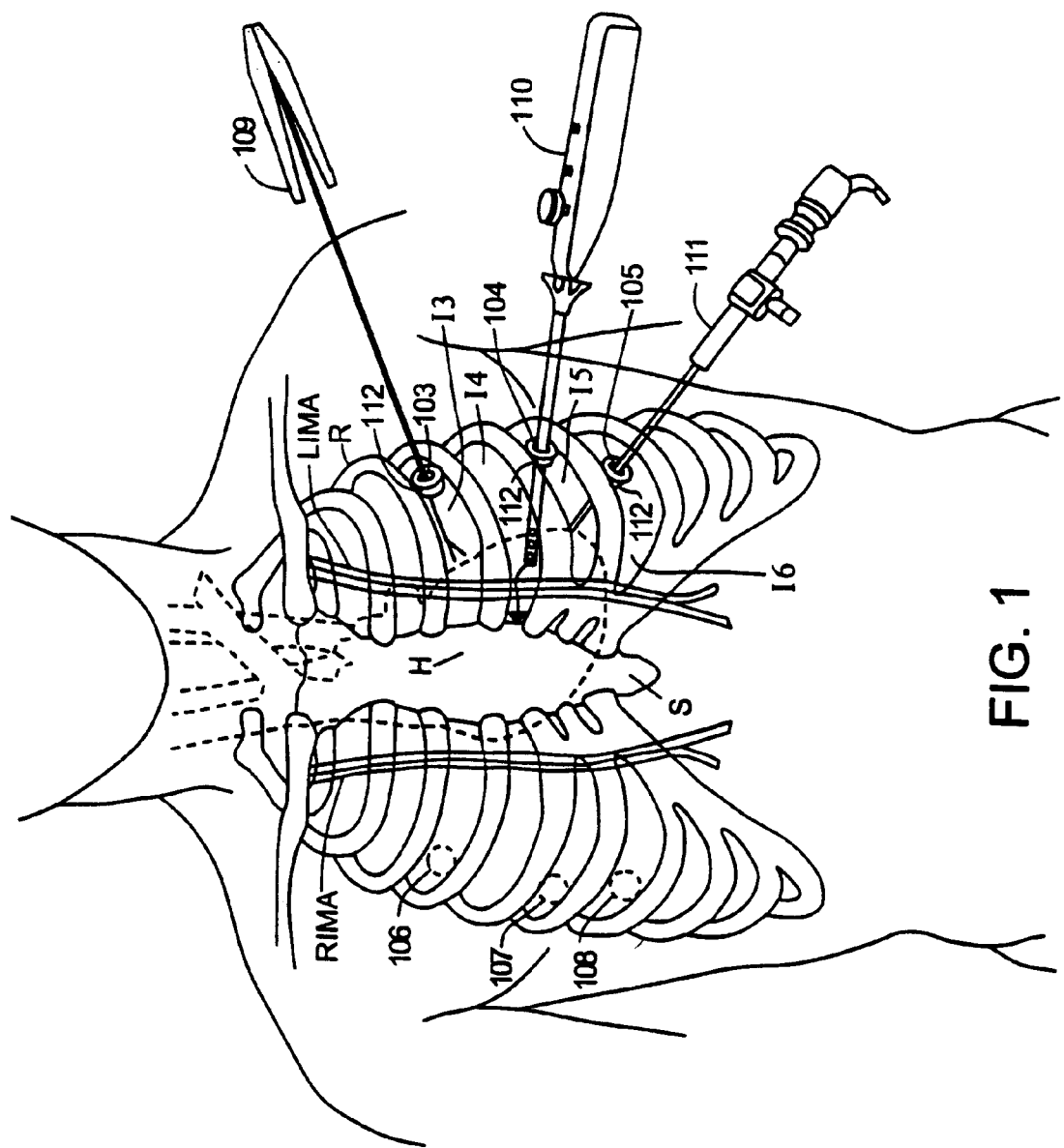
FIG. 1 shows the takedown step for using the left internal mammary artery (LIMA) or the right internal mammary artery (RIMA) as an arterial bypass conduit.

FIG. 1 is a schematic view of a patient's thorax illustrating the takedown step of the port-access CABG procedure. The takedown step should be performed while the patient is under general anesthesia, but before the patient has been placed on cardiopulmonary bypass. If the LIMA is to be used as an arterial bypass conduit, a series of access ports are created on the left lateral side of the patient's chest, as shown in FIG. 1. The access ports are created by incising the skin with a scalpel between two of the patient's ribs, then an access cannula 112 with a trocar is pushed through the intercostal space. Preferably, a self-anchoring access cannula 112 with a 10–12 mm internal diameter is used for the takedown ports. The placement of the access ports is highly variable, depending on the preferences of the surgeon and the anatomy of the patient which is assessed fluoroscopically before the operation to verify the preferred locations.

In one preferred embodiment of the method, to allow the takedown of the LIMA, a first access port 103 is placed in the third intercostal space I3 on the left lateral side of the patient's chest, a second access port 104 is placed in the fifth intercostal space I5, and a third access port 105 is placed in the sixth intercostal space I6 in a slightly more anterior position from the first two. Meanwhile, the left and right bronchi are individually intubated just below the bifurcation of the trachea so that the lungs can be individually ventilated. The left lung is deflated to provide clearance between the lung and the left anterior wall of the thoracic cavity while the patient is ventilated through the right lung. A flexible thoracoscope 111 is inserted through one of the access ports, such as the third access port 105 as shown in FIG. 1. The distal end of the flexible thoracoscope 111 can be directed toward the anterior wall of the thoracic cavity just to the left of the sternum S to view the LIMA. Elongated instruments, such as an electrosurgical device 110 and a grasper 109, are inserted through the remaining ports 104, 103 to dissect the LIMA from the anterior wall of the chest. The LIMA is dissected with an attached pedicle. Side branches of the LIMA are ligated with ligating clips, applied with a thoracoscopic clip applier, as the LIMA is dissected from the surrounding tissue. A length of LIMA of 15–30 cm is dissected from the wall to provide enough length to reach the chosen anastomosis site. When a sufficient length of LIMA has been dissected, two ligating clips are placed side-by-side near the distal end of the LIMA and the vessel is transected between them.

If the patient's lungs are ventilated by high frequency "jet" ventilation, then the RIMA can also be harvested from the access ports 103, 104, 105 on the left side of the patient's chest, provided the patient's chest has ample space between the heart and the anterior wall of the thoracic cavity. To do this, both lungs are partially deflated while continuing to ventilate, thereby allowing clearance to reach the RIMA from the left side of the chest. After dissecting the mediastinal pleura, the distal end of the thoracoscope 111 is directed toward the anterior wall of the thoracic cavity just to the right of the sternum S to view the RIMA and the RIMA is taken down in a similar fashion to the LIMA.

If conventional ventilation is used, sufficient ventilation cannot be achieved with both lungs partially deflated, so this option is not available. In this case, access ports 106, 107, 108 symmetrical to the left hand ports are placed in the lateral right side of the chest, typically in the third I3, fifth I5 and sixth I6 intercostal spaces. The right lung is deflated to provide clearance between the lung and the anterior wall of the thoracic cavity while the left lung is ventilated. The flexible thoracoscope 111 is inserted through one of the access ports and instruments, such as the electrosurgical device 110, graspers 109 and/or a clip applier, are inserted through the remaining ports to dissect the RIMA from the anterior chest wall. A length of 15–30 cm of RIMA with an attached pedicle is dissected from the chest wall to provide enough length to reach the chosen anastomosis site. When a sufficient length of RIMA has been dissected, two ligating clips are placed side-by-side near the distal end of the RIMA and the vessel is transected between them.

Figure 2:
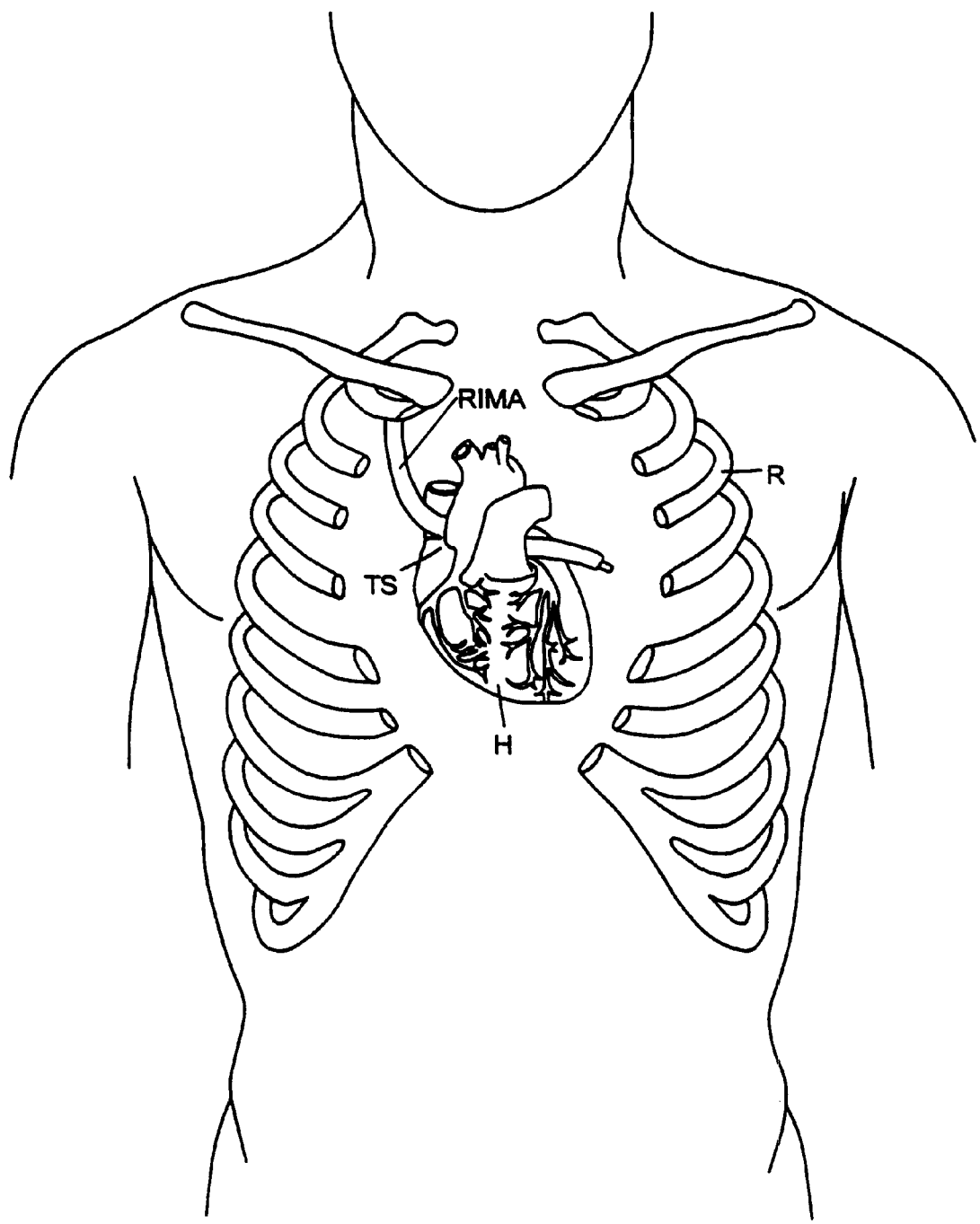
FIG. 2 shows the tunneling of the RIMA through the transverse sinus (TS).

When rerouting the RIMA to the anastomosis site, two paths are possible. The currently preferred path is through the transverse sinus TS which is a natural passage behind the aorta A and the pulmonary artery P leading from the right side of the heart H to the left side. The RIMA is tunneled through the transverse sinus TS by passing an instrument, such as the articulated tunneling grasper 150 described below in relation to FIG. 24, through the transverse sinus TS and drawing the distal end of the RIMA back through the transverse sinus TS, as shown in FIG. 2. (nota bene: The patient's chest has been shown with the ribs R cut away in FIG. 2, and subsequent figures, solely for the purposes of illustration. An important feature of the port-access surgical method of the present invention is that the ribs and the sternum remain intact throughout the surgical procedure.) To facilitate the tunneling operation, a tunneler 140, such as the one described below in relation to FIG. 22, can be used to retract the pulmonary trunk P to allow easier passage of the RIMA through the transverse sinus TS. The second path for rerouting the RIMA is across the anterior side of the heart H. This routing of the RIMA is not currently preferred by most surgeons in open-chest CABG operations because the oscillating saw commonly used for doing the sternotomy in redo CABG operations can cause damage to the RIMA if it is placed in an anterior position. However, it is interesting to note that redo CABG will not require the oscillating saw to open the sternotomy if the original CABG operation was done with port-access techniques that do not require a sternotomy. The less traumatic reciprocating saw, commonly used in first time CABG surgery, can be used if a redo operation is necessary because it will be the patient's first sternotomy. As the techniques for port-access CABG surgery advance, the simpler anterior route for the RIMA is likely to become the preferred path.

Figure 3:
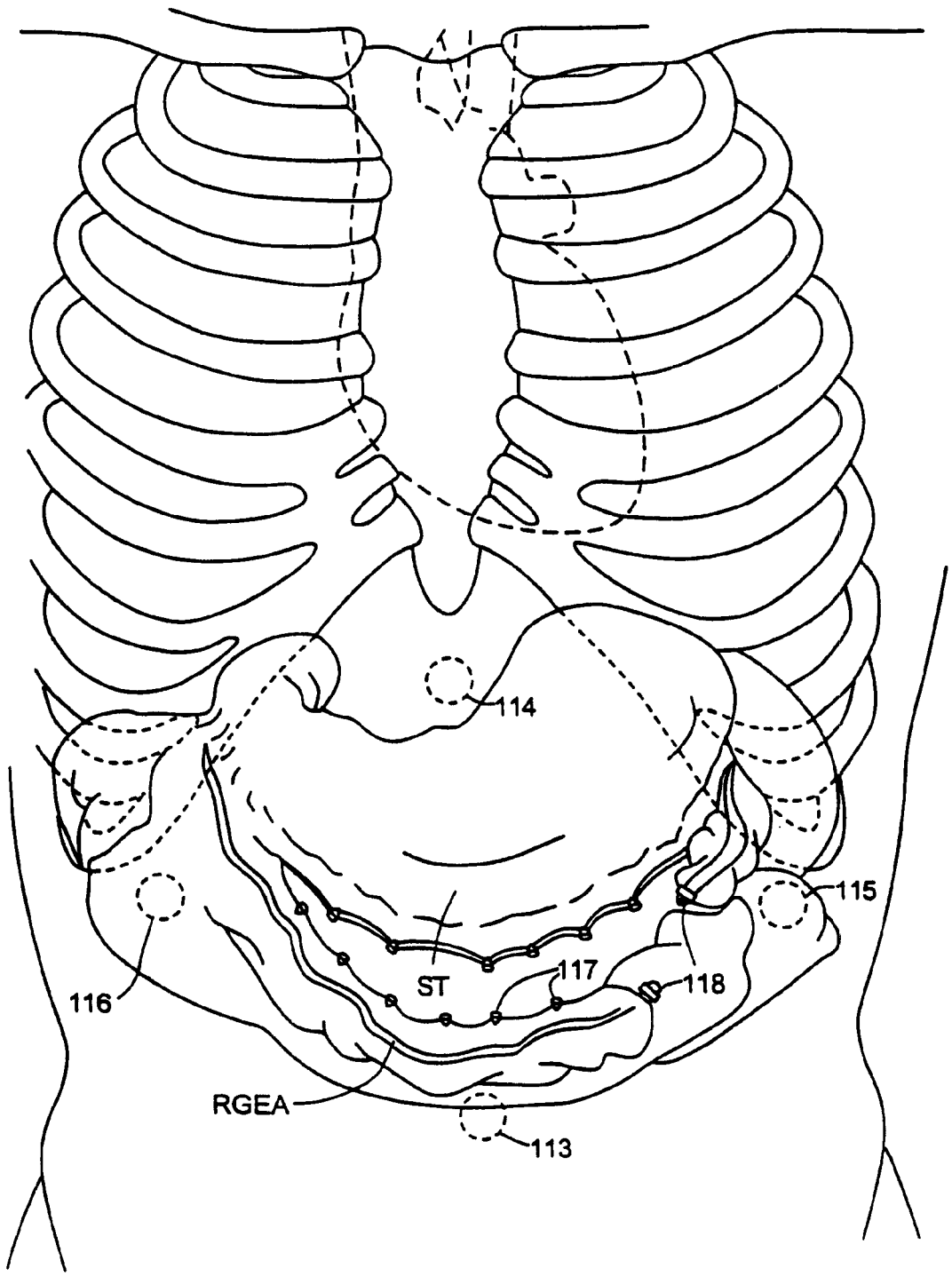
FIG. 3 shows the laparoscopic takedown of the right gastroepiploic artery (RGEA).

If a third arterial conduit is required for complete revascularization of the heart or if either of the internal mammary arteries is not available, then the right gastroepiploic artery (RGEA) is the next choice. FIG. 3 shows the laparoscopic takedown step for the RGEA. A first laparoscopic access port 113 is placed above the umbilicus and a second laparoscopic access port 114 is placed below the diaphragm. A third 115 and fourth 116 access ports may be placed in the left and right side of the abdomen as shown for insertion of instruments. The RGEA is dissected from the greater curvature of the stomach ST using an electrosurgical device. Ligating clips are placed on branches of the RGEA running toward the omentum. Branches 117 running toward the stomach are preferably ligated with suture. A length of 15–30 cm of RGEA with an attached pedicle is dissected from the stomach to provide enough length to reach the chosen anastomosis site. When a sufficient length of RGEA has been dissected, two ligating clips 118 are placed side-by-side near the distal end of the RGEA and the vessel is transected between them.

Figure 4:
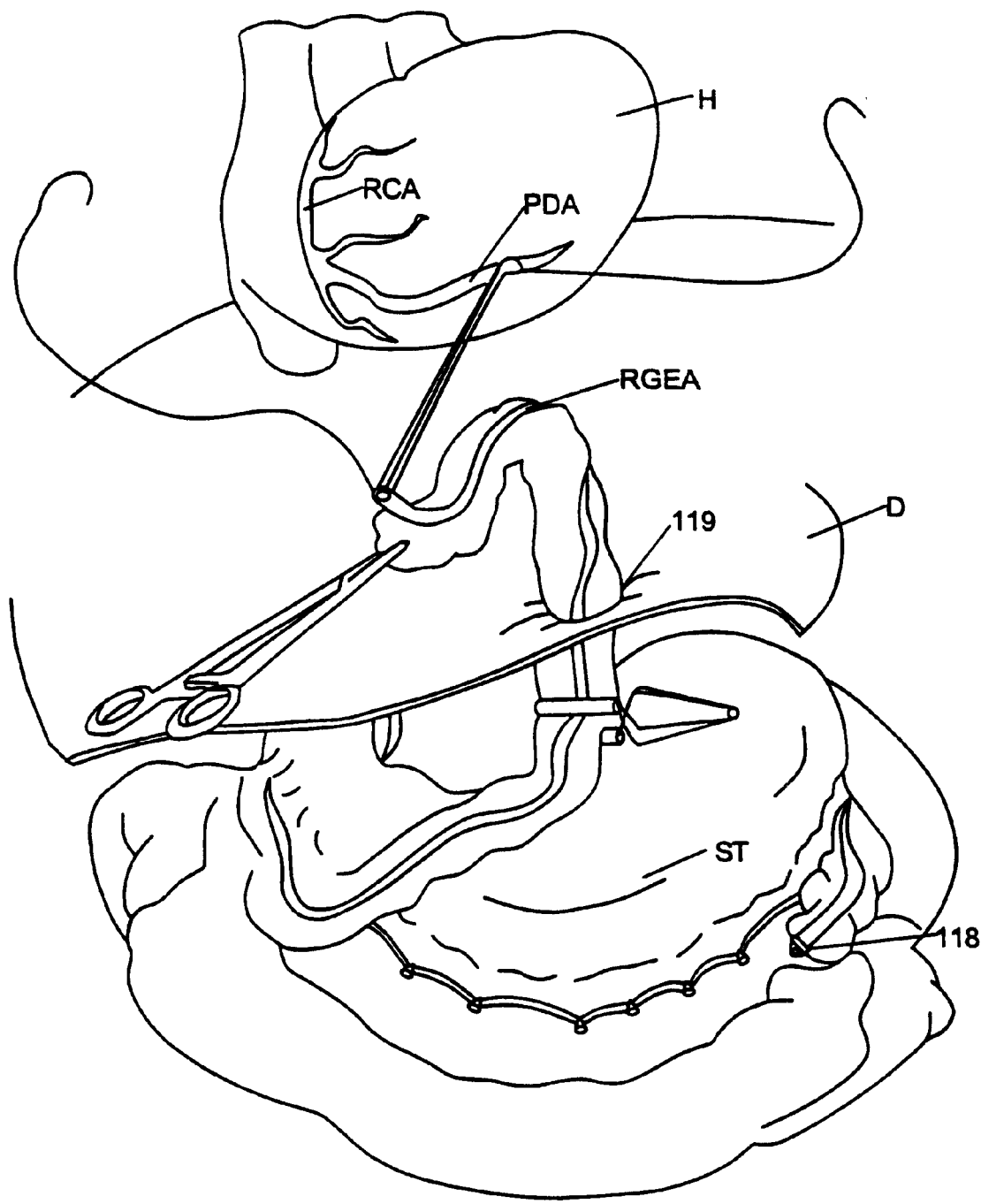
FIG. 4 shows the tunneling of the RGEA through the diaphragm into the thoracic cavity.

A hole 119 is made through the diaphragm D in an appropriate place for reaching the desired anastomosis site using an electrosurgical device. The distal end of the RGEA is tunneled upward through the diaphragm D as shown in FIG. 4. In FIG. 4, the rerouted RGEA is shown being anastomosed to the PDA on a heart H which has been retracted by the methods described below to expose the posterior aspect of the heart.

If a venous graft, such as the greater saphenous vein (GSV), is needed, a venous takedown procedure can be performed by known techniques to provide a venous conduit. After harvesting, the vein can be prepared for use as a graft outside of the body and inserted into the thoracic cavity through one of the access ports at the appropriate time in the grafting step of the procedure.

Simultaneously with the takedown step or steps just described, the patient can be prepared for cardiopulmonary bypass by cannulating the femoral artery and the femoral vein using surgical cutdowns or the percutaneous Seldinger technique. Additionally, an endoaortic occlusion catheter may be positioned in the ascending aorta according to the methods described in co-owned, copending patent application Ser. No. 08/281,891, filed Jul. 28, 1994. According to the methods described therein, an elongated endoaortic occlusion catheter is introduced into a peripheral artery, such as the femoral artery and advanced into the ascending aorta. When it is time to establish CPB before the grafting step described below, an occlusion balloon on the distal end of the catheter is inflated to occlude the aortic lumen between the coronary ostia and the brachiocephalic artery. Once the balloon is inflated a cardioplegic agent can be infused through a lumen in the catheter into the aortic root and into the coronary arteries to induce cardiac arrest. Alternatively, a thoracoscopic cross-clamp may be introduced through one of the access ports according to the methods described in co-owned, copending patent application Ser. No. 08/173,899, filed Dec. 27, 1993, the entire disclosure of which is hereby incorporated by reference. According to the methods described therein, an elongated thoracoscopic cross-clamp is introduced through one of the access ports and, at the appropriate time, clamped around the ascending aorta to occlude the aortic lumen. A cardioplegic agent may be introduced antegrade into the aortic root or retrograde through the coronary sinus to induce cardiac arrest. This is in preparation for the grafting step of the method of the present mention which follows.

At this point in the procedure the pericardium is opened to expose the heart as completely as possible. Using thoracoscopic observation, grasping instruments and cutting instruments, such as knives, scissors and/or an electrosurgical device are inserted through the takedown ports 103, 104, 105 and a vertical slit beginning at or near the aortic reflection and extending to the apex of the heart is made in the pericardium. Thoracoscopic bipolar electrosurgical cutting scissors, such as model 3803 bipolar scissors from Everest Medical Corporation, Minneapolis, Minn., have proven to be an effective instrument for performing the pericardiotomy. The pericardium is divided to expose the surface of the heart H to view.

Figure 5:
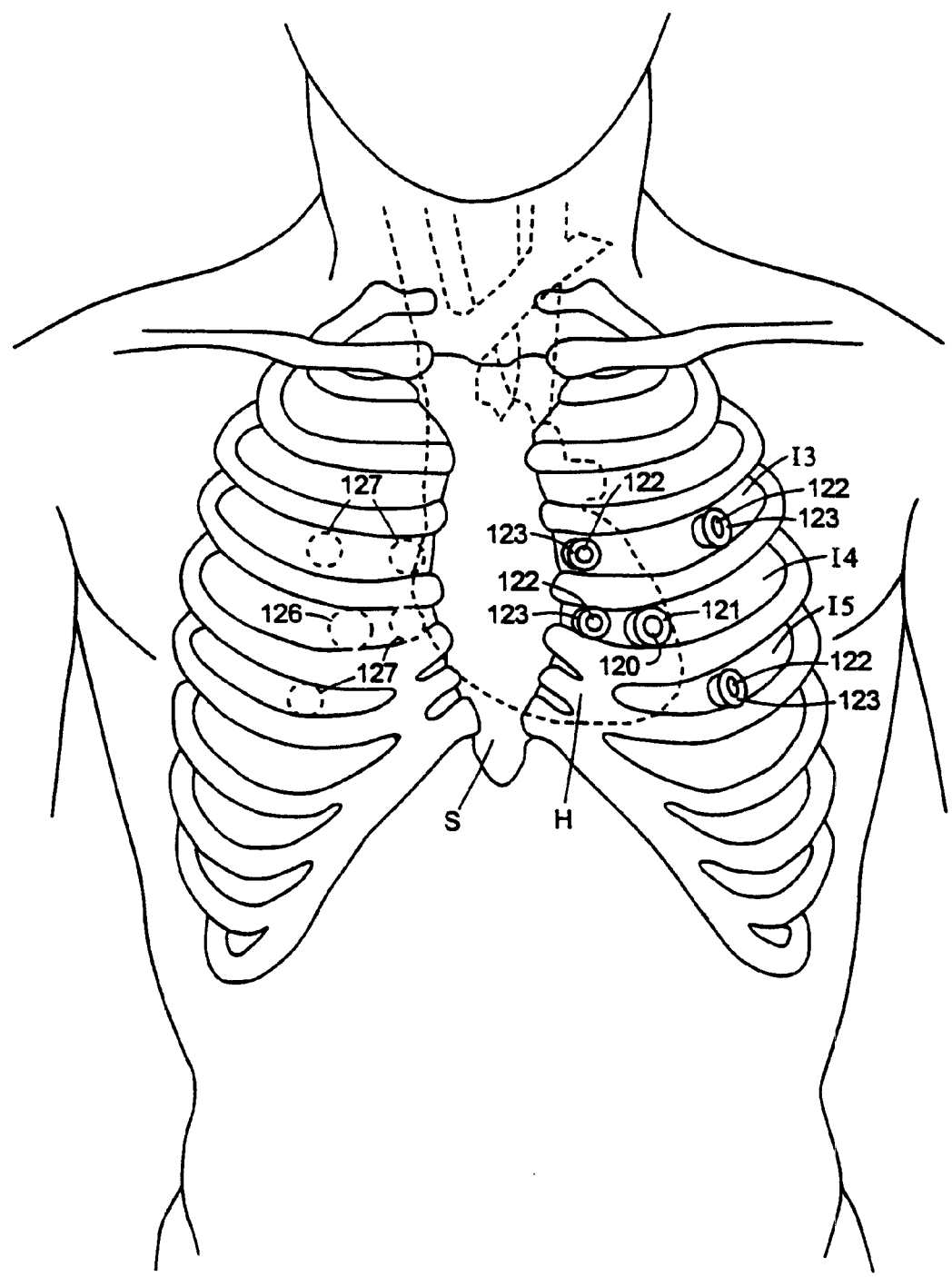
FIG. 5 shows the operative ports for performing the anastomosis of the arterial conduits onto the coronary arteries.

FIG. 5 shows the operative ports for performing the anastomosis of the arterial conduits onto the coronary arteries. A visualization port 120 is placed in the anterior wall of the chest, typically through the fourth intercostal space I4, about 1–3 cm from the sternum S. The precise placement of the visualization port 120 is determined by the position of the heart H within the patient's chest. A probe, such as a 22 gauge needle can be inserted percutaneously through the intercostal space while observing the anterior wall of the thoracic cavity through the thoracoscope. When the needle is observed entering the thoracic cavity above the target position, for instance above the LAD when the heart is in its native position, the needle is removed and a trocar is used to create an access port at that position. An access cannula 121 with an internal diameter of 10–12 mm is placed in the access port 120 and the cardioscopic microscope (not shown) is inserted through the cannula. A cardioscopic microscope, adapted especially for this port-access CABG procedure is available from Karl Zeiss, GmbH, Germany. The presently preferred configuration uses an OPMI® microscope, model MDU or CS, with an NC31 microscope stand, an endoscopic adapter and a Port-Access StereoVision Probe. Other types of microscope-based and direct visualization systems which are particularly well-suited for use in the method of the present invention are disclosed in co-owned, copending patent applications Ser. No. 08/135,387, filed Oct. 8, 1993, and Ser. No. 08/227,366, filed Apr. 13, 1994, the complete disclosures of which are hereby incorporated herein by reference. With the microscope positioned in the visualization port 120, the left anterior descending coronary artery (LAD) should be within the field of view of the microscope.

A number of instrument ports 122 are placed about 3–5 cm from the visualization port to allow proper angulation of the instruments into the field of view of the microscope. Typically, two ports 122 are placed near the sternum S in the third I3 and fourth I4 intercostal spaces and two more ports 122 are placed to the left of the visualization port in the third I3 and fifth I5 intercostal spaces. An access cannula 123 with an internal diameter of 5 mm is placed in each of the instrument ports 122.

Next the graft vessels, whether arterial or venous conduits, must be prepared for anastomosis. Preferably, the distal ends of the graft vessels are prepared outside of the body by passing the distal end of the graft out through one of the access ports. This simplifies the procedure because the end of the graft can be prepared under direct visualization with magnifying surgical loupes and because standard surgical instruments can be used for preparing the graft rather than thoracoscopic instruments. The LIMA or RIMA can be passed out through one of the thoracic access ports (e.g. access port 103 or 106 in FIG. 1) before rerouting or tunneling the vessel. The RGEA can be passed out through one of the abdominal access ports (e.g. access port 113 or 114 in FIG. 3) before tunneling the RGEA through the diaphragm D. If the graft vessel is too short to reach the exterior of the body through one of the access ports, the following graft vessel preparation procedure can also be carried out within the thoracic cavity using thoracoscopic instruments and techniques. Prior to preparing the graft vessel, the blood flow into the vessel must be stopped by placing an atraumatic clamp (e.g. 124 in FIG. 4) on the upstream end of the vessel. An atraumatic thoracoscopic bulldog clamp especially suited for this step of the procedure is described in co-owned, copending patent application Ser. No. 08/265,477. filed Jun. 24, 1994.

The graft vessel should be prepared by first determining the appropriate length of the conduit in order to reach the desired anastomosis site. The distal end of the graft vessel should then be skeletonized by stripping the pedicle away from the artery for 5–10 mm. The distal end of the artery is transected to remove the ligating clip 118 that was previously applied. If desired, Papavarin may be injected into the lumen of the artery to dilate it and reverse any arterial spasm. Depending on the technique preferred by the surgeon, the distal end of the graft vessel can be slit longitudinally to create a cobra head for the anastomosis. Once prepared, the graft vessel is reinserted into the thoracic cavity through the access port.

When performing multiple anastomoses, it is preferable to do the most difficult or most difficult to reach anastomosis first. For example, any anastomosis to the RCA or the PDA should be performed first since the most retraction of the heart is necessary. Following that, any anastomosis to the Cx or the OM branches should be performed. Finally, any anastomosis to the LAD can be performed last. The RIMA, RGEA or a vein graft may be used for anastomosis to the RCA or the PDA which are on the posterior aspect of the heart. Typically, the LIMA, RIMA or a vein graft is used when a graft is needed for the Cx or the OM branches because of their location on the left aspect of the heart. The LIMA, or the RIMA if the LIMA has already been used for the Cx, may be used for anastomosis to the LAD which is on the anterior aspect of the heart. Because the manifestations of coronary artery disease are highly variable, the extent of the disease should be assessed fluoroscopically beforehand and the anastomosis sites and the best use of the available conduits strategized carefully. The procedures for anastomosing to each of the major anastomosis sites will now be described. These procedures can be performed in combination to achieve complete revascularization of the heart.

Figure 6:
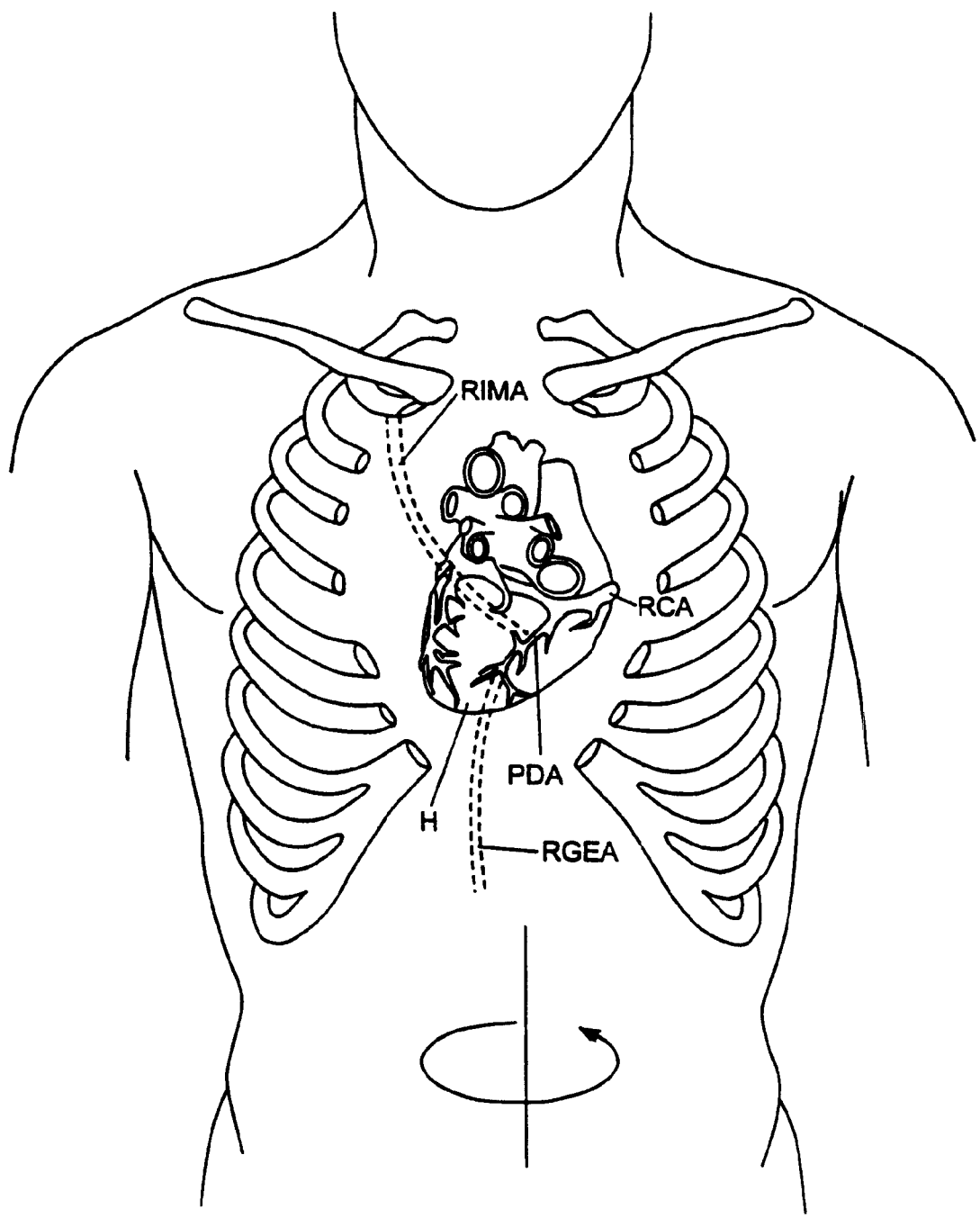
FIG. 6 shows a position of the heart for performing an anastomosis to the right coronary artery (RCA) or the posterior descending (PDA) branch.

FIG. 6 shows a first position of the heart H for performing an anastomosis to the right coronary artery (RCA) or the posterior descending (PDA) branch. The heart H is manipulated from outside of the body using instruments inserted through the instrument ports 122 or the takedown ports 103, 104, 105 in the patient's chest. Using the heart retractor devices described below in connection with FIGS. 26 and 27 or any suitable means for manipulating the heart from outside of the body, the heart H is rotated approximately 180 degrees to the left of the patient to position the RCA and/or PDA under the microscope in the visualization port 120. With the heart H stabilized in this position, the distal extremity of the conduit vessel is approximated to the chosen anastomosis site and an end-to-side anastomosis is performed. The likely graft vessels for the RCA and the PDA, which include the RIMA and the RGEA, are shown in phantom lines in FIG. 6. After completion of the anastomosis, the heart H is rotated back to its native position or to the desired position for the next anastomosis.

Figure 7:
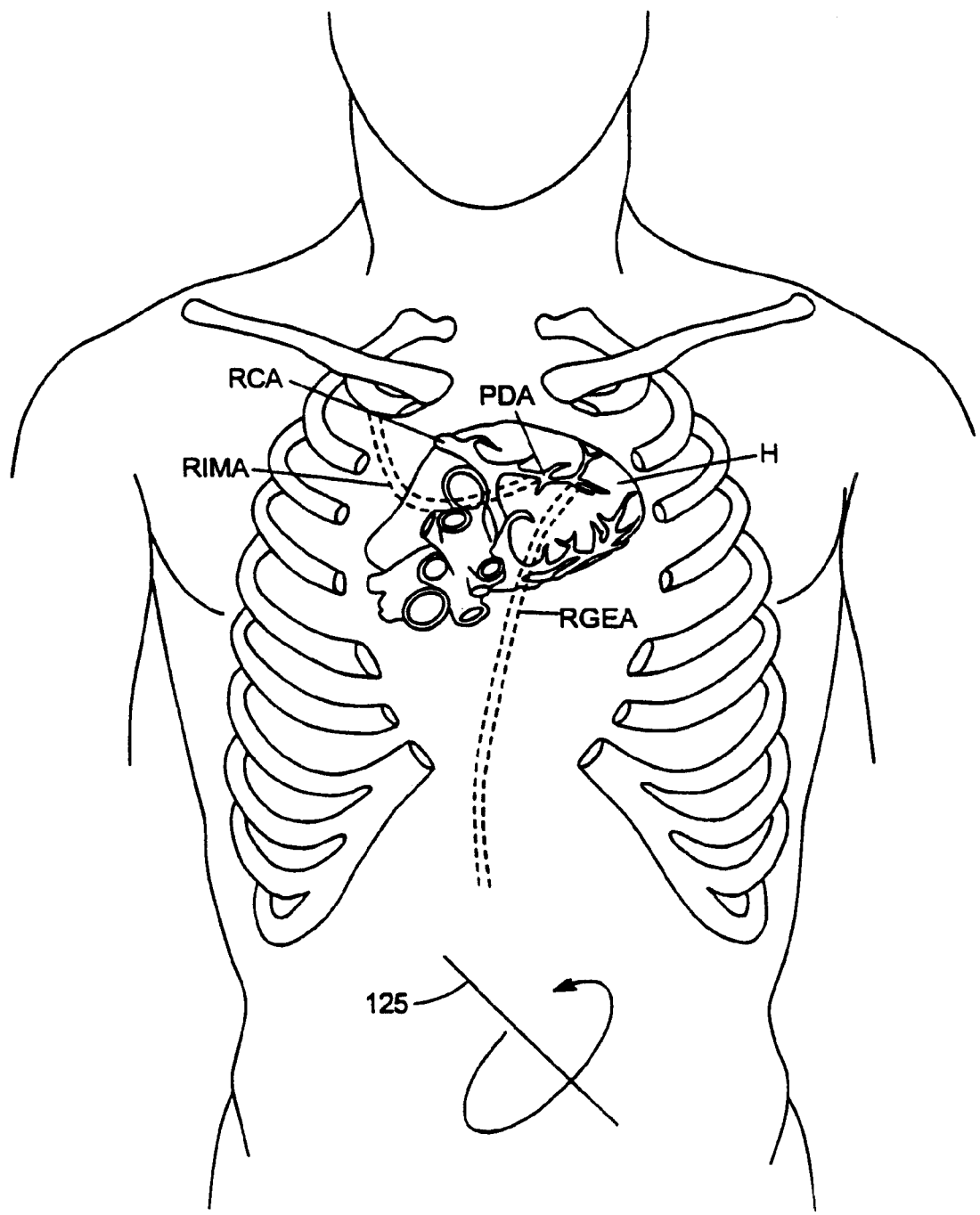
FIG. 7 shows an alternate position of the heart for performing an anastomosis to the RCA or the PDA.

FIG. 7 shows an alternate position of the heart H for performing the anastomosis to the RCA or the PDA. In this variation of the procedure, the heart H is rotated approximately 180 degrees about an axis 125 which is at an approximately 45 degree angle to the sagittal axis of the body. Flipped upward this way, the RCA and the PDA are positioned under the microscope in the visualization port 120. With the heart H stabilized in this position, the distal extremity of the conduit vessel is approximated to the chosen anastomosis site and an end-to-side anastomosis is performed. The likely graft vessels for the RCA and the PDA, which include the RIMA and the RGEA, are shown in phantom lines in FIG. 7. After completion of the anastomosis, the heart H is rotated back to its native position or to the desired position for the next anastomosis.

Figure 8:
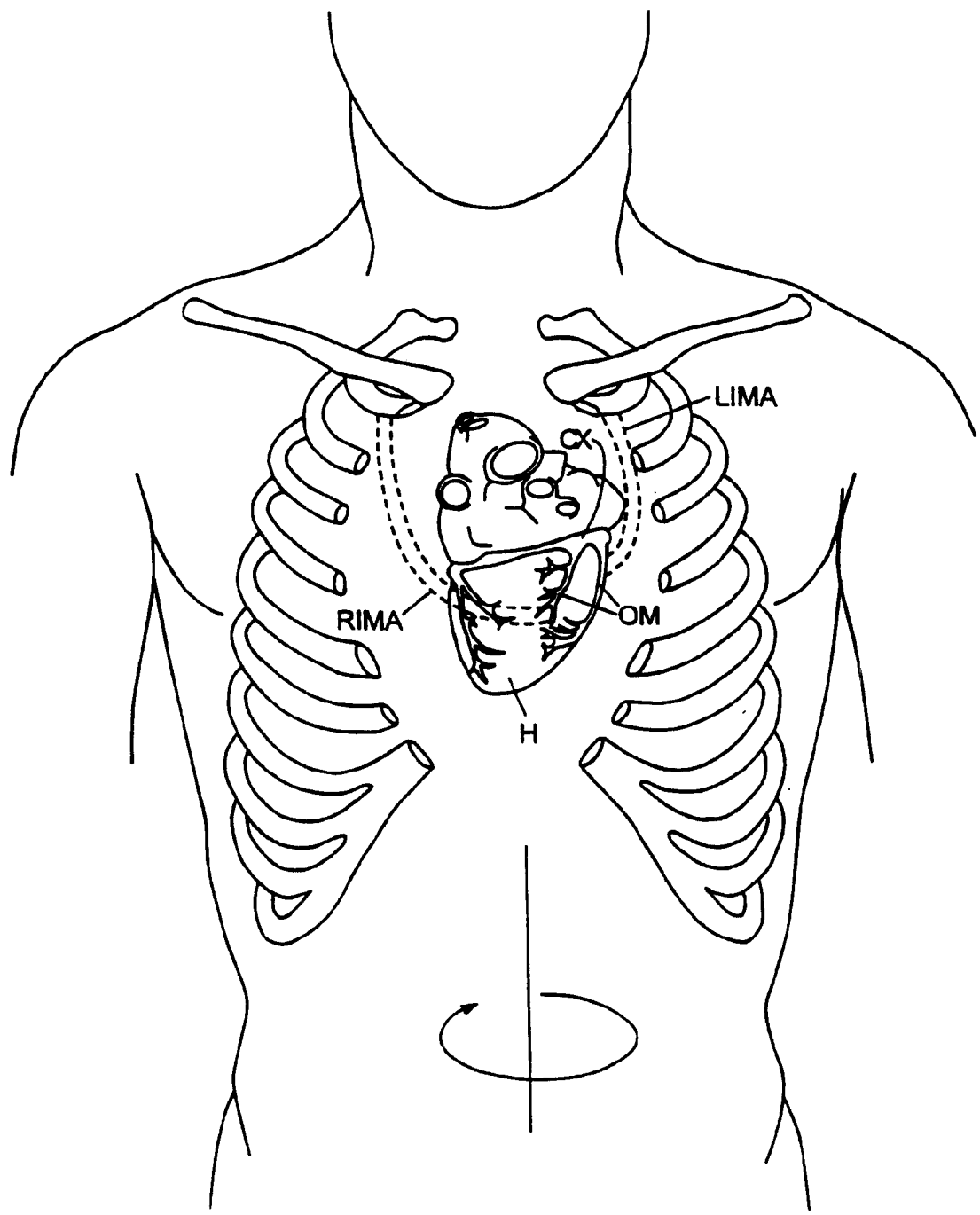
FIG. 8 shows the position of the heart for performing an anastomosis to the circumflex artery (Cx) or the obtuse marginal (OM) branches.

FIG. 8 shows the position of the heart H for performing an anastomosis to the circumflex artery (Cx) or the obtuse marginal (OM) branches. In order to access the Cx or the OM branches which are on the left aspect of the heart or the left posterior aspect of the heart, the heart H is rotated toward the right by 45 to 90 degrees using retraction instruments inserted through the access ports (e.g. 103, 104, 105). In this position the Cx and/or the OM branches will be positioned under the microscope in the visualization port 120. With the heart H stabilized in this position, the distal extremity of the conduit vessel is approximated to the chosen anastomosis site and an end-to-side anastomosis is performed. The likely graft vessels for the Cx and the OM branches, which include the LIMA and the RIMA, are shown in phantom lines in FIG. 8. After completion of the anastomosis, the heart H is rotated back to its native position or to the desired position for the next anastomosis.

Figure 9:
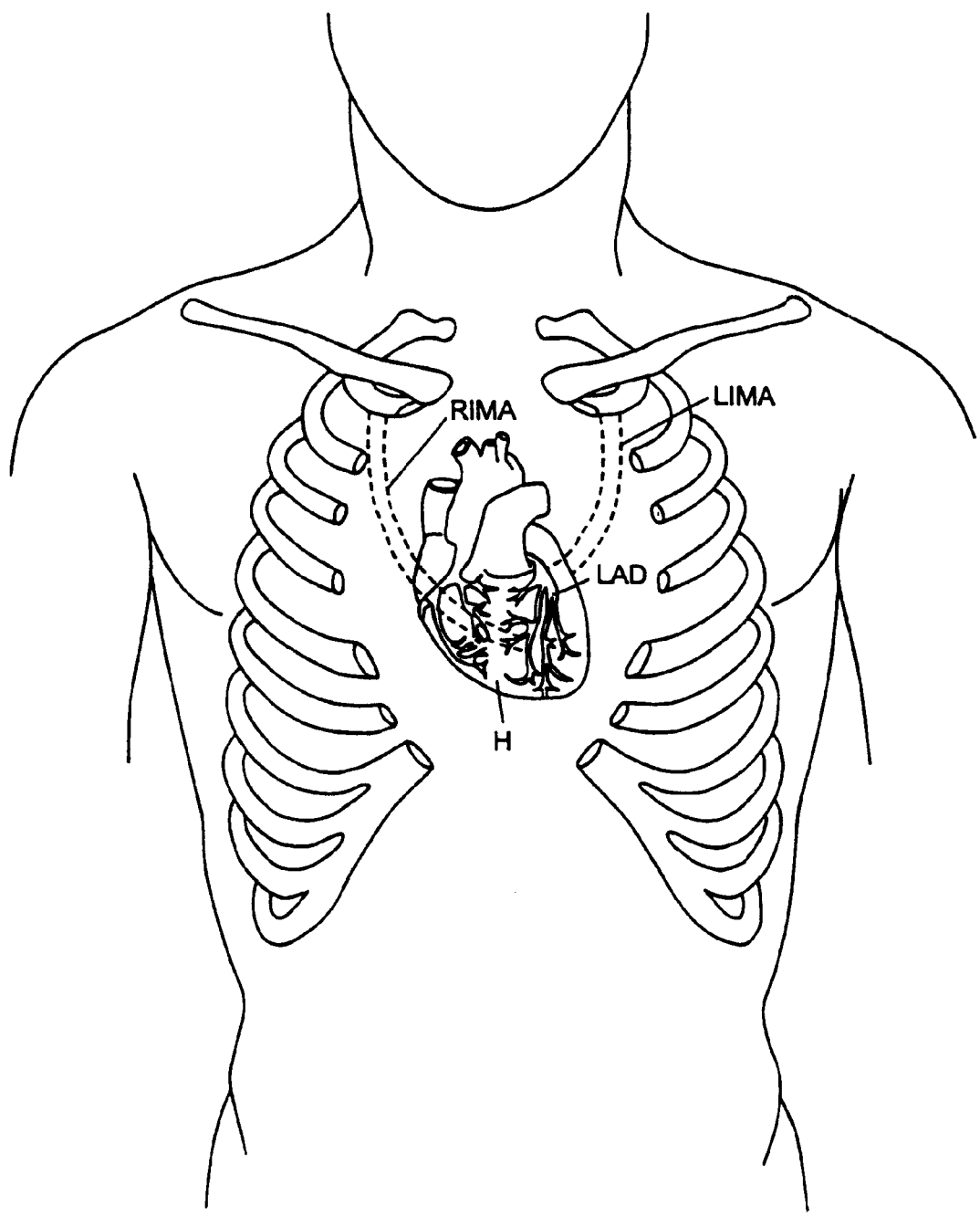
FIG. 9 shows the position of the heart for performing an anastomosis to the left anterior descending artery (LAD).

With the more difficult to reach anastomoses completed and the heart H back in its native position, as shown in FIG. 9 the anastomosis to the LAD can now be completed. With the heart H in its native position, the LAD will be positioned under the microscope in the visualization port 120. With the heart H stabilized in this position, the distal extremity of the conduit vessel is approximated to the chosen anastomosis site and an end-to-side anastomosis is performed. The likely graft vessels for the LAD, which include the LIMA and the RIMA, are shown in phantom lines in FIG. 9.

Alternatively to manipulating the heart within the closed chest to expose the different aspects, a second visualization port 126 and instrument ports 127 can be opened on the right side of the chest, as shown in phantom lines in FIG. 5, to access the right coronary artery RCA directly. In another alternative approach, right side access ports may be used alone if only the right coronary artery RCA and/or the obtuse marginal OM branches are to be revascularized or if the patient's anatomy favors a right side approach for multivessel revascularization.

Figure 10:
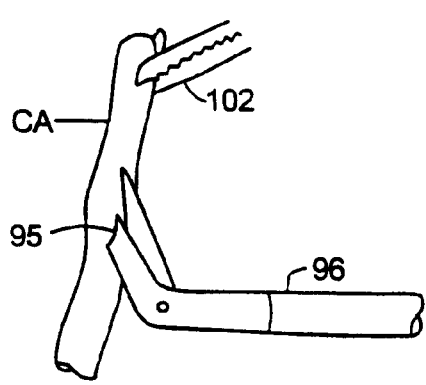
FIGS. 10–15 show the step-by-step sequence of creating an end-to-side anastomosis.

FIGS. 10–15 show the step-by-step sequence of creating an end-to-side anastomosis. Referring now to FIG. 10, an incision 95 is made in the wall of the coronary artery CA, where the incision has dimensions selected to match those of the distal end of the internal mammary artery graft IMA. The incision 95 is made by first piercing the arterial wall using the tip of a scalpel (not illustrated). Scissors 96 are then introduced through the penetration and used to axially extend the penetration, as illustrated at 97 in FIG. 11.

The internal mammary artery IMA can be joined to the extended incision 97 in the coronary artery CA by a variety of techniques, including suturing, laser welding, microstapling, and the like. In a currently preferred embodiment of the method of the present invention, it is preferred to use a continuous suturing technique as illustrated in FIGS. 10–15. A length of suture 98 has needles 100 at either end, which are manipulated using forceps 102 to join the distal end 101 of the internal mammary artery IMA graft to the opening created by the incision 97 in the coronary artery CA, as shown in FIGS. 11–15. The instrument designs presently preferred for performing the coronary anastomosis are described in copending application Ser. No. 08/194,946, filed Feb. 11, 1994, the entire disclosure of which is hereby incorporated herein by reference. Alternatively, an interrupted suture technique for the anastomosis can be used, as described in Rob and Smith's *Operative Surgery, Cardiac Surgery* for open-chest CABG surgery.

The presently preferred suture for port-access CABG surgery is a double-armed suture of 8–10 cm length which was specially developed for this procedure. The suture 98 has a first needle 100 on one end and a second needle 100 on the other end. Preferably, the needles 100 are ⅜ circle curved hardened stainless steel needles with tapered points. The needles 100 are preferably attached to the suture 98 by crimping. Alternatively, the needles 100 may be adhesively bonded to be suture 98. The preferred suture material 98 is a multifilament, expanded PTFE suture material with a size between 8-0 and 6-0 USP, preferably 7-0 USP. Suitable suture material of this type is available from W.L. Gore, Corporation under the tradename Goretex®. A contrasting color which is highly visible within the thoracic cavity, such as black, blue or white, is preferred for the suture material.

Figure 11:
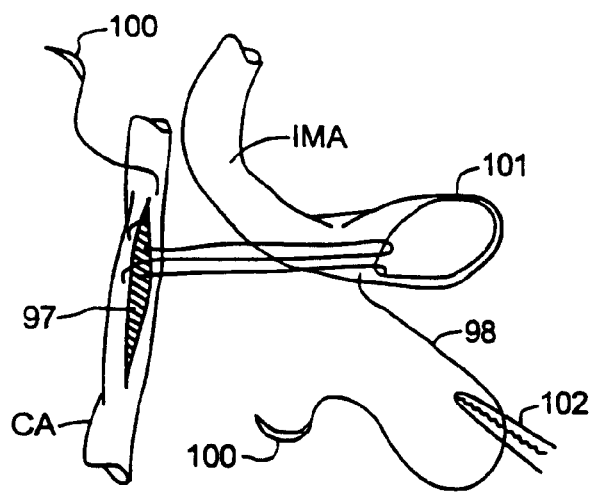
Figure 12:
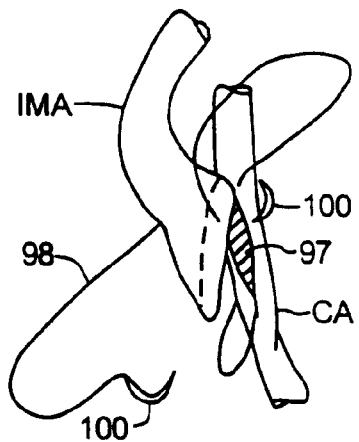
Figure 13:
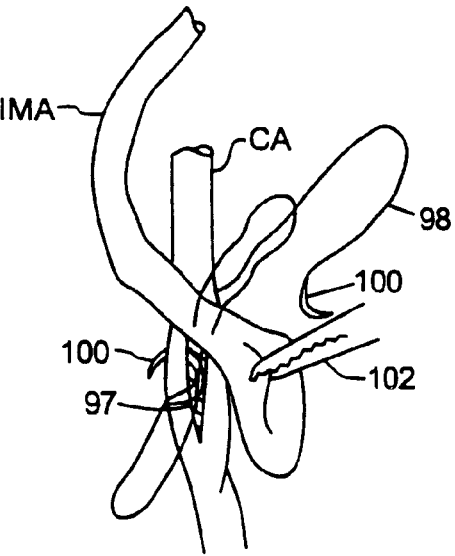
Figure 14:
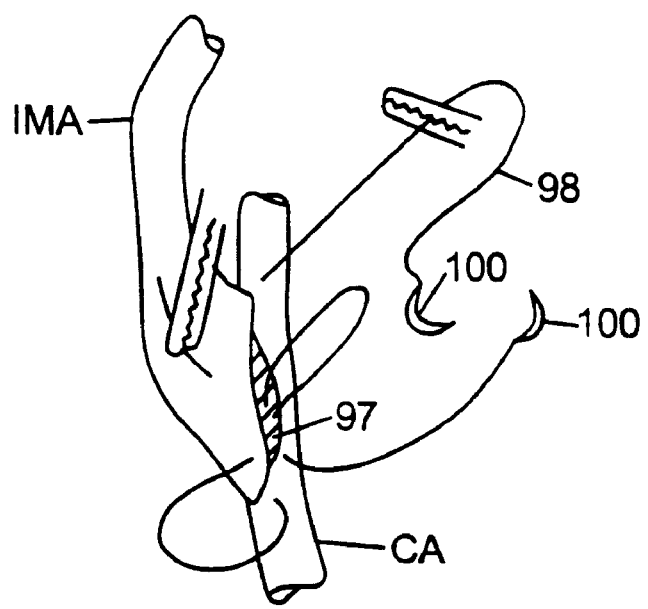
Figure 15:
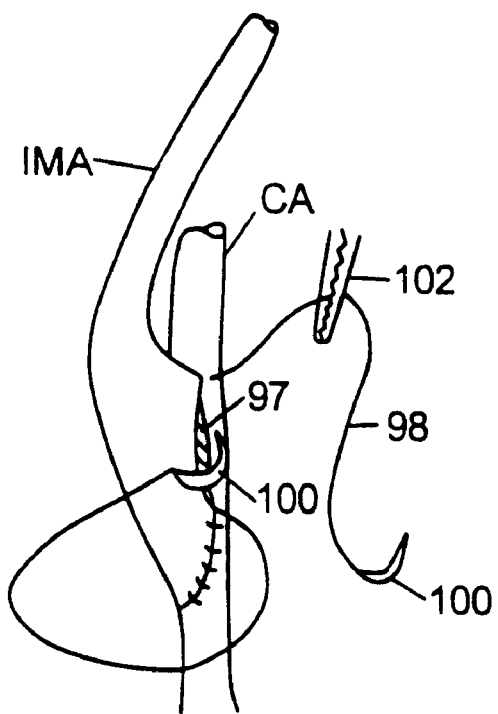

The configuration of this suture is especially advantageous for use in the port-access surgical CABG procedure. The suture can be inserted into the thoracic cavity through an access port and manipulated using thoracoscopic needle drivers to sew the anastomosis and to tie the suture within the thoracic cavity. Standard sutures, which are normally much longer, are very difficult to manipulate within the closed chest, especially when tying the suture using thoracoscopic instruments. The short length of the suture allows the knots in the suture to be pulled tight within the confines of the thoracic cavity while grasping the needles with the needle drivers. The multifilament, expanded PTFE suture material is much easier to handle and tie within the confines of the thoracic cavity than monofilament suture material which is generally stiffer and harder to handle. Additionally, the multifilament, expanded PTFE suture material has more resistance to damage than monofilament when it is grasped directly by the needle drivers, as shown in FIGS. 11, 14 and 15.

Figure 16:
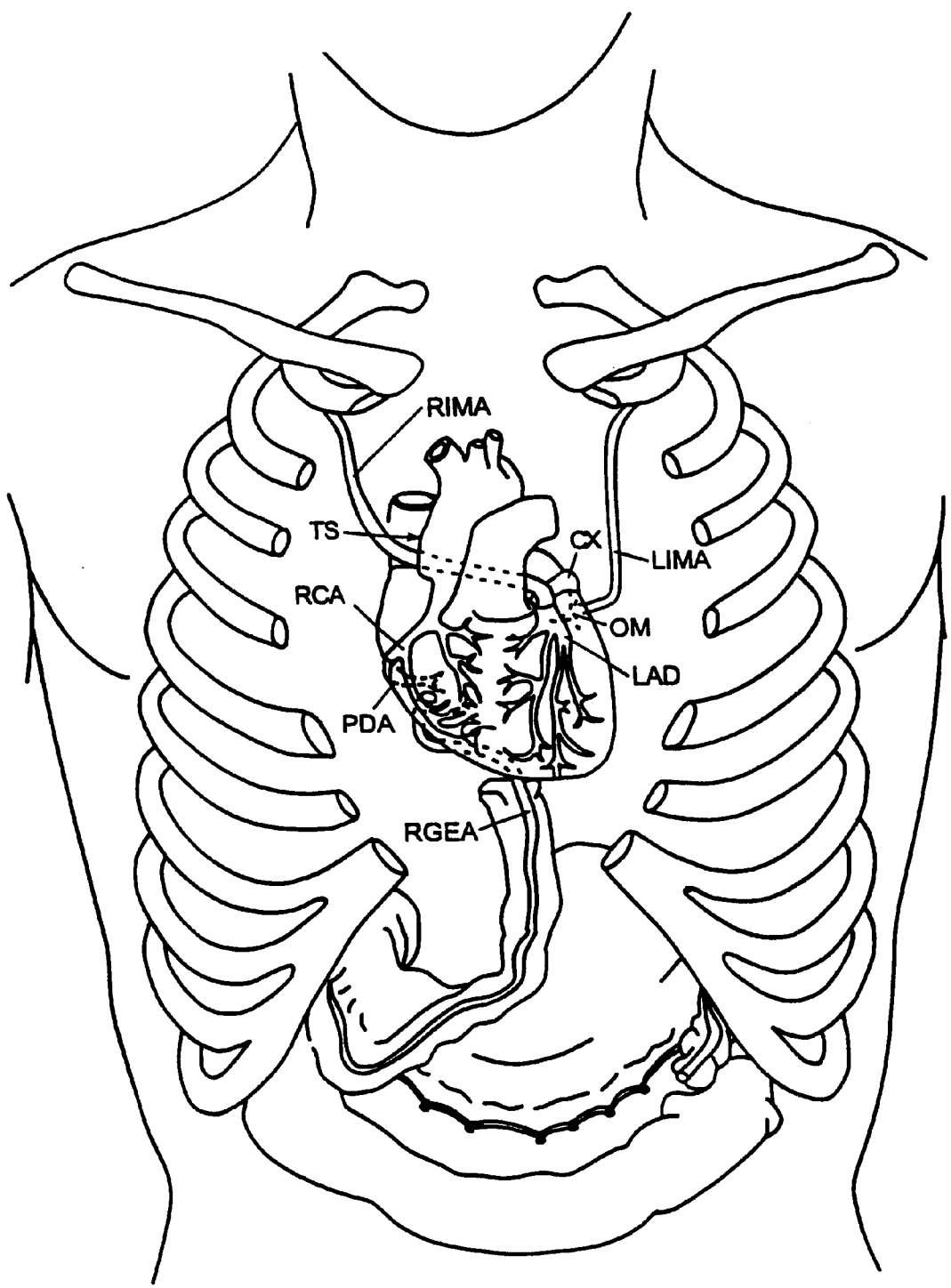
FIG. 16 shows the heart of the patient with multiple completed bypass grafts.

FIG. 16 shows the heart H of a patient after completion of a total revascularization for multivessel coronary artery disease using port-access techniques. Three bypass grafts have been made, using the LIMA as a bypass to one of the OM branches of the Cx, the RIMA as a bypass to the LAD, tunneled via the transverse sinus TS, and the RGEA as a bypass to the PDA, tunneled through the diaphragm.

Figure 19:
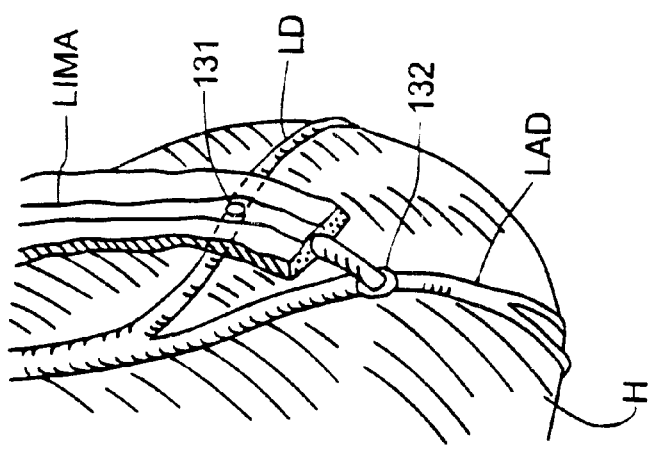
FIG. 19 shows the heart of the patient with sequential anastomoses on a "skip graft".
Figure 18:
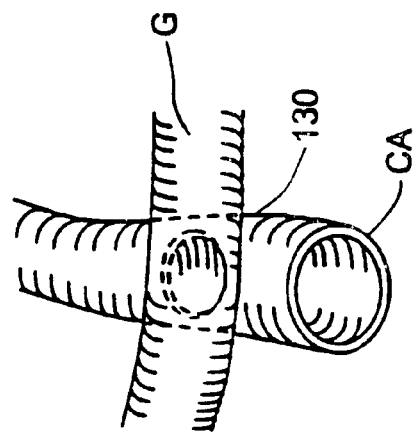
FIGS. 17–18 show the step-by-step sequence of creating a side-to-side anastomosis.
Figure 17:
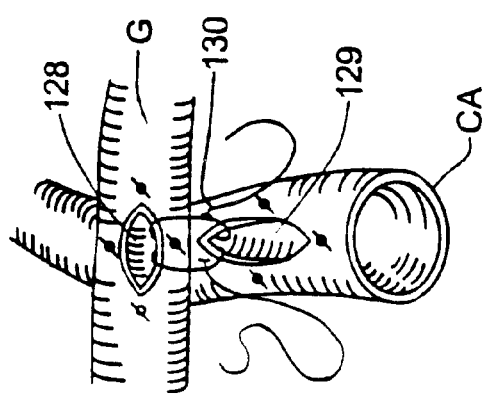

A sequential grafting technique or "skip grafting" is useful for achieving total revascularization when the number of significant coronary artery stenoses exceeds the number of available graft conduits. Sequential grafts are created by making a side-to-side anastomosis with a first coronary artery at an intermediate point on the graft vessel, then an end-to-side anastomosis between the distal end of the graft vessel and a second coronary artery. FIGS. 17–18 show the step-by-step sequence of creating a side-to-side anastomosis between a graft vessel G and a coronary artery CA. The side-to-side anastomosis is fashioned in a diamond-shaped manner, placing the graft vessel arteriotomy 128 at right angles to the coronary arteriotomy 129. Small arteriotomies, 3–4 mm in length, are used and six to eight continuous stitches 130 are placed through the coronary artery CA and the graft vessel G. An interrupted suture technique can also be used. FIG. 19 shows the heart H of a patient with a completed sequential graft. The LIMA has been first grafted to the diagonal branch LD of the left anterior descending coronary artery using a side-to-side anastomosis 131, then grafted to the LAD with an end-to-side anastomosis 132.

Figure 20:
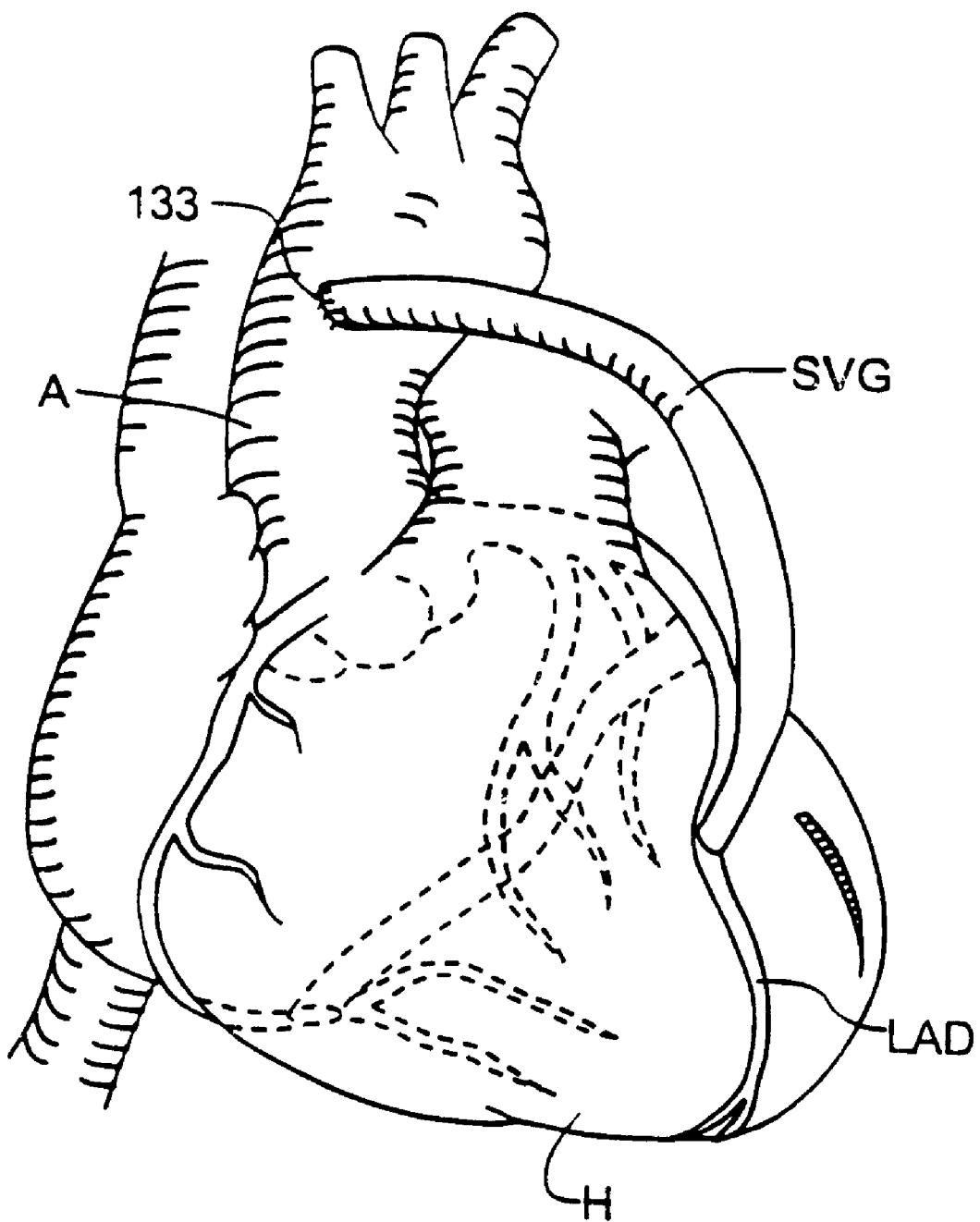
FIG. 20 shows the heart of the patient with a saphenous vein bypass graft.

Free grafts using either arterial conduits or venous conduits can be used to augment the in situ arterial grafts. Generally, the proximal end of a free grafts is anastomosed to the ascending aorta A to provide an arterial blood source and the distal end of the graft is anastomosed to one of the coronary arteries. A common source of free grafts is the greater saphenous vein. Other conduits used as free grafts include the lesser saphenous vein, the LIMA, the RIMA, the inferior epigastric artery, the splenic artery, the subclavian artery, and others. FIG. 20 shows the heart H of a patient with a saphenous vein bypass graft SVG to the LAD. The proximal anastomosis 133 can be created using suture techniques similar to those described in connection with FIGS. 10–15 above with the exception that a thoracoscopic tissue punch would be used to create an aortotomy after the initial incision with a scalpel. Alternatively, the proximal anastomosis 133 can be created using an anastomosis staple device, such as those described in co-owned, copending patent application Ser. No. 08/394,333, filed Feb. 24, 1995, the entire disclosure of which is hereby incorporated by reference.

Figure 21:
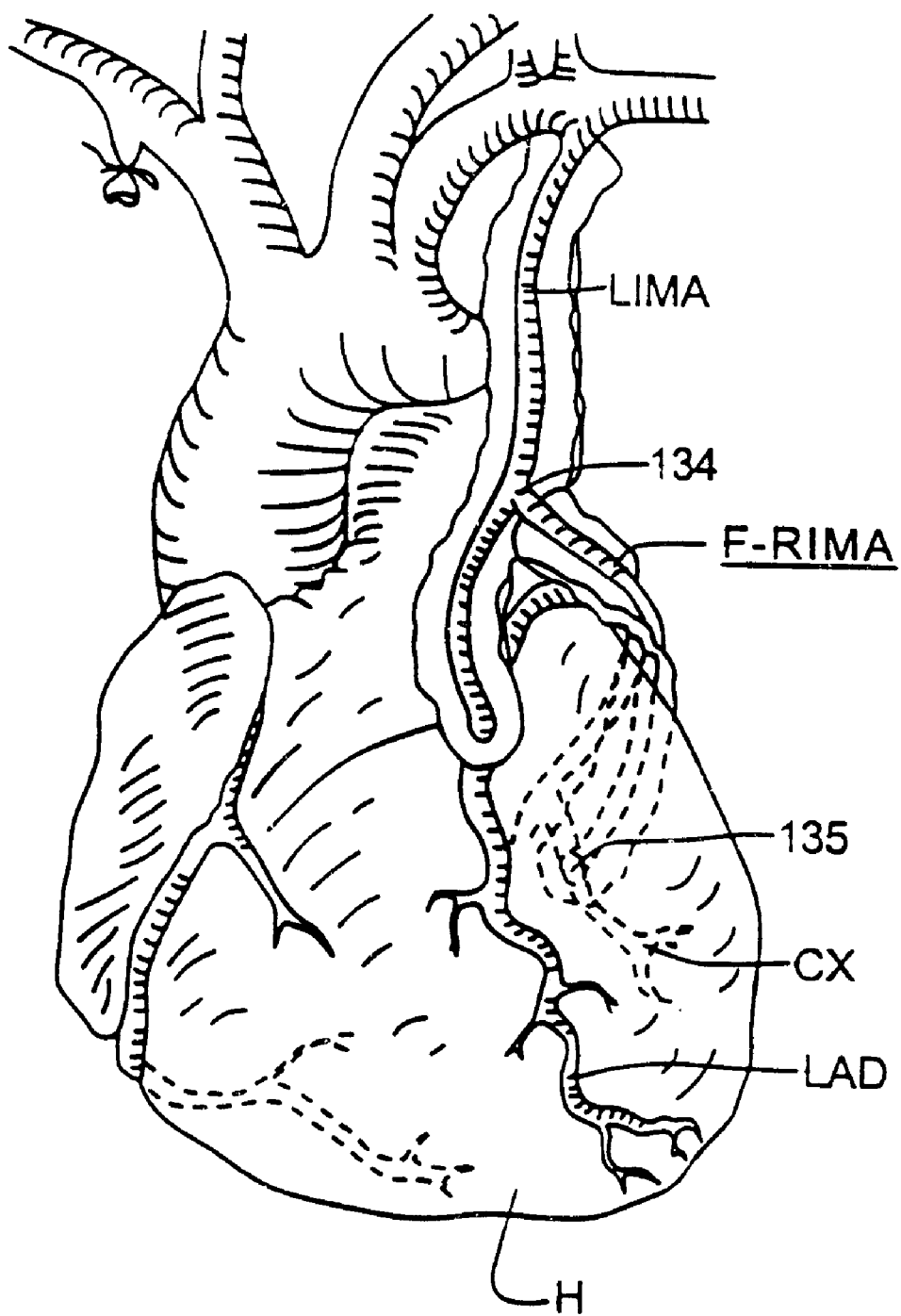
FIG. 21 shows the heart of the patient with a Y-graft.

Free grafts can be combined with in situ grafts or other free grafts to create composite bypass grafts to help achieve total revascularization for multivessel disease. For example, a free graft can be anastomosed to the distal end of an in situ graft like the LIMA or RIMA when there is insufficient length of the graft after takedown. Alternatively, a Y-graft can be created as an alternative to the sequential grafts described above. FIG. 21 shows the heart H of a patient with a Y-graft. The Y-graft was created by joining the proximal end of a free right internal mammary artery graft F-RIMA to an intermediate point on a LIMA in situ graft with an end-to-side anastomosis 134, then grafting the distal end of the RIMA to the Cx with an end-to-side anastomosis 135 and grafting the distal end of the LIMA to the LAD with an end-to-side anastomosis 136. Other conduits including arterial and venous grafts can be combined in various combinations to create composite grafts.

Instrument Descriptions

Figure 22:
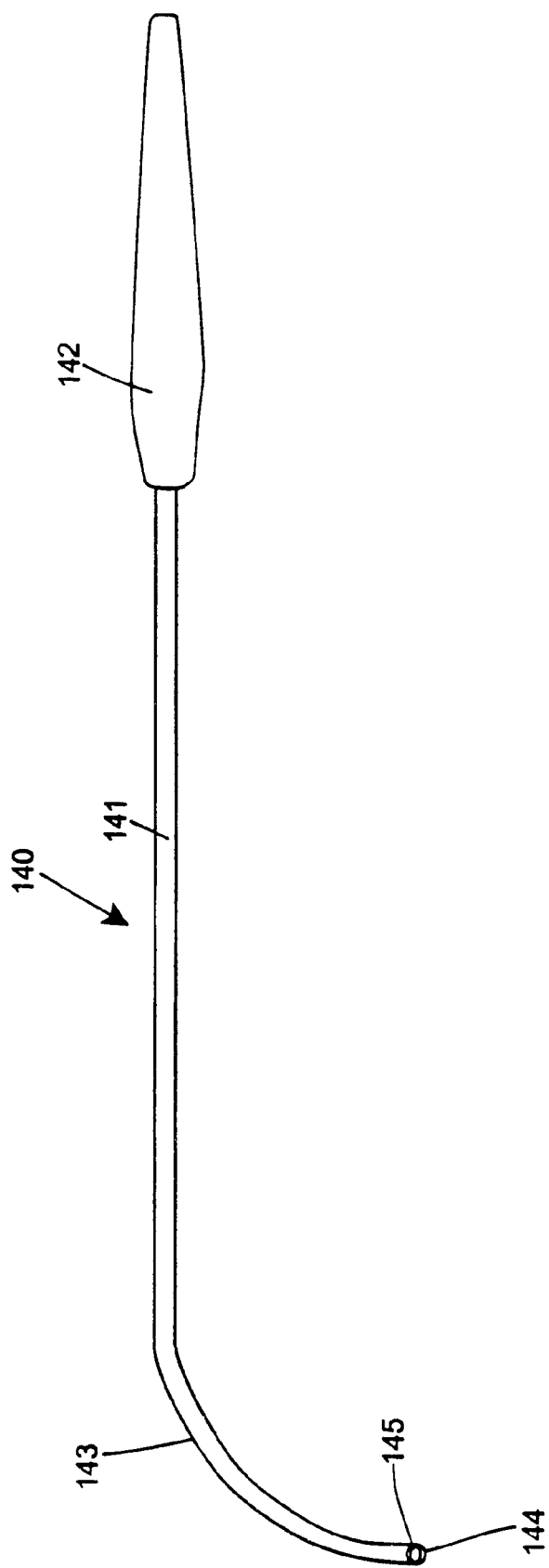
FIG. 22 shows a first embodiment of a tunneler for retracting the pulmonary trunk away from the transverse sinus.
Figure 23:
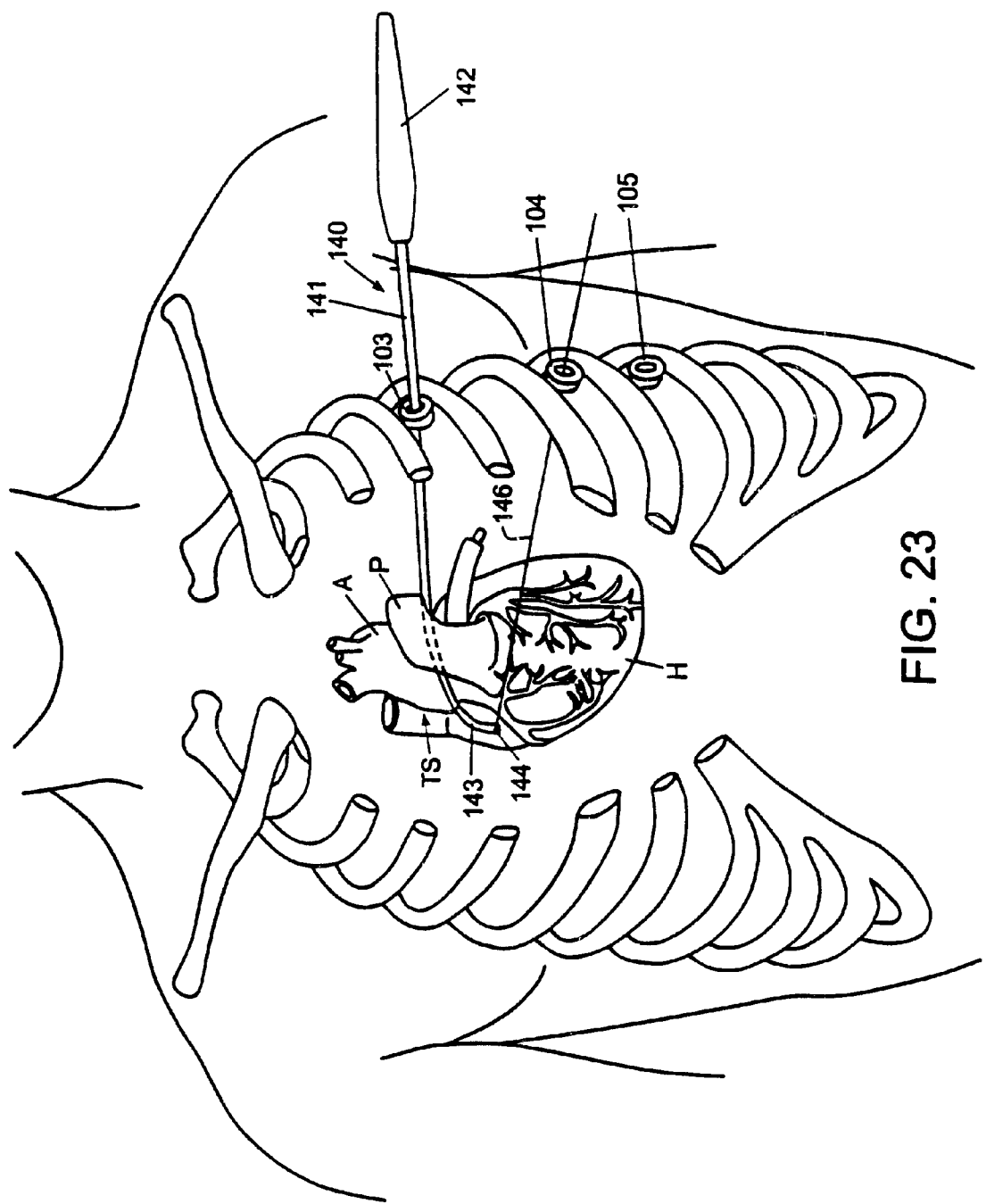
FIG. 23 shows a schematic diagram of a patient's heart with the tunneler of FIG. 22 in use.

FIGS. 22–47 show an armamentarium of instruments for facilitating the port-access multivessel CABG procedure. FIG. 22 shows a first embodiment of a tunneler 140 for retracting the pulmonary artery away from the ascending aorta to facilitate tunneling the RIMA through the transverse sinus TS. The tunneler 140 has an elongated shaft 141 of sufficient length to reach the great vessels of the heart from the takedown ports in the left lateral side of the chest, typically 15–30 cm in overall length. There is a handle 142 on the proximal end of the shaft 141. The distal portion 143 of the shaft is curved to facilitate passing the tunneler 140 through the transverse sinus TS from the left side of the heart. The distal tip 144 of the shaft is rounded to make it atraumatic. There is a hole 145 through the shaft 141 near the distal tip 144 of the tunneler 140. In use, a silastic tape 146 or elastomeric tube is threaded through the hole 145 and the distal end of the tunneler is inserted through one of the takedown ports (e.g. 103 in FIG. 23). Under thoracoscope observation, the curved distal portion 143 is inserted behind the pulmonary artery P and the ascending aorta A and passed through the transverse sinus TS to the right side of the heart, as shown in FIG. 23. When the distal tip 144 of the tunneler 140 emerges on the right side of the heart H, a grasper is inserted through one of the access ports, typically one of the takedown ports on the left lateral side of the chest, to grasp one side of the tape 146. The retractor 140 is withdrawn and the ends of the tape 146 are passed out through the access ports, preferably one of the takedown ports located at the third or fourth intercostal space, and tension is placed on the tape 140 to retract the main pulmonary artery P and the ascending aorta A (the aorto-pulmonary trunk), thereby widening the transverse sinus TS. With the pulmonary artery P and the ascending aorta A retracted, a grasping instrument, such as the articulated tunneling grasper 150 of FIG. 26, can more easily be reached through the transverse sinus TS.

Figures 24, 25:
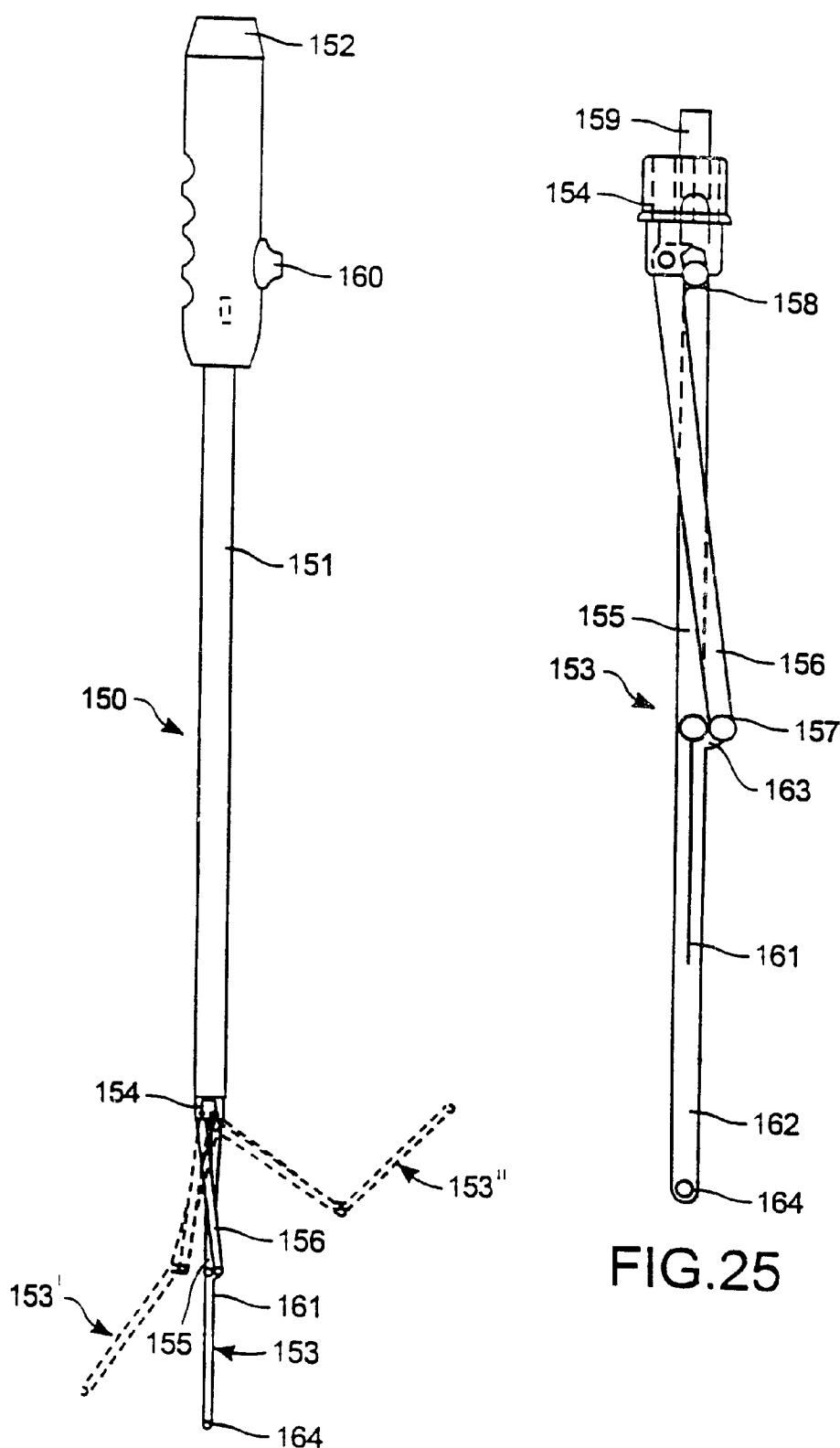
FIG. 24 shows a second embodiment of a tunneler having an articulating distal end.
FIG. 25 is an enlarged detail drawing of the multilink articulator on the distal end of the articulating tunneler of FIG. 24.

A basic embodiment of the articulated tunneling grasper 150 is shown in FIG. 24. The articulated tunneling grasper 150 has an elongated tubular shaft 151 with a handle 152 on the proximal end. A multilink articulator 153 is attached to the distal end of the shaft 151. The multilink articulator 153 is shown in detail in FIG. 25. The multilink articulator 153 has a head 154 which attaches to the distal end of the shaft 151. Two links 155, 156 are pivotally attached to the head 154. The first link 155 is a straight link. The proximal end of the first link 155 is pivotally attached to the head 154. The second link 156 is an L-shaped link with a long leg 157 that is approximately the same length as the first link 155, and a short leg 158 extending perpendicular from the proximal end of the long leg 157. The second link 156 is pivotally attached to the head 154 at the proximal end of the long leg 157. An actuator rod 159 that passes through the tubular shaft 151 connects the end of the short leg 158 with a sliding actuator button 160 on the handle 152. The first link 155 and the second link 156 cross one another and their distal ends are pivotally attached to a third link 161. The third link 161 is an L-shaped link with a long leg 162 extending distally, and a short leg 163 extending perpendicular from the proximal end of the long leg 162. When the actuator rod 159 is in its neutral position the multilink articulator 153 is in a relatively straight position, as shown in FIG. 24 by solid lines 153. When the actuator rod 159 is moved distally with respect to the head 154, it pivots the second link 156 clockwise, as shown in FIG. 24 by phantom lines 153'. The relative motion of the first 155 and second links 156, in turn, pivots the third link 161 clockwise, as shown. When the actuator rod 159 is moved proximally with respect to the head 154, it pivots the second link 156 counterclockwise, as shown in FIG. 24 by phantom lines 153". The relative motion of the first 155 and second links 156, in turn, pivots the third link 161 counterclockwise. The distal end of the multilink articulator 153 can thus pivot approximately 90 degrees in either direction.

Various end effectors can be attached to the distal end of the multilink articulator 153 for performing different tasks. The possible end effectors include a simple hole 164, as shown in FIG. 24, for placing a tape through the transverse sinus TS for retracting the aorto-pulmonary trunk, or a heart retraction device, such as a suction retractor or finger retractor, as discussed in more detail below, or a grasping mechanism, such as a cable-actuated grasper.

Figure 26:
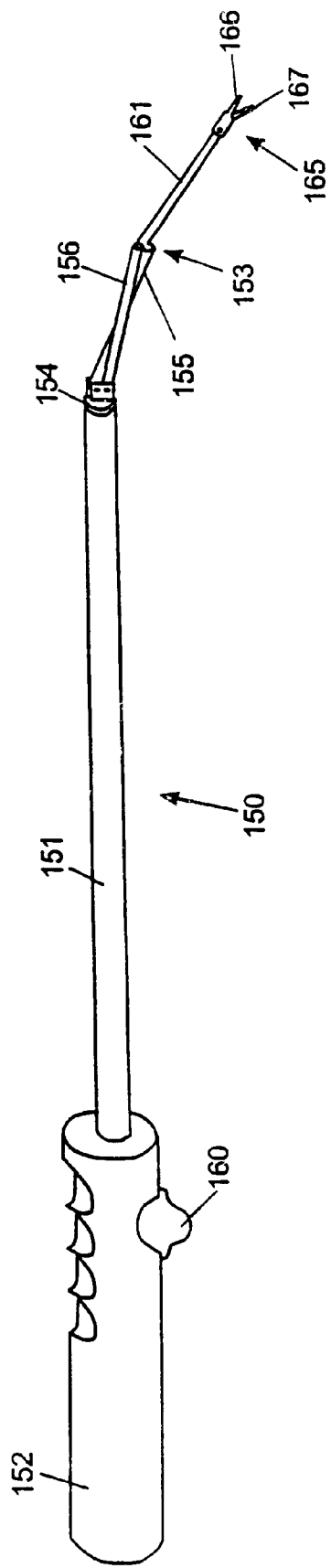
FIG. 26 shows an embodiment of the articulating tunneler of FIG. 24 with a grasper on the distal end for grasping the RIMA and drawing it through the transverse sinus.

In one particularly preferred embodiment, shown in FIG. 26, a cable-actuated grasper 165 is mounted on the distal end of the multilink articulator 153 shown in FIG. 24. The grasper 165 has a first 166 and second 167 jaw with grasping surfaces on the facing surfaces of the jaws 166, 167. At least one of the jaws 166, 167, and preferably both jaws, are pivotally attached to the distal end of the third link 166, 167. An actuator cable (not shown) extends from a control button 168 on the handle 152, through the tubular shaft, and to a linkage connected to the grasper jaws 166, 167. The jaws of the grasper 166, 167 can be actuated to open and close using the control button 168.

Figure 27:
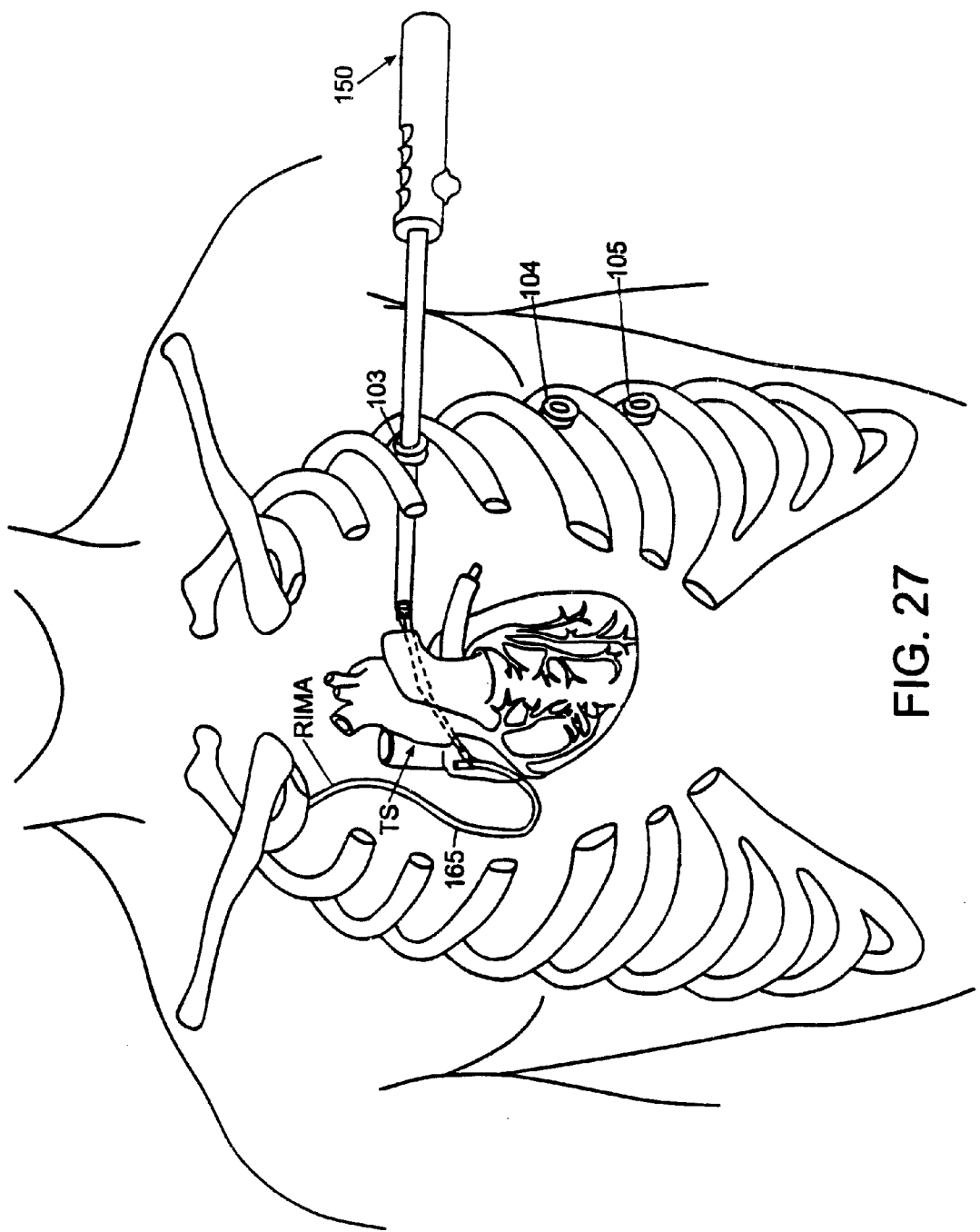
FIG. 27 shows a schematic diagram of a patient's heart with the articulating tunneler of FIG. 26 in use.

In use, the articulated tunneling grasper 150 is inserted through one of the takedown ports 103, 104, 105 in a straight position. The distal end of the grasper 165 is inserted behind the pulmonary artery P and the ascending aorta A, and through the transverse sinus TS, as shown in FIG. 27. The multilink articulator 153 is actuated to assume an appropriate curve to pass easily through the transverse sinus TS. Once the distal end of the grasper 165 emerges from the transverse sinus TS on the right side of the heart H, as shown in FIG. 27, the multilink actuator 153 can be used to manipulate the grasper 165 closer to the RIMA. Another grasper may be inserted through another access port to assist with handling the RIMA to the articulated tunneling grasper 150. The grasper 165 is opened, then closed to grasp the pedicle of the RIMA so as not to damage the vessel. The articulated tunneling grasper 150, with the RIMA in its grasp, is withdrawn through the transverse sinus TS to the left side of the heart H. The RIMA has thus been tunneled through the transverse sinus TS from the right side of the heart to the left side, as discussed above in relation to FIG. 2.

Tunneling the RIMA through the transverse sinus TS from the right side of the heart to the left side is the currently preferred path for rerouting the RIMA for attachment to the Cx or the OM branches. Alternatively, the RIMA can be routed across the anterior side of the heart using the articulated tunneler or another thoracoscopic grasping device. When rerouting a graft vessel, particularly when tunneling through a space such as the transverse sinus TS, it is important to avoid twisting or kinking the graft vessel. One way to avoid twisting the vessel is to mark a line along the vessel which can serve as an indicator of whether the vessel is straight. For instance, the vessel can be marked by drawing a line along the vessel or on the pedicle with a surgical marker containing a nontoxic ink, such as methylene blue. The vessel is preferably marked before takedown to assure that the vessel is in a straight condition when it is marked. Alternatively, the clips or sutures that are used to ligate side branches of the vessel during takedown can be used as markers to determine if the graft vessel is straight when it is rerouted.

Figure 28:
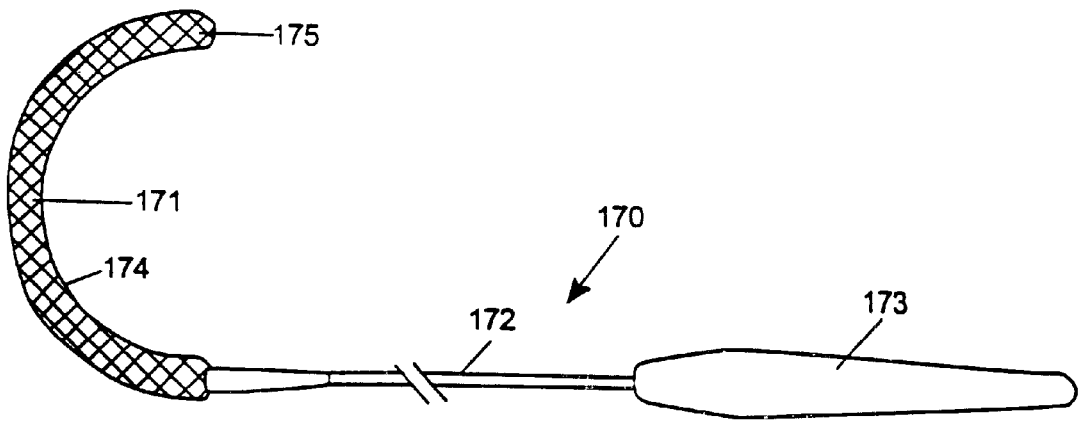
FIG. 28 shows a first embodiment of a heart retractor with a finger-like manipulator on the distal end.
Figure 29:
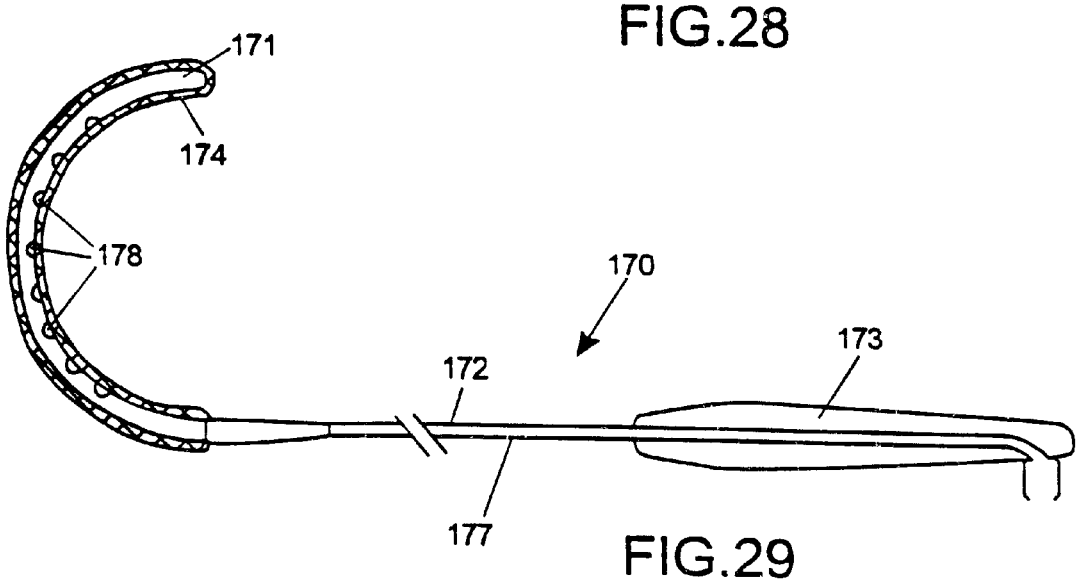
FIG. 29 shows an alternate embodiment of a heart retractor having a finger-like manipulator combined with a suction irrigation lumen.

FIG. 28 shows a first embodiment of a heart retractor 170 with a finger-like manipulator 171 on the distal end for rotating the heart within the closed chest of the patient to expose each of the coronary arteries to be anastomosed. The retractor 170 has an elongated shaft 172 of approximately 15–30 cm with a handle 173 on the proximal end of the shaft. The distal end of the retractor shaft is curved to create a finger-like manipulator 171. The curved manipulator 171 has a radius of curvature in one preferred embodiment of approximately 4.5 cm. The radius of curvature in other embodiment can range from 3.5–6 cm. The curvature of the finger-like manipulator 171 subtends an arc of approximately 90 to 180 degrees. The finger-like manipulator 171 has an outer diameter of approximately 5–10 mm. The finger-like manipulator 171 is preferably molded of a rigid plastic, such as ABS or nylon. Alternatively, the finger-like manipulator 171 can be made of metal, such as stainless steel. In one particular alternative embodiment, the finger-like manipulator 171 is made of annealed 316 stainless steel which is malleable so that it can be manually bent to the desired curvature. The exterior of the finger-like manipulator 171 is covered with an absorbent and/or high friction material 174 to assist in grasping and manipulating the heart. The covering 174 of the finger-like manipulator 174 extends to the very distal end 175 of the manipulator 171 and covers the rounded distal tip 175. The preferred material 174 for covering the finger-like manipulator 171 is a nonwoven polyester fabric, embossed with an open mesh pattern. The nonwoven polyester gives the covering absorbancy, while the open mesh pattern improves the friction of the surface. A fabric with a self-sticking adhesive surface is preferred for convenience in assembling the retractor. The currently preferred material for the covering 174 of the finger-like manipulator 171 is a 2.4 oz. nonwoven, embossed polyester medical tape with Wetstick™ adhesive available from Avery Dennison, Specialty Tape Division, Painesville, Ohio.

Alternate materials for the covering 174 of the finger-like manipulator 171 include nonembossed, nonwoven fabrics, such as polyester surgical felt. While the absorbancy of these materials is quite acceptable, the friction of the smooth, nonembossed fabric is less than for embossed materials. Examples of acceptable materials in this category include Fastsorb 820 and Exsorbx 400 available from Berkshire Corp, Great Barrington, Mass. or Surgical Felt 6077 or 6079 available from BARD, Vascular Surgery Division, Haverhill, Mass. Other materials suitable for covering the finger-like manipulator 171 include woven materials and knit materials made of polyester, cotton or other fibers. These materials also tend to have a lower coefficient of friction for gripping tissue. Another alternate material for the covering of the finger-like manipulator 171 is a composite material, including a first layer of a highly absorbent material, like surgical felt, and a second layer of mesh-like material to increasing the coefficient of friction for gripping the surface of the heart.

Figure 30:
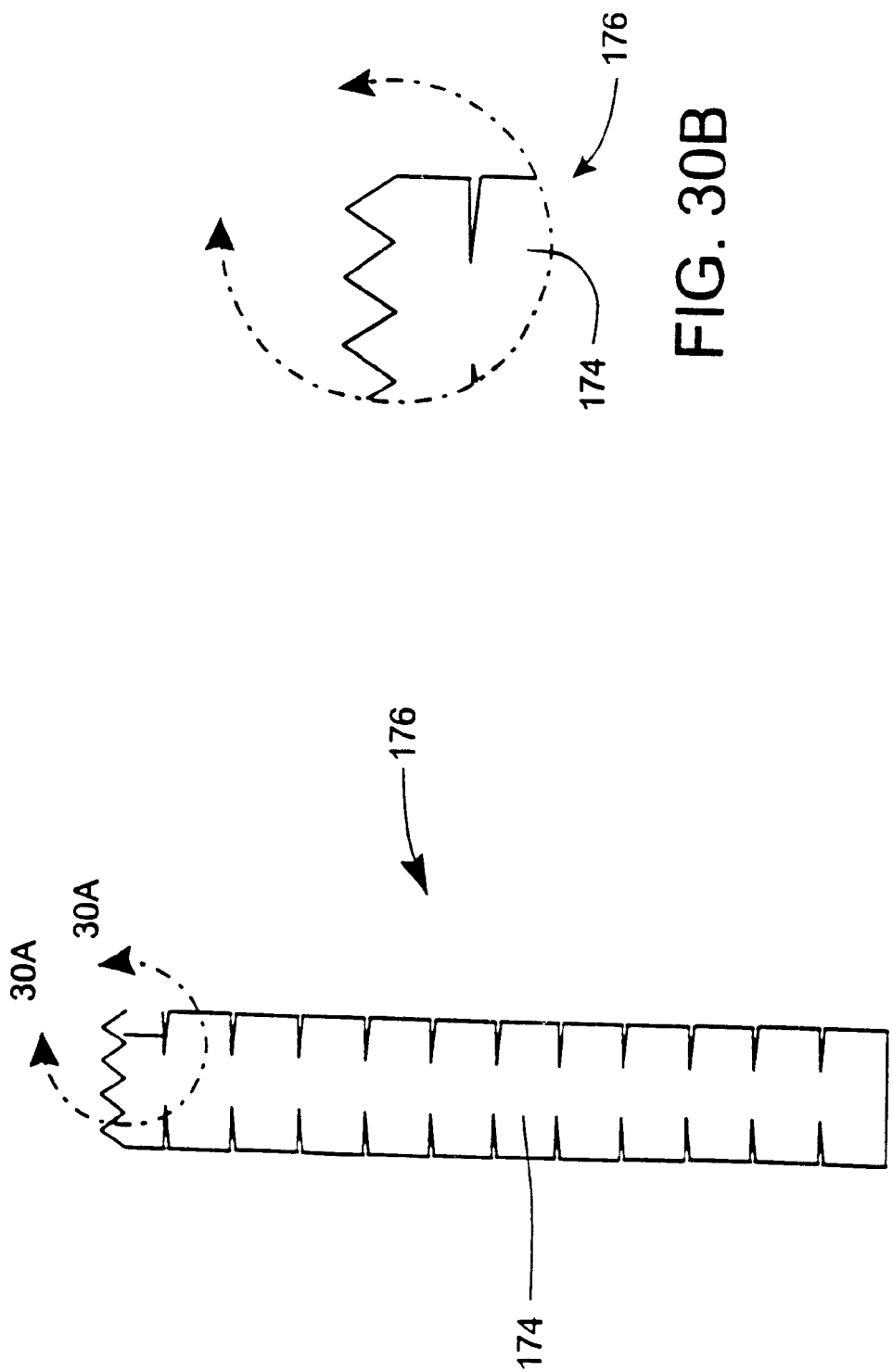
FIG. 30A shows a die-cutting pattern for the covering material to cover the finger-like manipulator of FIG. 28.
FIG. 30B shows an enlarged detail drawing of the die-cutting pattern of FIG. 30A.

The covering material 174 is preferably die cut in a pattern that easily conforms to the shape of the finger-like manipulator 171. FIG. 30 shows a die-cutting pattern 176 for the covering material 174 to cover a finger-like manipulator 171 having a radius of curvature of 4.5 cm which subtends 180 degrees of arc, and an outer diameter of 8 mm, such as the one shown in FIG. 28. FIG. 30B shows an enlarged detail drawing of the die-cutting pattern 176 of FIG. 30A. The self-adhesive covering material 174 is cut to this pattern 176 and adhesively bonded to the exterior of the finger-like manipulator 171.

The absorbancy, combined with the texture of the covering 174, gives the retractor 170 a good frictional grip on the surface of the heart. Keeping the interface between the retractor surface and the surface of the heart dry is important for maintaining a good frictional grip. Another preferred embodiment of the retractor 170, shown in FIG. 29, combines suction irrigation with the retractor to augment the absorbancy of the covering material 174. In this embodiment, a suction lumen 177 extends through the shaft 172 of the retractor 170 and through the finger-like manipulator 171. A series of suction holes 178 connect the suction lumen with the surface of the finger-like manipulator 171 on the inner curve of the distal end. A constant or intermittent suction through the holes 178 will keep the covering material 174 dry to improve the frictional grip on the surface of the heart.

Figure 31:
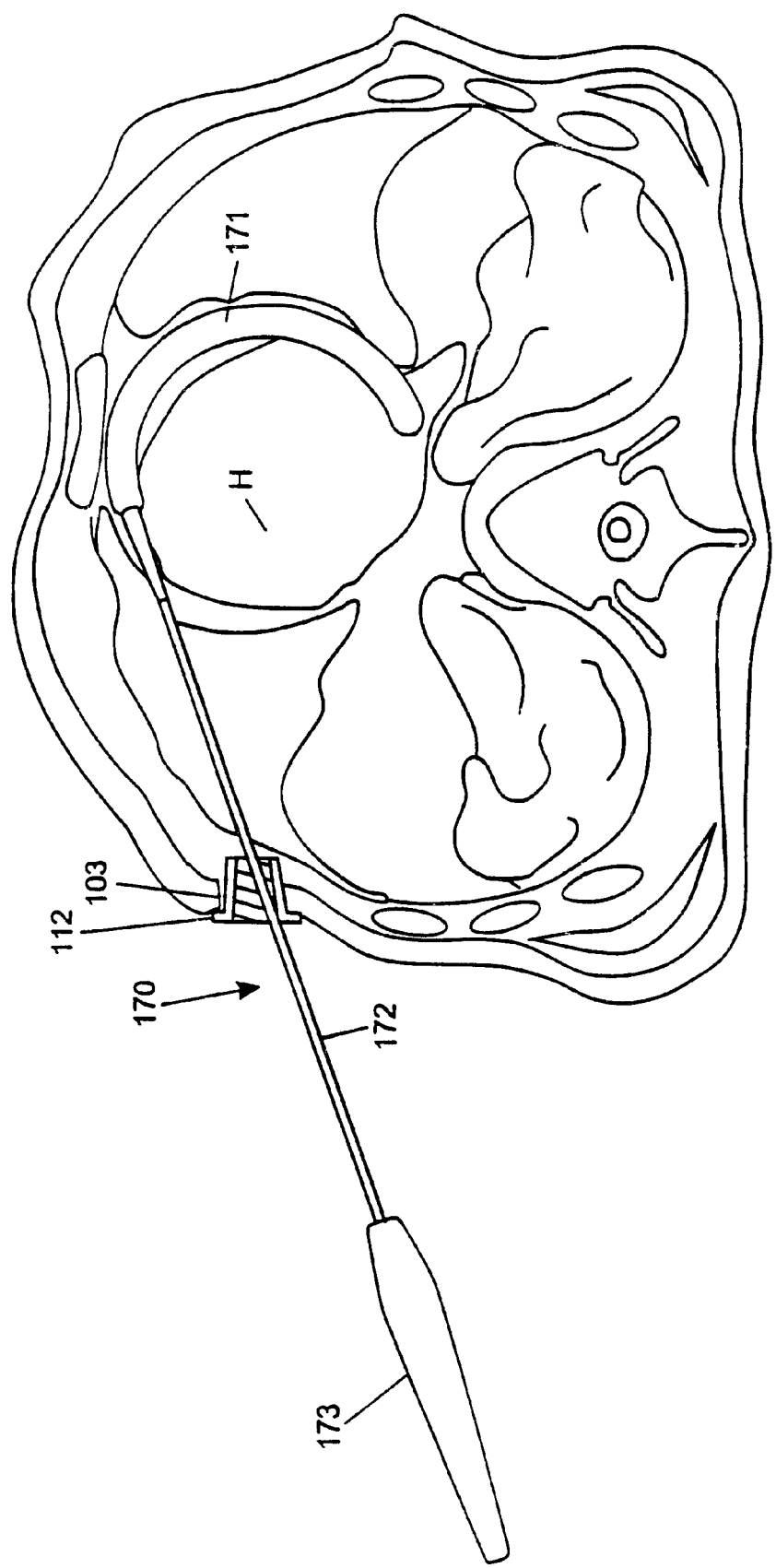
FIG. 31 shows a cross section of a patient showing the heart retractor of FIG. 28 in use.

In use, the retractor 170 is typically inserted into the thoracic cavity through one of the takedown ports 103, 104, 105 on the left lateral side of the chest. The curved finger-like manipulator 171 of the retractor 170 is hooked around the apex of the heart H, as shown in FIG. 31. The retractor 170 can be used to rotate or translate the position of the heart H within the closed chest. For example, the retractor 170 can be used to roll the heart H toward the right side of the patient to expose the Cx or the OM branches on the left aspect of the heart to the microscope in the visualization port 120. This position of the heart H is shown in FIG. 7. The retractor 170 can also be used to lift the apex of the heart and flip the heart 180 degrees to expose the RCA or PDA on the posterior aspect of the heart H to view. This position of the heart H is shown in FIG. 9.

Figure 32:
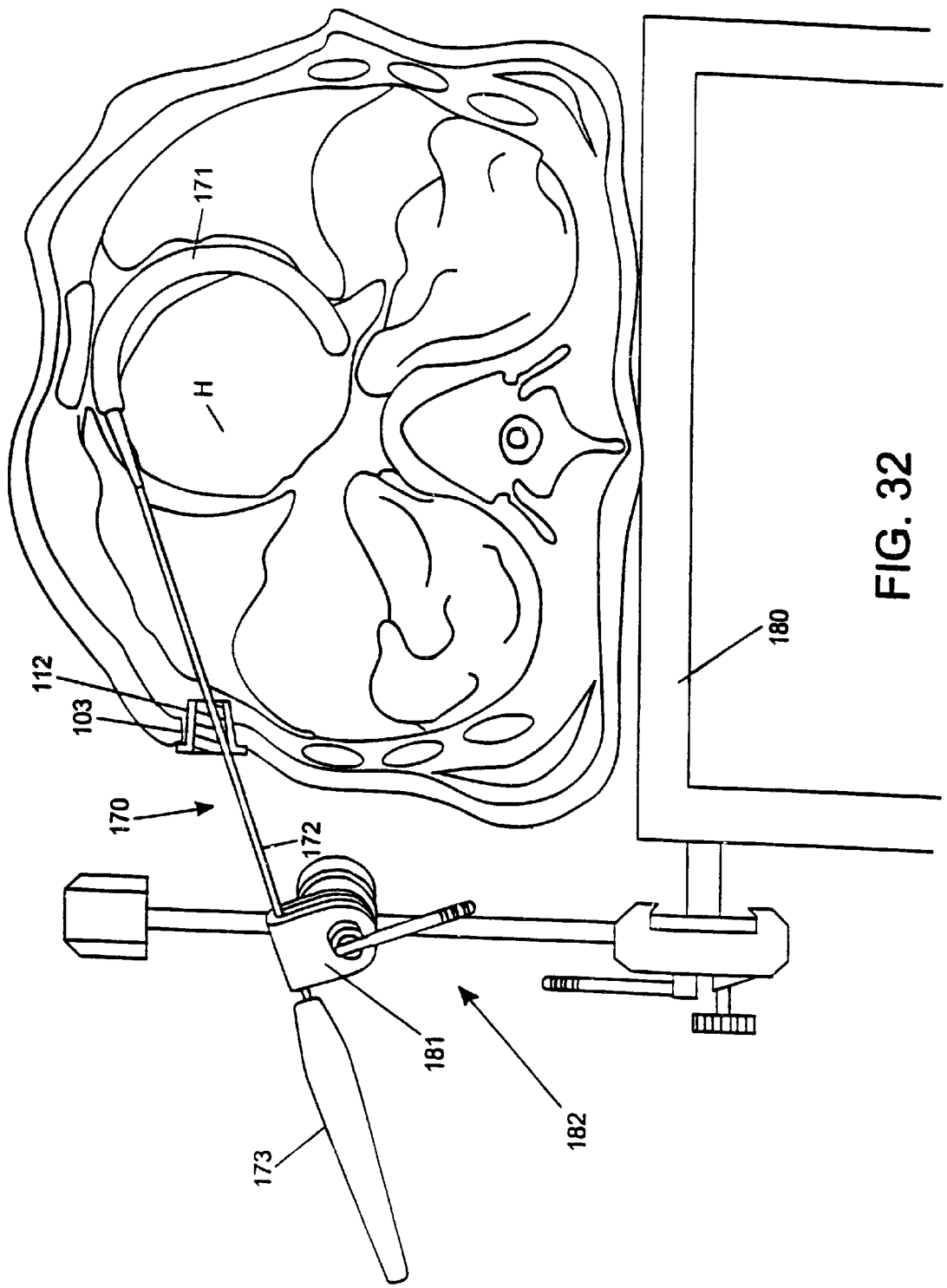
FIG. 32 shows the heart retractor of FIG. 28 fixed to the operating table to stabilize the heart.

The retractor 170 can be fixed to the operating table 180 to stabilize the heart H in the desired position, as shown in FIG. 32. A positioning device 182, such as those available from Omni-Tract Surgical Div., Minneapolis, Minn. or Mediflex Medical Products, Islandia, N.Y., is attached to the operating table 180 and bent to the correct position and locked in place. A clamp 181 on the distal end of the positioning device 182 is attached to the proximal end of the retractor 180 to hold it in place and maintain the position of the heart H during the course of the grafting step.

Figure 33A:
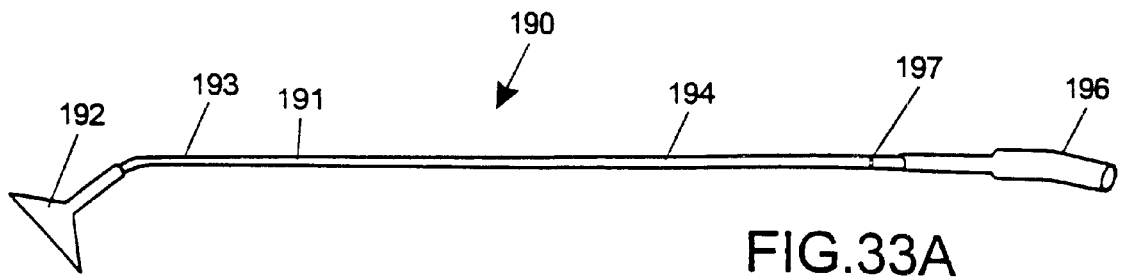
FIG. 33A shows a side view of a second embodiment of a heart retractor having a suction cup-shaped manipulator on the distal end.

FIG. 33A shows a side view of an embodiment of a suction heart retractor 190 for manipulating the heart within the closed chest of the patient. The retractor 190 has an elongated tubular shaft 191 having a suction cup-shaped manipulator 192 on the distal end. The suction cup-shaped manipulator 192 may be mounted straight on the shaft 191 or it may be mounted at an angle to the shaft 191. In one particularly preferred embodiment, there is a 45 degree bend 193 near the distal end of the shaft 191 so that the suction cup-shaped manipulator 192 is mounted at a 45 degree angle to the proximal shaft 191. In either embodiment, the suction cup-shaped manipulator 192 is preferably flexibly mounted to the distal end of the shaft 191. A vacuum lumen 194 extends through the tubular shaft from the proximal end to the distal end. The distal end of the vacuum lumen 194 is in fluid communication with the interior 195 of the suction cup-shaped manipulator 192. The proximal end of the vacuum lumen 194 is adapted for attachment to a vacuum source. A fitting for connecting to the vacuum source, such as a barb fitting or luer fitting, may be attached to the proximal end of the tubular shaft 191, or a flexible extension tube 196 may be attached to the proximal end of the shaft 191 with a fitting at the far end of the extension tube 196.

The shaft 191 of the retractor 190 is preferably made of a rigid material that will support the forces required for manipulating the heart without significant deformation. Acceptable materials for the retractor shaft include stainless steel and liquid crystal polymer. To facilitate forming an angled or curved shaft, a mineral filled liquid crystal polymer (e.g. calcium carbonate) is preferred. This material can be heat formed at 350 to 400 degrees F.

Figure 33B:
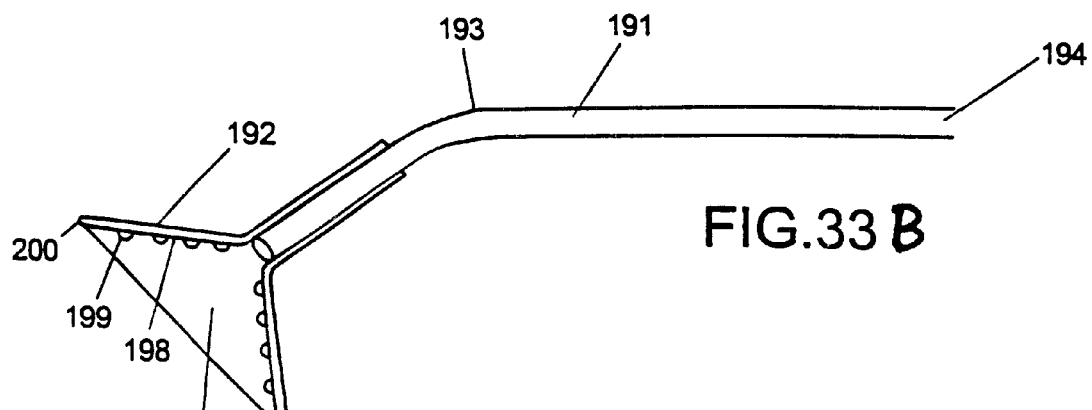
FIG. 33B shows a longitudinal cross section of the distal end of the heart retractor of FIG. 33A.
Figure 33C:
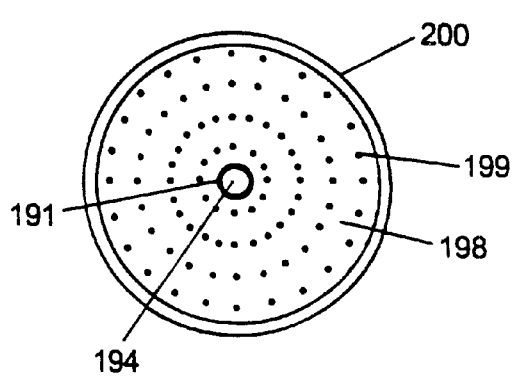
FIG. 33C shows a distal end view of the heart retractor of FIG. 33A.

FIG. 33B shows a longitudinal cross section of the distal end of the heart retractor 190 of FIG. 33A, and FIG. 33C shows a distal end view of the heart retractor of FIG. 33A. The suction cup-shaped manipulator 192 has an external diameter of approximately 12 to 50 mm for a surface area of approximately 110 to 1960 $mm^2$. The surface area of the suction cup-shaped manipulator 192 allows a firm grip on the surface of the heart H when a vacuum is applied to the interior 195 of the suction cup 192, without causing vacuum damage to the tissue. A valve 197 on the shaft 191 of the retractor 190 allows the surgeon to control the vacuum to turn it on and off. Preferably, the vacuum should be limited to a maximum of 150 mmHg to avoid tissue damage. The suction cup-shaped manipulator 192 is made of a soft, flexible elastomeric material, such as silicone rubber with a hardness of approximately 40 to 80 Shore A durometer. The soft, flexible suction cup-shaped manipulator 192 is designed so that when a vacuum is applied within the interior 195 of the suction cup 192, the suction cup 192 conforms to the surface of the heart H and does not cause deformation of the heart tissue.

The distal surface 198 of the suction cup-shaped manipulator 192 is textured to create a high friction surface. In one particularly preferred embodiment, the suction cup-shaped manipulator 192 has a pattern of bumps 199 on the distal surface 198 and a circular ridge 200 around the periphery of the suction cup 192. The bumps 199 in one preferred embodiment have a height of approximately 1 mm with a 120 degree conical end and straight sides. Other geometries for the friction-increasing bumps 199 include conical, cylindrical or hemispherical, as well as other possible geometries. The circular ridge 200 around the periphery has a height of approximately 1–2 mm. The geometry and the pattern of the bumps 199 create a reliable friction grip on the surface of the heart H under vacuum without causing any damage to the heart tissue. An alternative embodiment of the retractor has an absorbent high friction material (not shown) adhesively attached to or cast into the distal surface of the suction cup-shaped manipulator 192 in place of the pattern of bumps. A suitable absorbent high friction material for this application is a nonwoven polyester fabric embossed with an open mesh pattern.

Figure 34:
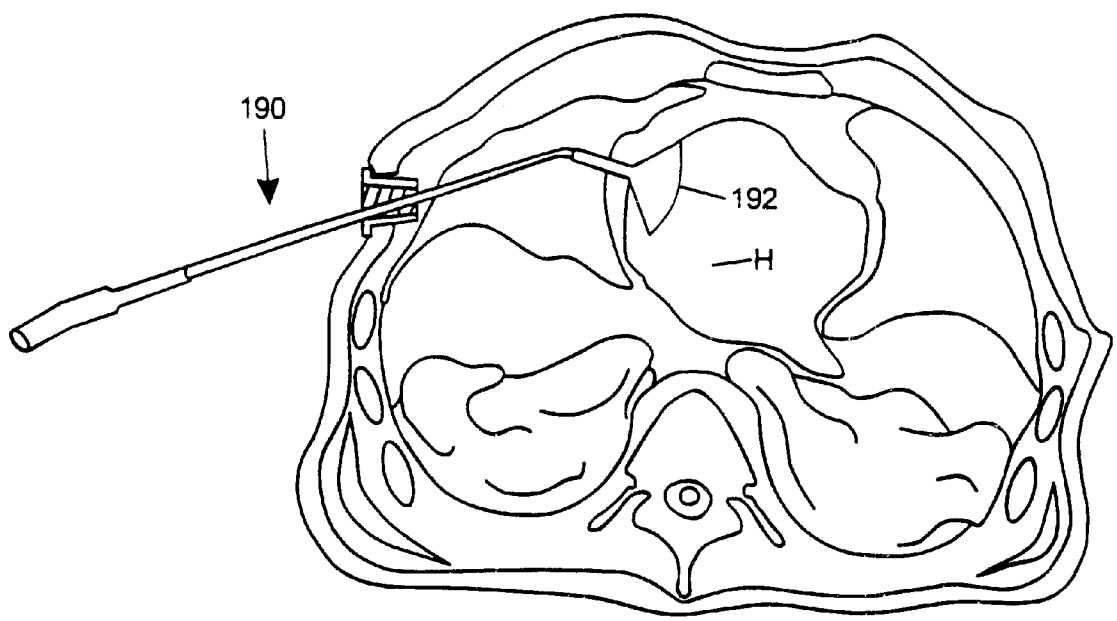
FIG. 34 shows a cross section of a patient showing the heart retractor of FIG. 33 in use.
Figure 35:
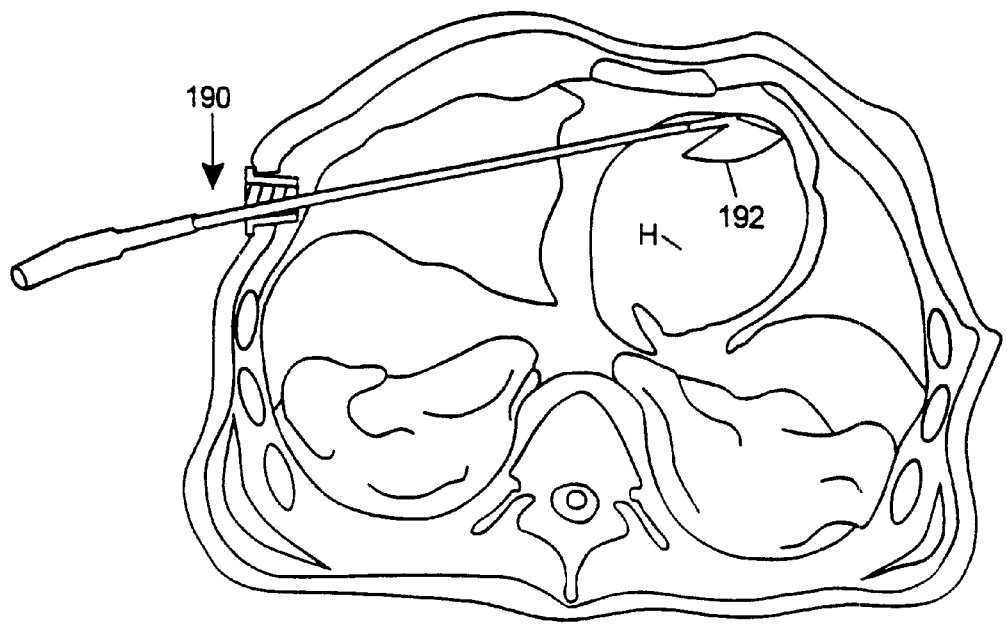
FIG. 35 shows the heart retractor of FIG. 33 used to rotate the heart to expose the Cx and the OM branches on the left aspect of the heart.

In use, the distal end of the retractor 190 is inserted through one of the access ports, typically one of the takedown ports 103, 104, 105 in the left lateral side of the patient's chest. The soft, flexible nature of the suction cup-shaped manipulator 192 allows it to be folded or collapsed as it is pushed through the access port. The retractor 190 can be inserted through an access cannula 112 or the cannula 112 can be removed from the access port 103 to facilitate insertion of the suction cup-shaped manipulator 192 directly through the access port 103. In one preferred embodiment of the method, suction cup-shaped manipulator 192 is placed on the anterior surface of the heart H near the apex, as shown in FIG. 34, and a vacuum is applied to grip the surface of the heart. From this position, the retractor 192 can be used to rotate the heart H in either direction. In FIG. 35, the retractor 190 has been used to rotate the heart H approximately 90 degrees to the right to expose the Cx and the OM branches on the left aspect of the heart to view. The retractor 190 can also be used to rotate the heart 180 degrees to the left to expose the RCA and PDA on the posterior aspect of the heart, as in FIG. 8. In an alternative embodiment of the method, the suction cup-shaped manipulator 192 is placed on the posterior side of the heart near the apex and a vacuum is applied to grip the surface of the heart. Then, the retractor 190 is used to lift and rotate the heart to flip it 180 degrees to expose the RCA and PDA on the posterior aspect of the heart, as in FIG. 7. This retractor 190 can also be fixed to the operating table to stabilize the heart in the desired position similarly to the embodiment of FIG. 32.

FIG. 36 shows a third retraction device 210 for manipulating the heart within a patient's closed chest. The retraction device 210 has an elongated tubular shaft 211. The tubular shaft 211 has a right angle bend 212 at the distal end. A first end 213 of a flexible snare 214 is attached to the shaft 211 at the distal end. The second end of the flexible snare extends through a lumen within the tubular shaft 211 and attaches to a sliding handle 215 at the proximal end. The snare 214 is made of a flexible wire or band. Preferably, the flexible wire or band is covered with a soft, flexible friction material to increase the surface area and to improve the frictional grip on the heart. Suitable materials for the covering of the snare include soft, flexible polymers or elastomers or absorbent, high-friction fabrics. The flexible wire or band 214 of the snare is preferably made of a highly resilient material such as a superelastic nickel/titanium alloy or a spring temper stainless steel or titanium alloy.

Figure 38:
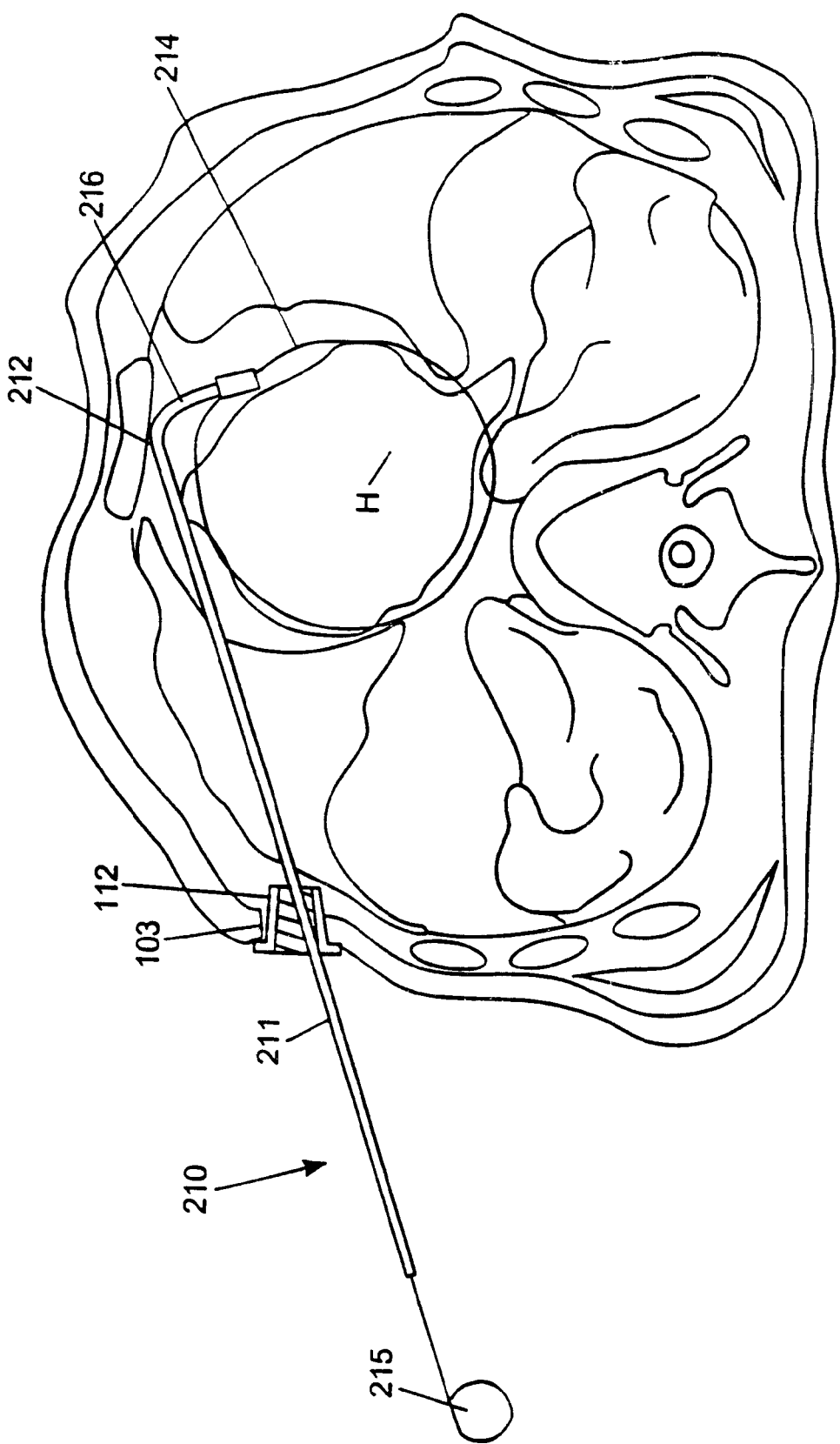
FIG. 38 shows a cross section of a patient showing the heart retractor of FIG. 36 in use.

FIG. 37 shows the heart retractor of FIG. 36 in a predeployed position for insertion through an access cannula. When the sliding handle is in a proximal position, the snare 214' forms a small loop, as shown in FIG. 37, which easily deforms to fit through a 10 mm access cannula. When the sliding handle 215 is in a distal position, the snare 215 forms a large loop 214, as shown in FIG. 36, which is large enough to encircle the heart H. The wire is preferably preshaped so that the snare opens up in a loop 214 perpendicular to the axis of the distal segment 216 of the shaft 211. FIG. 38 shows a cross section of a patient showing the retraction device 210 inserted into the thoracic cavity through one of the access ports 103 with the snare encircling the heart H. From this position, the retractor 210 can be used to manipulate the heart H to a desired position. For example, the retractor 210 can be used to lift and rotate the heart H to flip it 180 degrees to expose the RCA and PDA on the posterior aspect of the heart, as in FIG. 7.

FIG. 39 shows a fourth retractor device 220 for manipulating the heart within the close chest of a patient in a predeployed position for insertion through an access cannula. The retractor 220 has an elongated tubular shaft 221 with a handle 226 on the proximal end. In a preferred embodiment, the distal end 222 of the shaft has an angled portion at an approximately 0 to 45 degree angle to the proximal portion of the shaft 221. A flexible band 223 extends through a lumen within the tubular shaft 221 and extends beyond the distal end of the shaft 221. The distal end of the band 223 is pivotally attached to a distal link 224. The distal link 224 is, in turn, pivotally attached to a proximal link 225 which, in turn, is pivotally attached to the distal end 222 of the tubular shaft 221. The proximal end of the band 223 is attached to a sliding actuator button 227 on the handle 226. When the activator button 227 is in a proximal position, the distal portion of the flexible band 223 is positioned parallel to and in close proximity to be proximal 225 and distal links 224, as shown in FIG. 39. When the activator button 227 is in a distal position, the distal portion of the flexible band 223 extends from the distal end of the tubular shaft 221 to form a loop 228 together with the proximal 225 and distal links 224, as shown in FIG. 40. In the illustrative embodiment of FIGS. 39 and 40, the handle 226 has a semicircular cassette 229 for storage of the band 223 when the band is in the proximal position. Other embodiments of the retractor 220 could have a circular storage cassette or a linear configuration for storing the retracted band 221. Preferably, the flexible band 223 is made of a resilient material such as a spring tempered stainless steel or titanium alloy. The proximal 225 and distal links 224 are also preferably made of a stainless steel or titanium alloy. The surfaces of the flexible band 223 and/or the proximal 225 and distal links 224 facing the inside of the loop 229 are preferably covered with a soft, flexible friction material to improve the frictional grip a the retractor on the heart H. Suitable materials for the covering of the loop 228 include soft, flexible polymers or elastomers or absorbent, high-friction fabrics.

Figure 41:
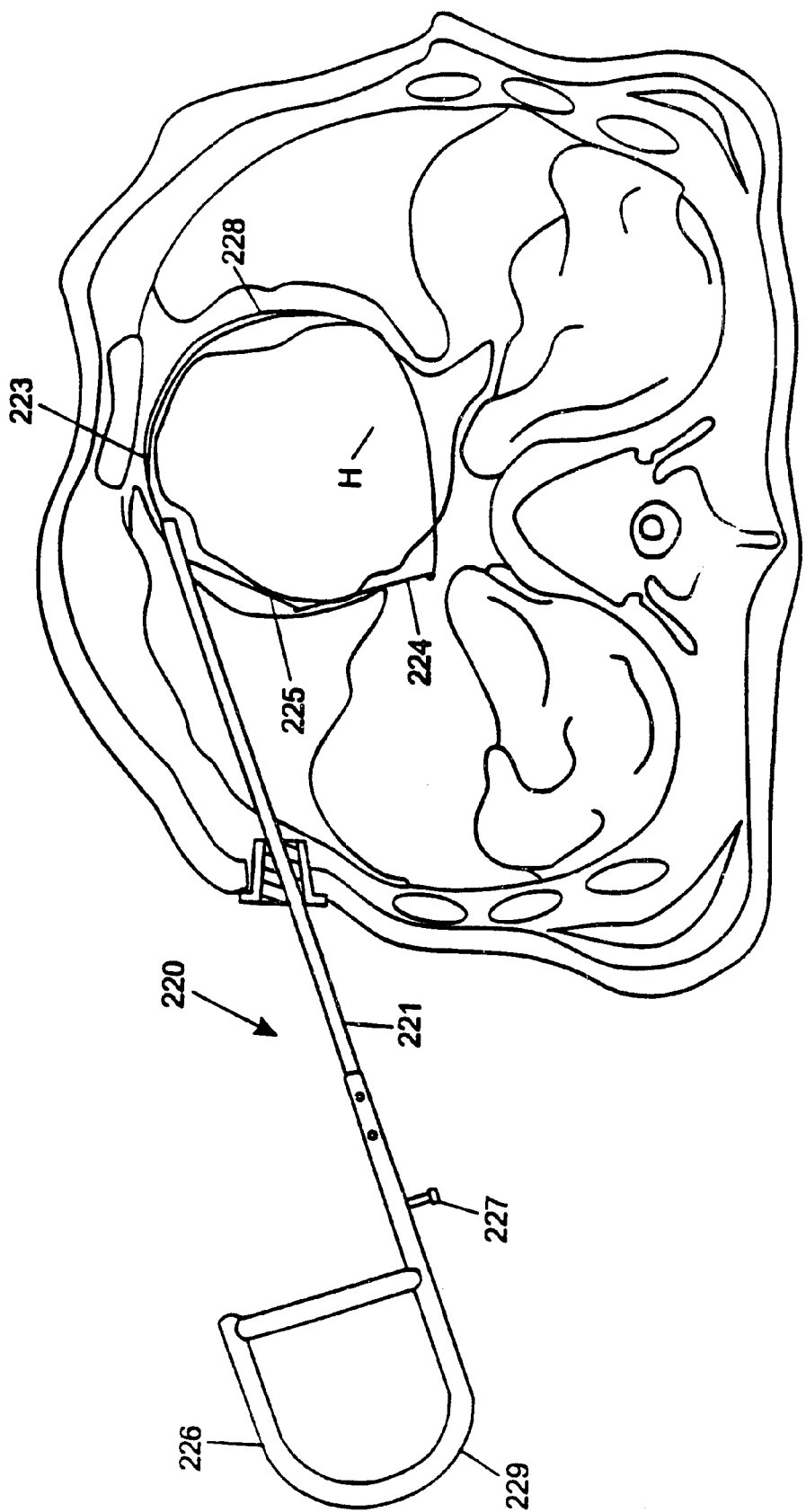
FIG. 41 shows a cross section of a patient showing the heart retractor of FIG. 39 in use.

In use, the distal end of the retractor loop 220 is inserted into the thoracic cavity through one of the access ports 103, typically one of the takedown ports 103, 104, 105 on the left lateral side of the chest. The actuator button 227 is advanced distally to open the loop 228 large enough to encircle the heart H. The loop 22 is passed around the heart H from the apex end and tightened gently around the heart, as shown in FIG. 41. A force limiter can be incorporated into the actuating mechanism of the retractor 220 to prevent excessive force on the heart H. From this position, the retractor 220 can be used to manipulate the heart H to a desired position. For example, the retractor 220 can be used to lift and rotate the heart to flip it 180 degrees to expose the RCA and PDA on the posterior aspect of the heart, as in FIG. 7.

FIGS. 42–45 show a topical hypothermia device 230 which can be used to improve myocardial protection during the port-access multivessel CABG procedure. The topical hypothermia device 230 has a flexible heat exchanger 231 which has at least one fluid passage 232 therethrough to circulate a cooling fluid. The flexible heat exchanger 231 is collapsible to a predeployed position which can easily fit through an access port into the chest of the patient. The flexible heat exchanger 231 is attached to the distal end of an elongated tubular shaft 233. The tubular shaft 233 is preferably made of a rigid material such as stainless steel or a rigid plastic. An inflow lumen 234 extends through the tubular shaft 233 and is fluidly connected to the flexible heat exchanger 231. A return lumen 235 extends through the tubular shaft 233 parallel to the inflow lumen 234. The inflow lumen 234 and the return lumen 235 may be formed of extruded plastic tubes which are inserted through the tubular shaft 233. Alternatively, the lumens 234, 235 may be formed integrally with the tubular shaft 233 by extrusion. The proximal ends of the inflow lumen 234 and the return lumen 235 are adapted for attachment to a circulating pump 236 and a reservoir of cooling fluid 237, which is preferably a saline solution.

Figure 42:
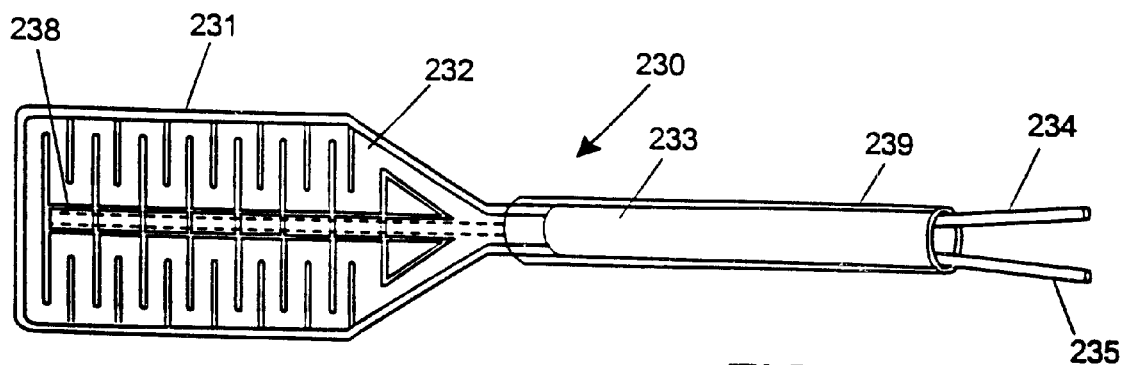
FIG. 42 shows a first embodiment of a topical hypothermia device for cooling a patients heart to improve myocardial protection during port-access cardiac surgery.
Figure 43:
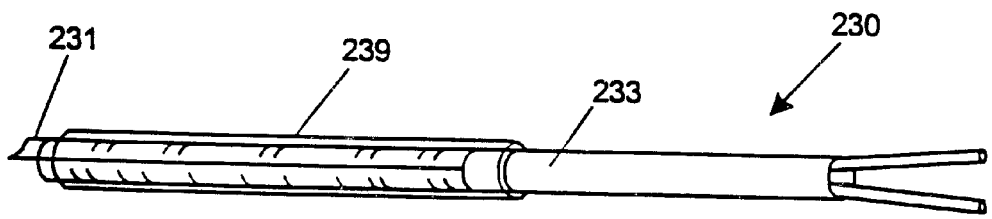
FIG. 43 shows the topical hypothermia device of FIG. 42 in a predeployed position for insertion through an access port.

In the illustrative embodiment of FIG. 42, the flexible heat exchanger 231 is made from two sheets of flexible plastic which are heat sealed or RF sealed together to form a serpentine cooling path 232 through the heat exchanger 231. Preferred materials for manufacturing the flexible heat exchanger 231 include polyurethane, vinyl, polypropylene, nylon, etc. The flexible heat exchanger 231, in one preferred embodiment, has a length of 12–18 cm and a width of 7–10 cm. Optionally, the flexible heat exchanger 231 may have a flexible backbone 238 which extends from the distal end of the tubular shaft 233 to the distal edge of the heat exchanger 231. The flexible backbone 238 may be made from a flexible polymer, elastomer, or a resilient metal wire, such as spring temper stainless steel or a superelastic nickel/titanium alloy, or a composite of metal and plastic. The flexible heat exchanger 231 is rolled, folded or twisted and placed in an introducer sheath 239 in the predeployed position as shown in FIG. 43. Preferably, the introducer sheath 239 is sized to fit through an access cannula with a 10–12 mm internal diameter.

Figure 44:
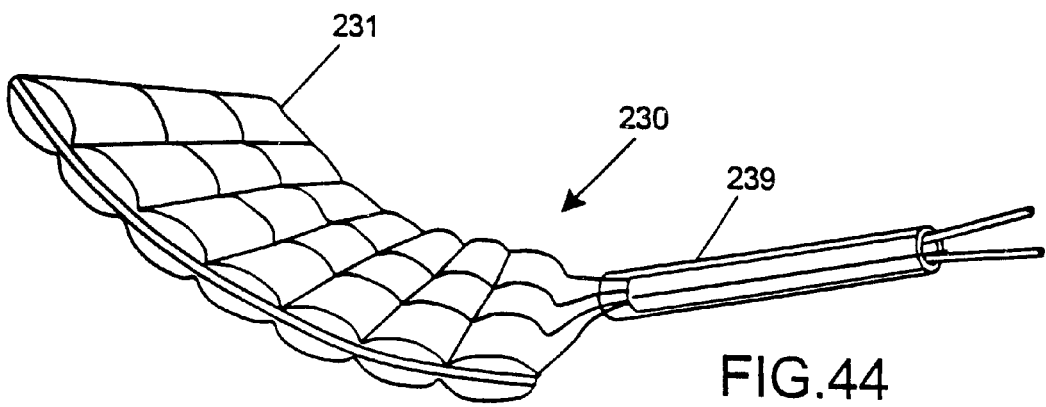
FIG. 44 shows the topical hypothermia device of FIG. 42 in a deployed position.
Figure 45:
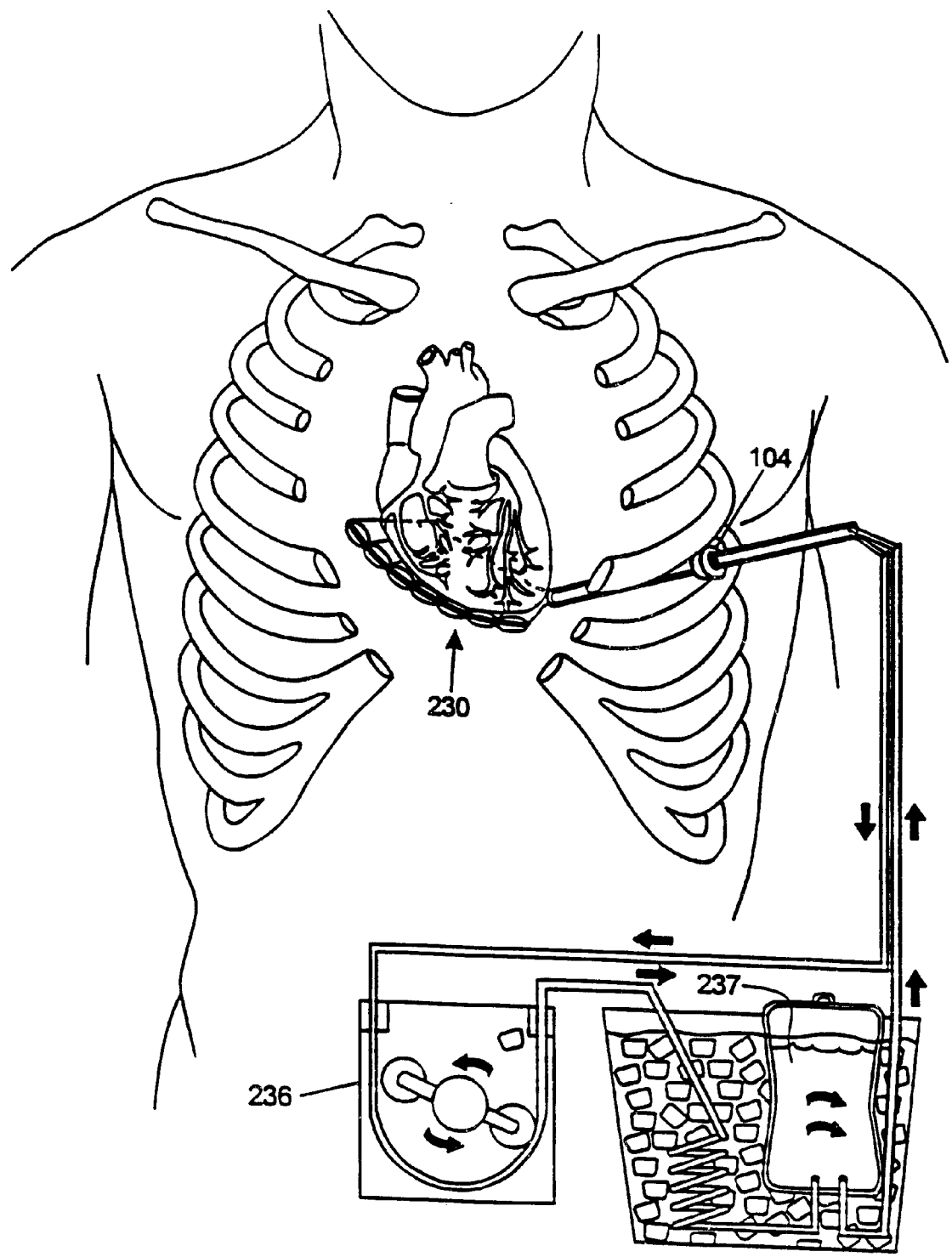
FIG. 45 shows the topical hypothermia device of FIG. 42 in use within the chest of a patient.

In use, the topical hypothermia device 230 is prepared in the predeployed position by first priming the flexible heat exchanger 231 by filling it with cooling fluid and connecting the proximal end of the inflow lumen 234 and the return lumen 235 to the circulating pump 236 and the reservoir of cooling fluid 237. The flexible heat exchanger 231 is rolled and covered with the introducer sheath 239. The topical hypothermia device 230 is inserted through one of the access ports 104 in this predeployed position. The distal end of the introducer sheath 239 is placed under the heart H and then withdrawn proximally with respect to the flexible heat exchanger 231, thereby placing the flexible heat exchanger 231 underneath the heart H. Alternatively, the sheath 239 can be withdrawn after the topical hypothermia device 230 is introduced through the access port 104 and the flexible heat exchanger 231 placed under the heart H with the help of the flexible backbone 238. The circulating pump 236 is turned on to force cooling fluid into the flexible heat exchanger 231 and through the cooling passage 232. The flexible heat exchanger 231 inflates with cooling fluid and spreads out under the heart H to make good thermal contact with the myocardium, as shown in FIG. 45. Preferably, the flexible heat exchanger 231 is constructed so that it curves to conform to the exterior of the heart H when inflated to the deployed position, as shown in FIG. 44, to create a better thermal contact with the myocardium. Typically, a cooling fluid at 0–4 degrees Celcius is circulated through the flexible heat exchanger 231 with a flow rate of greater than 350 ml/min to rapidly cool the heart.

In an alternate embodiment of the topical cooling device, the flexible heat exchanger 231 may also be covered with a thermal insulating material, such as surgical felt, to prevent thermal shock to the myocardial tissue. Another way to avoid thermal shock to the myocardial tissue is to use a more moderate temperature for the cooling fluid, with better thermal contact and a higher flow rate to rapidly cool the myocardium without the risk of thermal shock.

Figure 46:
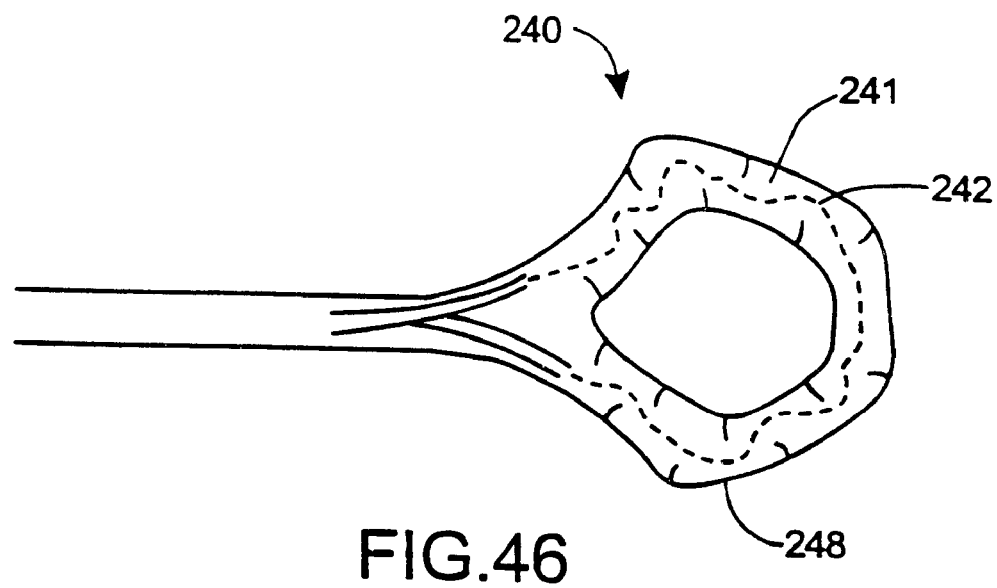
FIG. 46 shows a second embodiment of a topical hypothermia device for cooling a patients heart to improve myocardial protection during port-access cardiac surgery.
Figure 47:
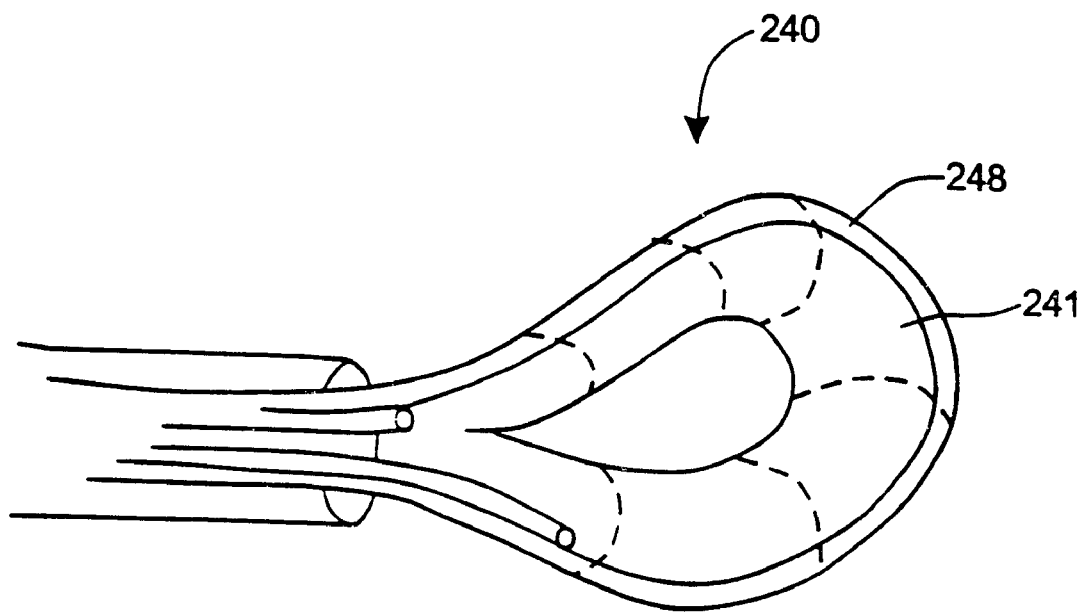
FIG. 47 shows the topical hypothermia device of FIG. 46 in a deployed position.

FIG. 46 shows an alternate embodiment of the topical cooling device 240, which is similar to the embodiment of FIG. 42 except for the construction of the flexible heat exchanger 241. In this embodiment, the flexible heat exchanger is in the form of a ring made by heat sealing two sheets of plastic together. The cooling fluid enters one side of the ring-shaped heat exchanger and follows a serpentine cooling path 242 through the heat exchanger 241 around to the other side of the ring. A preformed, resilient wire loop 248 is attached around the outside of the ring-shaped heat exchanger 241 to initialize the shape of the heat exchanger 241 during deployment, as shown in FIG. 47.

The topical cooling device 230, 240 can be used alone to induce hypothermic cardiac arrest in the patient's heart or the topical cooling device 230, 240 can be used in conjunction with cardioplegic arrest to improve the myocardial protection during the surgical procedure. In addition, the topical cooling device 230, 240 can be used to rewarm the heart after the completion of the surgical procedure by circulating warm fluid through the flexible heat exchanger 231, 241. In addition to the multivessel CABG procedure of the present invention, the topical cooling device 230, 240 will find utility for improving myocardial protection in any open-chest or closed-chest cardiac surgery.

Figure 48:
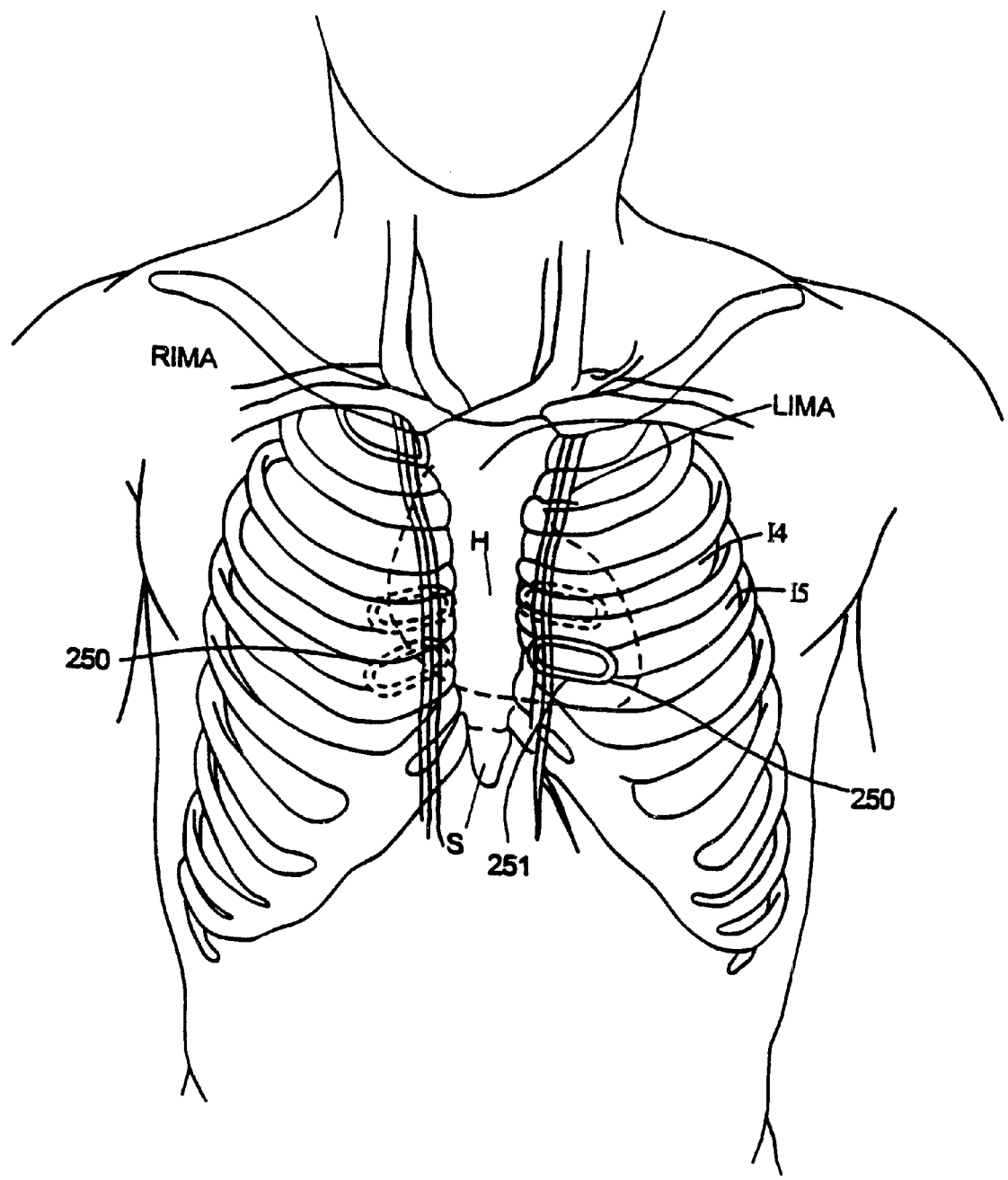
FIG. 48 shows a first embodiment of an anterior mediastinotomy approach for performing closed-chest multivessel CABG surgery.
Figure 49:
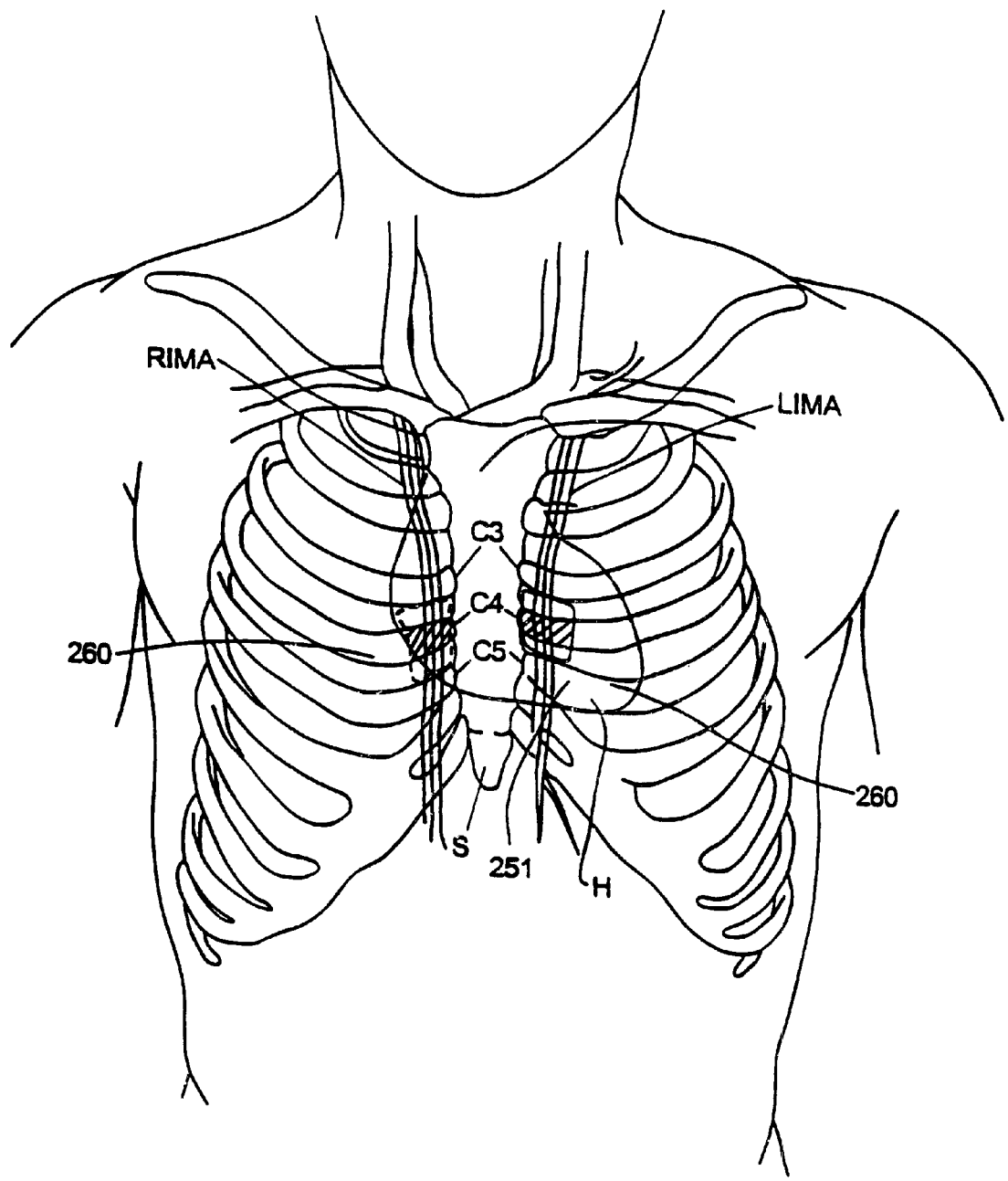
FIG. 49 shows a second embodiment of an anterior mediastinotomy approach for performing closed-chest multivessel CABG surgery.

Another closely related surgical approach for performing closed-chest multivessel CABG surgery is through an anterior mediastinotomy, that is, through an incision into the mediastinum, the mass of tissues and organs between the lungs that includes the heart. Another term for this surgical approach is a rib-sparing, anterior mini-thoracotomy. There are two ways to perform the anterior mediastinotomy for this approach. The first way is through an intercostal incision 250, 25–50 mm long, in the fourth I4 or fifth I5 intercostal space to the left of the sternum S, as shown in FIG. 48. The second way is to create a larger access port 260 by removing either the third C3, fourth C4 or fifth C5 costal cartilage, preferably on the left side of the sternum S. When one of the costal cartilages is removed, it creates an access port 260 approximately 50–60 mm square, as shown in FIG. 49. The access port 260 can be held open using a tissue spreader for an access cannula which is oval or square in shape. Actual cutting or removal of ribs is not necessary. The best position for the port may be decided by viewing through the lateral IMA takedown ports in the third or fourth intercostal space and probing with a needle to find the best position and line of sight for the particular anastomosis site. It should be noted that, because the anterior mediastinotomy may cut across the path of the internal mammary artery, it is preferable to make the access port after completion of the IMA takedown.

A tissue spreader or oval cannula 251 for retraction would be useful to maintain the access channel. Retraction of the ribs should be kept to a minimum in order to reduce the trauma to the patient. For introduction without retraction of the ribs, the oval cannula 251 should have interior dimensions of approximately 12 mm width and 25–50 mm length, and a thin wall of approximately 1 mm thick. For varying degrees of retraction, the width of the oval cannula 251 can be increased anywhere from 12 mm to 25 mm, which should be sufficient for adequate visualization and instrument access. Visualization and instrument insertion can thus be accomplished through a single elongated access port, rather than using separate visualization and instrument ports as in the port-access approach described above. Visualization can be accomplished using a surgical microscope, as described above, or by direct visualization through the access port 250, 260, with or without magnifying loupes. The cannula 251 should be configured to facilitate retraction of the pedicle through the lumen of the cannula without harm so that the distal end of the graft vessel can be prepared for anastomosis outside of the body under direct visualization. Therefore, the cannula 251 should have no sharp edges that could harm the graft vessel or pedicle. The insertion length of the cannula 251 should be about 25–50 mm.

Preferably, illumination means are incorporated into the oval cannula 251 or into the tissue spreader used to maintain the access channel. A light conduction path is incorporated into the wall of the oval cannula 251 or into the blades of the tissue spreader to direct a beam of light distally onto the surgical site. A light source is connected to the light conduction path. The light source can be integrated into the device or an external light source may be connected to the device by an optical cable.

Figure 50:
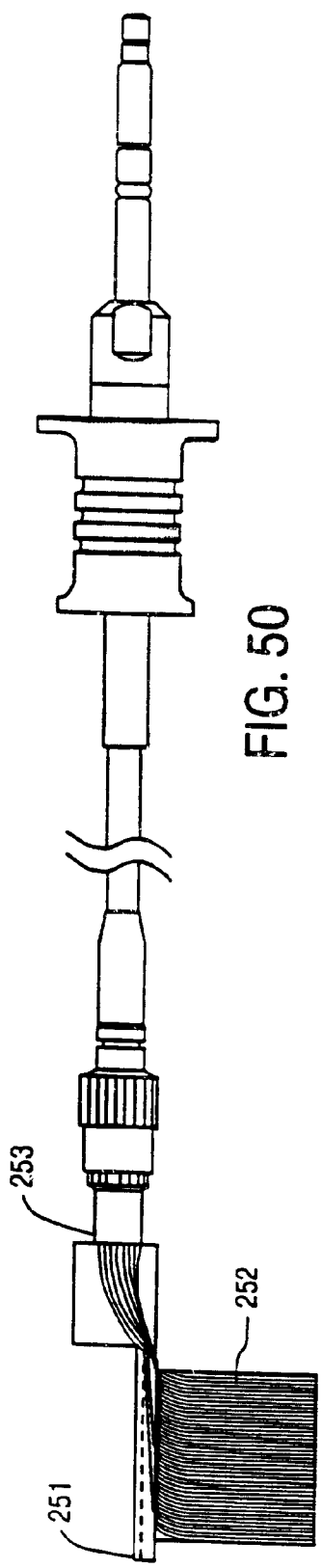
FIG. 50 shows a top view of a fiberoptically illuminated oval access cannula.
Figure 51:
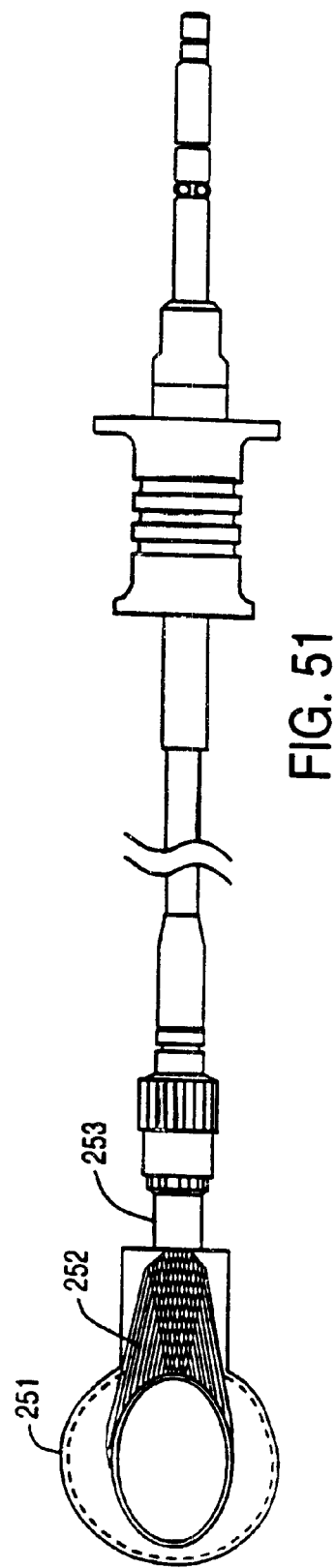
FIG. 51 shows a side view of the fiberoptically illuminated oval access cannula of FIG. 50.

An exemplary embodiment of an illuminated access device is shown in a top view in FIG. 50 and a side view in FIG. 51. This particular embodiment is an illuminated oval cannula 251, however the following inventive features can also be incorporated into a blade retractor, tissue spreader, or standard circular access cannula. Optical fibers 252 are embedded into the wall of the oval cannula 251. The optical fibers terminate at the distal end of the cannula 251 to direct a beam of light distally toward the surgical site. A narrow or diffuse beam of light can be created depending on the arrangement and the numerical aperture of the optical fibers. At the proximal end of the cannula 251, the optical fibers 252 gather together into an optical connector 253 for connection to an external light source. In one currently preferred embodiment, a multiplicity of small diameter optical fibers are distributed evenly about the periphery of the oval cannula 251. The wall of the oval cannula 251 can be made of an opaque material to avoid light escaping from the optical fibers 252 from interfering with visualization through the lumen 254 of the cannula 251. Alternatively, the interior and/or exterior wall of the cannula 251 can be made transparent or translucent to create a diffuse ambient light within or around the cannula 251.

Anastomosis between the graft vessel and the coronary artery is performed using instruments inserted through the access port 250, 260. One advantage of this approach is that the access port 250, 260 is large enough so that the surgeon can insert a finger through the access port or oval cannula 251 to directly palpate the heart, for instance to locate a stenosis in the coronary artery. It may be advantageous to elevate the heart within the thoracic cavity to facilitate palpation of the heart and/or performing the anastomosis. A device similar to the topical cooling devices 230, 240 of FIGS. 42–47 may be used to elevate the heart H within the thoracic cavity by inserting it underneath the heart and inflating it, with or without circulating cooling fluid. The tunneling and retraction devices of FIGS. 22–41 can be used through the access port or through the takedown ports to manipulate the heart to expose different aspects of the heart for visualization and anastomosis of multiple coronary arteries according to the methods described above. Alternatively, a second mediastinal access port 250', 260' can be opened on the right side of the chest to access the right coronary artery directly. In another alternative approach, a right side mediastinal access port 250', 260' may be used alone if only the right coronary artery is to be revascularized or if the patient's anatomy favors a right side approach for multivessel revascularization.

What is claimed is:

1. A surgical tunneling instrument for tunneling between adjacent body structures in a body cavity, the tunneling instrument comprising:

a shaft having a distal end, a proximal end and a lumen therebetween;

a linkage extending through the lumen;

an articulating finger at the end of the shaft, the articulating finger comprising:

a first proximal member having a proximal end and a distal end opposite the proximal end, the proximal end being pivotably coupled to the shaft at a first point and coupled to the linkage at a second point laterally offset from the first point;

a second proximal member having a proximal end pivotably coupled to the shaft and a distal end opposite the proximal end; and a distal member having a proximal end and a distal end opposite the proximal end, the distal end being configured for tunneling between the body structures, and the proximal end being pivotably coupled to the distal end of the first proximal member at a third point and pivotably coupled to the distal end of the second proximal member at a fourth point laterally offset from the third point; and means at the proximal end of the shaft for moving the linkage relative to the shaft, whereby the first proximal member pivots relative to the shaft about the first point and the distal member pivots relative to the first proximal member about the third point.

2. The tunneling instrument of claim 1 further comprising means at the distal end of the distal member for grasping a vascular structure.

3. The tunneling instrument of claim 2 wherein the grasping means comprises a hook.

4. The tunneling instrument of claim 2 wherein the grasping means comprises a snare.

5. The tunneling instrument of claim 2 wherein the grasping means comprises a pair of grasping jaws, at least one of said grasping jaws being movable with respect to the other.

6. The tunneling instrument of claim 2 wherein the first and second points are separated by a first transverse distance, and the third and fourth points are separated by a second transverse distance, the first and second transverse distances being less than about 10 mm.

* * * * *